(12) United States Patent
Lahann et al.

(10) Patent No.: US 12,280,159 B2
(45) Date of Patent: *Apr. 22, 2025

(54) THERAPEUTIC PROTEIN-BASED NANOPARTICLES FOR TREATING CANCER

(71) Applicant: THE REGENTS OF THE UNIVERSITY OF MICHIGAN, Ann Arbor, MI (US)

(72) Inventors: Joerg Lahann, Ann Arbor, MI (US); Nahal Habibi, Ann Arbor, MI (US); Jason V. Gregory, Ann Abor, MI (US); Maria Castro, Ann Arbor, MI (US); Pedro Lowenstein, Ann Arbor, MI (US); Ava Mauser, Corrales, NM (US); Padma Kadiyala, Ann Arbor, MI (US); Daniel F. Quevedo, Lexington, VA (US); Felipe Nunez, Ann Arbor, MI (US)

(73) Assignee: The Regents of The University of Michigan, Ann Arbor, MI (US)

( * ) Notice: Subject to any disclaimer, the term of this patent is extended or adjusted under 35 U.S.C. 154(b) by 148 days.

This patent is subject to a terminal disclaimer.

(21) Appl. No.: 17/521,414

(22) Filed: Nov. 8, 2021

(65) Prior Publication Data

US 2022/0142936 A1 May 12, 2022

Related U.S. Application Data

(60) Provisional application No. 63/120,589, filed on Dec. 2, 2020, provisional application No. 63/112,086, filed on Nov. 10, 2020, provisional application No. 63/110,828, filed on Nov. 6, 2020.

(51) Int. Cl.
| | |
|---|---|
| *B82Y 5/00* | (2011.01) |
| *A61K 9/51* | (2006.01) |
| *A61K 31/7105* | (2006.01) |
| *A61P 35/00* | (2006.01) |
| *A61K 9/00* | (2006.01) |
| *B82Y 40/00* | (2011.01) |

(52) U.S. Cl.
CPC .......... *A61K 9/5169* (2013.01); *A61K 9/5192* (2013.01); *A61K 31/7105* (2013.01); *A61P 35/00* (2018.01); *A61K 9/0085* (2013.01); *B82Y 5/00* (2013.01); *B82Y 40/00* (2013.01)

(58) Field of Classification Search
CPC ... A61K 9/5192; A61K 31/7105; A61P 35/00; B82Y 5/00; B82Y 40/00
See application file for complete search history.

(56) References Cited

U.S. PATENT DOCUMENTS

| | | | |
|---|---|---|---|
| 7,767,017 B2 | 8/2010 | Lahann et al. | |
| 2008/0242774 A1 | 10/2008 | Lahann et al. | |
| 2010/0015447 A1 | 1/2010 | Lahann et al. | |
| 2010/0038830 A1 | 2/2010 | Lahann et al. | |
| 2010/0233781 A1 | 9/2010 | Bangera et al. | |
| 2012/0045487 A1 | 2/2012 | Lahann et al. | |
| 2013/0115169 A1 | 5/2013 | Lahann et al. | |
| 2022/0142936 A1 | 5/2022 | Lahann et al. | |

FOREIGN PATENT DOCUMENTS

| | | | |
|---|---|---|---|
| WO | 2010011641 A2 | 1/2010 | |
| WO | WO-2015111062 A1 * | 7/2015 | ........... A61K 31/404 |
| WO | 2021092452 A1 | 5/2021 | |

OTHER PUBLICATIONS

Li et al., J. Mater. Chem. B, 2016, 4, 6620-6639. (Year: 2016).*
Gong et al., Journal of Controlled Release 266 (2017) 272-286. (Year: 2017).*
Zhang et al., ACS Appl. Bio. Mater. 2019, 2,3, 1168-1176. (Year: 2019).*
Taylor et al., Apoptosis (2018) 23:563-575. (Year: 2018).*
Gulfam et al., Langmuir 2012, 28, 8216-8223 (Year: 2012).*
Choi et al., Nanoscale, 2015, 7, 9229. (Year: 2015).*
Zuo, J. Oncology, vol. 2019, Article ID 9367845, 1-15. (Year: 2019).*
Kang et al., Polymers 2020, 12, 1906, 1-27. (Year: 2020).*
Li et al., Designing hydrogels for controlled drug delivery, Nat Rev Mater, Dec. 2016.
Habibi et al. "Engineered Ovalbumin Nanoparticles for Cancer Immunotherapy," Advanced Therapeutics, Jul. 9, 2020, vol. 3, Iss. 10, pp. 1-11.
International Search Report and Written Opinion for PCT Application No. PCT/US20/59497 issued Feb. 9, 2021; 10 pages.
Gregory et al., Systemic Brain Tumor Delivery of Synthetic Protein Nanoparticles for Glioblastoma Therapy, Nature Communications, (2020) 11:5687.
Demento et al., Role of sustained antigen release from nanoparticle vaccines in shaping the T cell memory phenotype, Biomaterials, vol. 33, Issue 19, Year 2012.
Scott et al., Tunable T cell immunity towards a protein antigen using polymersomes vs. solid-core nanoparticles, Biomaterials, vol. 34, Issue 17, Year 2013.

(Continued)

*Primary Examiner* — Robert S Cabral
(74) *Attorney, Agent, or Firm* — Harness, Dickey & Pierce, P.L.C.

(57) ABSTRACT

Protein-based nanoparticles for treating cancer, such as those characterized by intracranial tumors, and methods of forming such protein-based nanoparticles via electrohydrodynamic jetting methods are provided. The nanoparticle may comprise a water-soluble protein having an average molecular weight of ≥about 8 kDa and ≤about 700 kDa. In certain variations, the water-soluble protein is cross-linked (e.g., with an optional crosslinking agent) and defines a mesh structure having an average linear mesh size of ≥about 1 nm to ≤about 4 nm. The nanoparticle may have a transcription factor such as a therapeutic nucleic acid in the mesh structure. Methods of making such nanoparticles may include jetting a liquid comprising the water-soluble protein through a nozzle, followed by exposing the liquid to an electric field sufficient to solidify the liquid and form the protein-based nanoparticles described above.

25 Claims, 42 Drawing Sheets

(56) References Cited

OTHER PUBLICATIONS

Chen et al., Oncology Meets Immunology: The Cancer-Immunity Cycle, Immunity, vol. 39, Issue 1, Year 2013.
Roh et al.; "Biphasic Janus Particles With Nanoscale Anisotropy"; Nature Materials, vol. 4; Oct. 2005; pp. 759-763.
Unzueta et al., Engineering multifunctional protein nanoparticles by in vitro disassembling and reassembling of heterologous building blocks, Nanotechnology, vol. 28, (2017).
Zheng et al., Enhanced Antiarthritic Efficacy by Nanoparticles of (−)-Epigallocatechin Gallate-Glucosamine-Casein, J. Agric. Food Chem. (2019), 67, 23, 6476-6486.
Zhou et al., Boiling Licorice Produces Self-Assembled Protein Nanoparticles: A Novel Source of Bioactive Nanomaterials, J. Agric. Food Chem. (2019), 67, 33, 9354-9361.
Mason et al., Predicting Controlled-Release Behavior of Degradable PLA-b-PEG-b-PLA Hydrogels, Macromolecules (2001), 34, 13, 4630-4635.
Gomez et al., Generation of Monodisperse Protein Nanoparticles by Electrospray Drying, Mat. Res. Soc. Symp. Proc. vol. 550, Year 1999.
Liu, et al., Emulsifying Properties of Soy Protein Nanoparticles: Influence of the Protein Concentration and/or Emulsification Process, J. Agric. Food Chem. (2014), 62, 12, 2644-2654.
Swati Mahobia, et al., Soya protein as possible potential nanocarriers for in-vitro oral delivery of insulin in simulated gastric fluids (SGFs), International Journal of Polymeric Materials and Polymeric Biomaterials, vol. 67 2018, Issue 6, pp. 340-350, DOI: 10.1080/00914037.2017.1327435, Aug. 11, 2017.
Jain et al., Protein Nanoparticles: Promising Platforms for Drug Delivery Applications, ACS Biomater. Sci. Eng. 2018, 4, 12, 3939-3961, Nov. 2, 2018.
Juan Manuel Urueña et al., Mesh Size Control of Polymer Fluctuation Lubrication in Gemini Hydrogels, Biotribology, pp. 24-29, Mar. 12, 2015.
Canal, T., et al., Correlation between mesh size and equilibrium degree of swelling of polymeric networks, Journal of Biomedical Materials Research, 1183-1193, Oct. 1989.
N. Kawakami et al., Design of Hollow Protein Nanoparticles with Modifiable Interior and Exterior Surface, Angew. Chem. Int. Ed. Vol. 57, Issue 38, Jul. 31, 2018.
Fangjian Ning et al., Double-induced se-enriched peanut protein nanoparticles preparation, characterization and stabilized food-grade pickering emulsions, Food Hydrocolloids 99 (2020) 105308, Aug. 13, 2019.
C. Weber et al., Desolvation process and surface characterisation of protein nanoparticles, International Journal of Pharmaceutics, vol. 194, Issue 1, Year 2000.
Silvia L. Soto Espinoza, et al., Radiation synthesis of seroalbumin nanoparticles, Radiation Physics and Chemistry, vol. 81, Issue 9, Year 2012.
Izlia J. Arroyo-Maya, et al., a-Lactalbumin nanoparticles prepared by desolvation and cross-linking: Structure and stability of the assembled protein, Biophysical Chemistry, vols. 193-194, Year 2014.
Verma et al., Protein Based Nanostructures for Drug Delivery, Journal of Pharmaceutics, vol. 2018, Article ID 9285854, 18 pages, May 16, 2018.
Ruoyang Xu, Zi Teng, Qin Wang, Development of tyrosinase-aided crosslinking procedure for stabilizing protein nanoparticles, Food Hydrocolloids, vol. 60, Apr. 7, 2016.
Yu, X. et al. Activatable Protein Nanoparticles for Targeted Delivery of Therapeutic Peptides, Adv. Mater., doi:10.1002/adma.201705383, Feb. 2018.
Morozova et al., Protein nanoparticles with ligand-binding and enzymatic activities, International Journal of Nanomedicine, 2018:13 6637-6646, Year 2018.
Saha et al., Fatty-Amine-Conjugated Cationic Bovine Serum Albumin Nanoparticles for Target-Specific Hydrophobic Drug Delivery, ACS Appl. Nano Mater. 2019, 2, 6, 3671-3683, May 8, 2019.
Golla, Kishore et al. "A target-specific oral formulation of Doxorubicin-protein nanoparticles: efficacy and safety in hepatocellular cancer." Journal of Cancer vol. 4,8 644-52. Sep. 14, 2013, doi:10.7150/jca.7093.
Ahmed O. Elzoghby, et al., Chapter Six—Implications of Protein- and Peptide-Based Nanoparticles as Potential Vehicles for Anticancer Drugs, Advances in Protein Chemistry and Structural Biology, Academic Press, vol. 98, http://dx.doi.org/10.1016/bs.apcsb.2014.12.002, Year 2015.
Wen et al., Self-Templated, Green-Synthetic, Size-Controlled Protein Nanoassembly as a Robust Nanoplatform for Biomedical Application, ACS Appl. Mater. Interfaces, Mar. 6, 2018.
Zeng et al., Scalable Production of Therapeutic Protein Nanoparticles Using Flash Nanoprecipitation, Adv. Healthcare Materials, DOI: 10.1002/adhm.201801010, Year 2018.
Zahra Chavoshpour-Natanzi, et al, Encapsulation of quercetin-loaded B-lactoglobulin for drug delivery using modified antisolvent method, Food Hydrocolloids, vol. 96, May 28, 2019.
Yang et al., Nonlinear Behavior of Gelatin Networks Reveals a Hierarchical Structure, Biomacromolecules, DOI: 10.1021/acs.biomac.5b01538, Dec. 14, 2015.
Rehmann et al., Tuning and Predicting Mesh Size and Protein Release from Step Growth Hydrogels, Biomacromolecules,doi:10.1021/acs.biomac.7b00781, Oct. 9, 2017.
Gregory M. Cruise, David S. Scharp, Jeffrey A. Hubbell, Characterization of permeability and network structure of interfacially photopolymerized poly(ethylene glycol) diacrylate hydrogels, Biomaterials, vol. 19, Issue 14, Year 1998.
Saffer et al., SANS study of highly resilient poly(ethylene glycol) hydrogels, Soft Matter, DOI: 10.1039/c3sm52395k, Jan. 6, 2014.
A. Gomez, D., et al., Production of protein nanoparticles by electrospray drying, Journal of Aerosol Science, vol. 29, Issues 5-6, Year 1998.
Alvarez et al, Nanotechnology Rapid generation of protein aerosols and nanoparticles via surface acoustic wave atomization, Nanotechnology, doi: 10.1088/0957-4484/19/45/455103, Oct. 8, 2008.
Sie Huey Lee, et al., Nano spray drying: A novel method for preparing protein nanoparticles for protein therapy, International Journal of Pharmaceutics, vol. 403, Issues 1-2, Year 2011.
Kumar, et al., Novel, Simple, Versatile and General Synthesis of Nanoparticles Made from Proteins, Nucleic Acids and Other Materials, Journal of Nano Research, vol. 12, Trans Tech Publications, Ltd., Dec. 2010, pp. 77-88. Crossref, doi:10.4028/www.scientific.net/jnanor.12.77.
Kyuya Nakagawa, et al., Characterization of casein-based nanoparticles formed upon freezing by in situ SAXS measurement, Colloids and Surfaces B: Biointerfaces, vol. 103, Year 2013.
Hong Jai Lee, et al., Enzyme delivery using the 30Kc19 protein and human serum albumin nanoparticles, Biomaterials, vol. 35, Issue 5, Year 2014.
Surender K. Dhayal, et al., Controlled formation of protein nanoparticles by enzymatic cross-linking of a-lactalbumin with horseradish peroxidase, Food Hydrocolloids, vol. 36, Year 2014.
Lina Herrera Estrada, et al., Protein Nanoparticles for Intracellular Delivery of Therapeutic Enzymes, Journal of Pharmaceutical Sciences, vol. 103, Issue 6, Year 2014.
Estrada et al., "Protein nanoparticles for therapeutic protein delivery ," Biomater. Sci., DOI: 10.1039/c5bm00052a, May 2, 2015.
Mohamad Tarhini, et al., Protein-based nanoparticles: From preparation to encapsulation of active molecules, International Journal of Pharmaceutics, vol. 522, Issues 1-2, Year 2017.
Fang Li, et al., Preparation and characterization of redox-sensitive glutenin nanoparticles, International Journal of Biological Macromolecules, vol. 137, Year 2019.
Rahmani, Sahar, "Multifunctional Drug Carriers with Programmable Properties," Year 2015.
Gregory et al. "Systemic Brain Tumor Delivery of Synthetic Protein Nanoparticles for Glioblastoma Therapy," Online pre-publication, Year 2019.
Habibi, Nahal, Harnessing Immune System to Battle Cancer by Using Protein-Based Nanoparticles, PharmSci360, Year 2019.
International Search Report and Written Opinion regarding International application No. PCT/US2020/059497, dated Feb. 9, 2021.

(56) References Cited

OTHER PUBLICATIONS

U.S. Appl. No. 17/775,229, filed May 6, 2022, Nahal Habibi et al.

Kasarda, Donald D. et al.; "Reversible Aggregation of a-Gliadin to Fibrils"; Source: Science, Jan. 13, 1967, New Series, vol. 155, No. 3759 (Jan. 13, 1967); pp. 203-205. Published by: American Association for the Advancement of Science.

Umamaheshwari, R.B. et al; "Anti-Helicobacter Pylori Effect of Mucoadhesive Nanoparticles Bearing Amoxicillin in Experimental Gerbils Model"; AAPS PharmSciTech 2004; 5 (2) Article 32 (http://www.aapspharmscitech.org); 9 pages.

Urade, Reiko et al; "Gliadins from wheat grain: an overview, from primary structure to nanostructures of aggregates"; Biophysical Reviews (2018) 10:435-443; https://doi.org/10.1007/s12551-017-0367-2.

\* cited by examiner

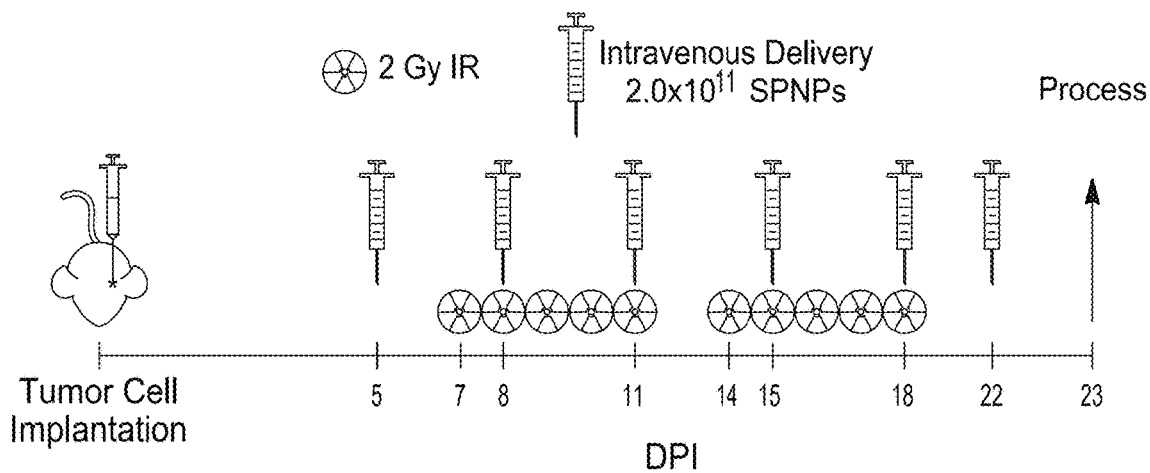
FIG - 27A
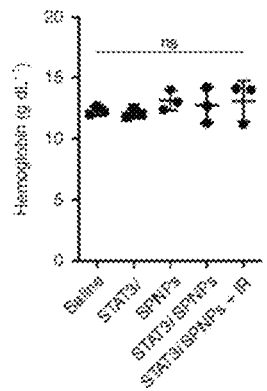 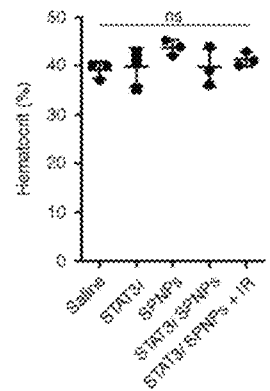 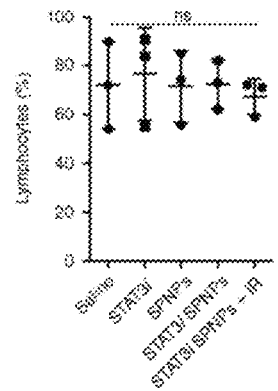 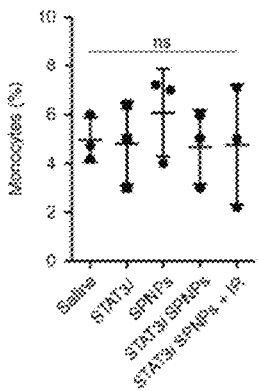
FIG - 27B  FIG - 27C  FIG - 27D  FIG - 27E
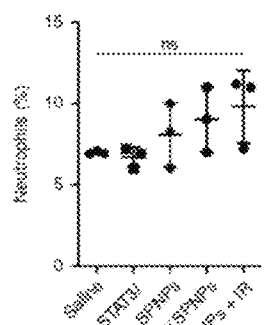 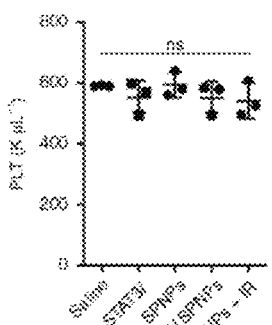 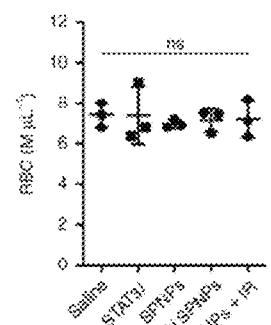 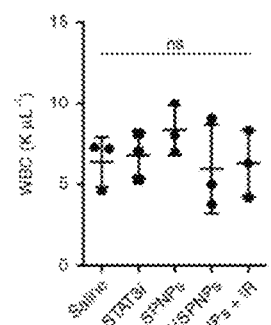
FIG - 27F  FIG - 27G  FIG - 27H  FIG - 27I

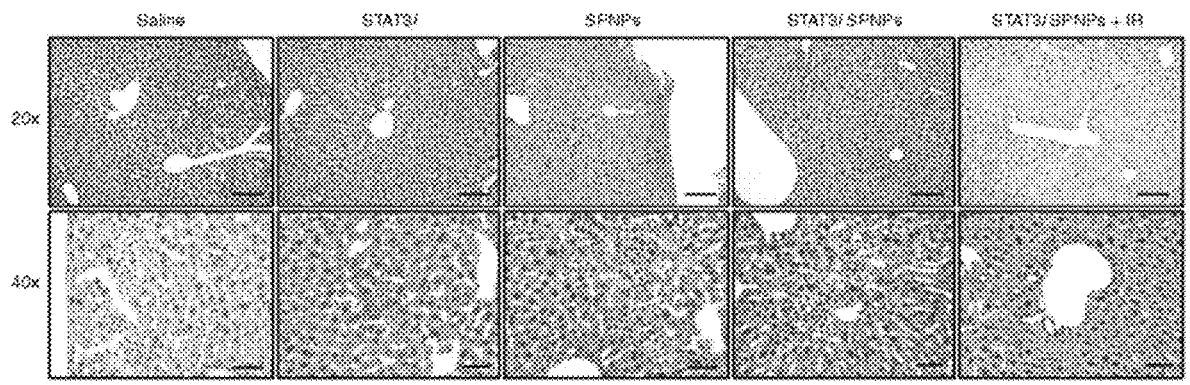
FIG - 27J
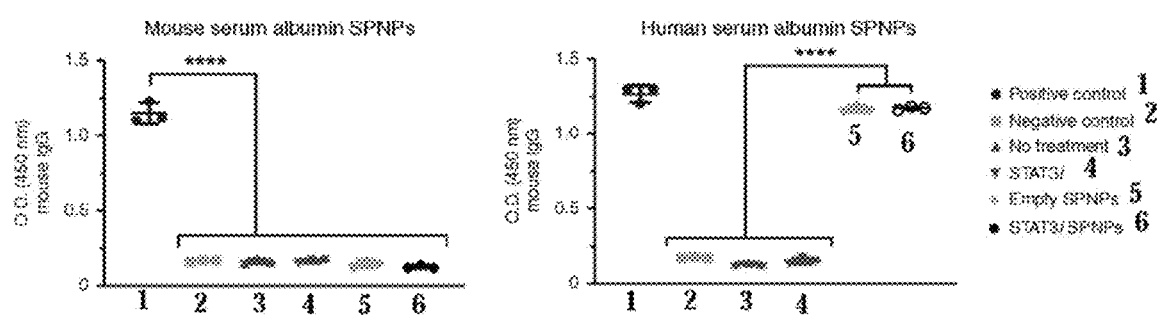
FIG - 27K
FIG - 27L

Mouse serum biochemical analysis following intravenous STAT3i SPNP + IR treatment
23 DPI (n = 3)

| Group | Creatinine (μM) | BUN (mM) | ALT (U L$^{-1}$) | AST (U L$^{-1}$) |
|---|---|---|---|---|
| Saline | 0.21 ± 0.10 | 26 ± 3.1 | 111 ± 45.2 | 328 ± 31.4 |
| STAT3i | 0.20 ± 0.04 | 23 ± 5.0 | 98 ± 9.2 | 331 ± 40.2 |
| SPNPs | 0.23 ± 0.10 | 27 ± 2.1 | 102 ± 4.0 | 342 ± 32.1 |
| STAT3i SPNPs | 0.17 ± 0.20 | 23 ± 3.0 | 97 ± 3.5 | 332 ± 28.2 |
| STAT3i SPNPs + IR | 0.20 ± 0.06 | 28 ± 1.2 | 99 ± 2.6 | 320 ± 45.0 |

FIG. 28

THERAPEUTIC PROTEIN-BASED NANOPARTICLES FOR TREATING CANCER

CROSS-REFERENCE TO RELATED APPLICATIONS

This application claims the benefit of U.S. Provisional Application Nos. 63/110,828 filed on Nov. 6, 2020, 63/112,086 filed on Nov. 10, 2020, and 63/120,589 filed on Dec. 2, 2020. The entire disclosures of the above applications are incorporated herein by reference.

FIELD

The present disclosure relates to therapeutic nanoparticles comprising at least one cross-linked water-soluble protein and electrohydrodynamic jetting methods for making the same.

BACKGROUND

This section provides background information related to the present disclosure which is not necessarily prior art.

Clinical translation of nanoparticle-based drug delivery systems is hindered by an array of challenges including poor circulation time and limited targeting.

In recent decades, many nanoparticle technologies have been developed for use in a variety medical applications. Generally, nanoparticles may be considered to be colloidal particles ranging in size from nanometers into the submicron range. However, the scope of their properties, modes of preparation, compositions, and architectures vary vastly. Such nanoparticles can be used in numerous biomedical applications including drug delivery, cancer therapy (e.g., glioblastoma), tissue engineering, medical imaging and diagnostics, and immunotherapy.

There remains a need in the field for development of improved nanoparticle-based drug delivery systems aimed to provide: (i) protection of loaded cargo from degradation or deactivation, (ii) potential controlled release mechanisms, and (iii) altered pharmacokinetics and specific control of biodistribution. In particular, such improved nanoparticle-based drug delivery systems for treatment of cancer would be particularly advantageous.

SUMMARY

This section provides a general summary of the disclosure, and is not a comprehensive disclosure of its full scope or all of its features.

The present disclosure relates to therapeutic protein-based nanoparticles and methods for making the protein-based nanoparticles.

In various aspects, the current technology provides a nanoparticle including a cross-linked water-soluble protein having a mesh structure, wherein the water-soluble protein has an average molecular weight of greater than or equal to about 8 kDa and less than or equal to about 700 kDa.

In one aspect, the mesh structure has an average linear mesh size of greater than or equal to about 1 nm to less than or equal to about 4 nm.

In one aspect, the nanoparticle includes a crosslinking agent conjugated to the water-soluble protein.

In one aspect, the nanoparticle includes an inhibitor of a transcription factor encapsulated in the mesh structure.

In one aspect, the cross-linked water soluble protein is present at greater than or equal to about 50% by weight to less than or equal to about 95% by weight, and wherein the crosslinking agent is present at greater than or equal to about 5% by weight to less than or equal to about 50% by weight.

In one aspect, prior to reacting with the water-soluble protein, the crosslinking agent includes a reactive group selected from the group consisting of an alkenyl group, an alkynyl group, a maleimide group, an active ester group, an anhydride group, an N-succinimidyl group, a triflate group, and a combination thereof.

In one aspect, the crosslinking agent is a homo-bifunctional polymer.

In one aspect, the nanoparticle further includes one or more of a therapeutic active ingredient, an imaging agent, and a targeting moiety (e.g., a cell penetrating peptide, e.g., iRGD).

In one aspect, the nanoparticle includes a therapeutic active ingredient, which is a biomolecule.

In one aspect, the biomolecule is a nucleic acid.

In one aspect, the biomolecule is a DNA molecule.

In some embodiments, the biomolecule is an RNA molecule.

In some embodiments, the therapeutic active ingredient is an inhibitor or a transcription factor (e.g., an inhibitor of STAT3, such as siRNA against STAT3, an inhibitor of ATG7, such as siRNA against ATG7).

In one aspect, the water-soluble protein is selected from the group consisting of albumin, ovalbumin, mucin, transferrin, insulin, lysozyme, hemoglobin, collagen, catalase, horseradish peroxidase, glucose oxidase, and a combination thereof.

In some embodiments, the water-soluble protein is albumin, the targeting moiety is iRGD, and the therapeutic active ingredient is a therapeutic nucleic acid. In some embodiments, the therapeutic nucleic acid is RNA. In some embodiments, the RNA is siRNA against STAT3. In some embodiments, the RNA is siRNA against ATG7.

In another aspect, the invention provides a nanoparticle of any one of the preceding aspects for use in a method of treating a subject having a cancer. In some embodiments, the cancer is characterized by one or more intracranial tumors. In some embodiments, the cancer is a glioblastoma. In some embodiments, the cancer is diffuse astrocytoma. In some embodiments, the method further comprises administering a concurrent radiotherapy.

In another aspect, the invention features a nanoparticle for use in a method of treating a subject having a glioblastoma, wherein the nanoparticle comprises albumin cross-linked in mesh structure, wherein the mesh structure encapsulates a therapeutic nucleic acid, wherein the therapeutic nucleic acid is an inhibitor of STAT3. In some embodiments, the nanoparticle further comprises a cell penetrating peptide. In some embodiments, the cell penetrating peptide is iRGD. In some embodiments, the cross-linked albumin is present at greater than or equal to about 50% by weight to less than or equal to about 95% by weight, and wherein a crosslinking agent is present at greater than or equal to about 5% by weight to less than or equal to about 50% by weight. In some embodiment, the therapeutic nucleic acid is siRNA against STAT3. In some embodiments, the mesh structure has an average linear mesh size of greater than or equal to about 1 nm to less than or equal to about 4 nm. In some embodiments, the method further comprises administering a concurrent radiotherapy.

In another aspect, the invention features a nanoparticle for use in a method of treating a subject having diffuse astrocytoma, wherein the nanoparticle comprises albumin cross-linked in mesh structure, wherein the mesh structure encapsulates a therapeutic nucleic acid, wherein the therapeutic nucleic acid is an inhibitor of ATG7. In some embodiments, the nanoparticle further comprises a cell penetrating peptide. In some embodiments, the cell penetrating peptide is iRGD. In some embodiments, the cross-linked albumin is present at greater than or equal to about 50% by weight to less than or equal to about 95% by weight, and wherein a crosslinking agent is present at greater than or equal to about 5% by weight to less than or equal to about 50% by weight. In some embodiment, the therapeutic nucleic acid is siRNA against ATG7. In some embodiments, the mesh structure has an average linear mesh size of greater than or equal to about 1 nm to less than or equal to about 4 nm. In some embodiments, the method further comprises administering a concurrent radiotherapy.

In another aspect, the invention features a nanoparticle for use in a method of generating an anti-tumor cytotoxic T cell-mediated immune response, wherein the nanoparticle comprises albumin cross-linked in mesh structure, wherein the mesh structure encapsulates a therapeutic nucleic acid, wherein the therapeutic nucleic acid is an inhibitor of STAT3. In some embodiments, the nanoparticle further comprises a cell penetrating peptide. In some embodiments, the cell penetrating peptide is iRGD. In some embodiments, the cross-linked albumin is present at greater than or equal to about 50% by weight to less than or equal to about 95% by weight, and wherein a crosslinking agent is present at greater than or equal to about 5% by weight to less than or equal to about 50% by weight. In some embodiments, the therapeutic nucleic acid is siRNA against STAT3. In some embodiments, the mesh structure has an average linear mesh size of greater than or equal to about 1 nm to less than or equal to about 4 nm.

In another aspect, the invention features a nanoparticle for use in a method of generating an anti-tumor cytotoxic T cell-mediated immune response, wherein the nanoparticle comprises albumin cross-linked in mesh structure, wherein the mesh structure encapsulates a therapeutic nucleic acid, wherein the therapeutic nucleic acid is an inhibitor of ATG7. In some embodiments, the nanoparticle further comprises a cell penetrating peptide. In some embodiments, the cell penetrating peptide is iRGD. In some embodiments, the cross-linked albumin is present at greater than or equal to about 50% by weight to less than or equal to about 95% by weight, and wherein a crosslinking agent is present at greater than or equal to about 5% by weight to less than or equal to about 50% by weight. In some embodiments, the therapeutic nucleic acid is siRNA against ATG7. In some embodiments, the mesh structure has an average linear mesh size of greater than or equal to about 1 nm to less than or equal to about 4 nm.

In another aspect, the invention features a nanoparticle for use in a method of generating an anti-tumor humoral immune response, wherein the nanoparticle comprises albumin cross-linked in mesh structure, wherein the mesh structure encapsulates a therapeutic nucleic acid, wherein the therapeutic nucleic acid is an inhibitor of STAT3. In some embodiments, the nanoparticle further comprises a cell penetrating peptide. In some embodiments, the cell penetrating peptide is iRGD. In some embodiments, the cross-linked albumin is present at greater than or equal to about 50% by weight to less than or equal to about 95% by weight, and wherein a crosslinking agent is present at greater than or equal to about 5% by weight to less than or equal to about 50% by weight. In some embodiments, the therapeutic nucleic acid is siRNA against STAT3. In some embodiments, the mesh structure has an average linear mesh size of greater than or equal to about 1 nm to less than or equal to about 4 nm.

In another aspect, the invention features a nanoparticle for use in a method of generating an anti-tumor humoral immune response, wherein the nanoparticle comprises albumin cross-linked in mesh structure, wherein the mesh structure encapsulates a therapeutic nucleic acid, wherein the therapeutic nucleic acid is an inhibitor of ATG7. In some embodiments, the nanoparticle further comprises a cell penetrating peptide. In some embodiments, the cell penetrating peptide is iRGD. In some embodiments, the cross-linked albumin is present at greater than or equal to about 50% by weight to less than or equal to about 95% by weight, and wherein a crosslinking agent is present at greater than or equal to about 5% by weight to less than or equal to about 50% by weight. In some embodiments, the therapeutic nucleic acid is siRNA against ATG7. In some embodiments, the mesh structure has an average linear mesh size of greater than or equal to about 1 nm to less than or equal to about 4 nm.

In various aspects, the current technology also provides a method of treating a subject having a cancer, the method including administering to the subject the nanoparticle in an effective amount to treat the cancer.

In another aspect, the invention provides a method of treating a subject having a cancer by administering an effective amount of any of the nanoparticles described herein. In some embodiments, the cancer is characterized by one or more intracranial tumors. In some embodiments, the cancer is a glioblastoma. In some embodiments, the cancer may be diffuse astrocytoma. In some embodiments, the method further comprises administering a concurrent radiotherapy.

In another aspect, the invention features a method of treating a subject having a glioblastoma by administering an effective amount of a nanoparticle, or a composition thereof, wherein the nanoparticle comprises albumin cross-linked in mesh structure, wherein the mesh structure encapsulates a therapeutic nucleic acid, wherein the therapeutic nucleic acid is an inhibitor of STATS. In some embodiments, the nanoparticle further comprises a cell penetrating peptide. In some embodiments, the cell penetrating peptide is iRGD. In some embodiments, the cross-linked albumin is present at greater than or equal to about 50% by weight to less than or equal to about 95% by weight, and wherein a crosslinking agent is present at greater than or equal to about 5% by weight to less than or equal to about 50% by weight. In some embodiment, the therapeutic nucleic acid is siRNA against STATS. In some embodiments, the mesh structure has an average linear mesh size of greater than or equal to about 1 nm to less than or equal to about 4 nm. In some embodiments, the method further comprises administering a concurrent radiotherapy.

In another aspect, the invention features a method of treating a subject having a diffuse astrocytoma by administering an effective amount of a nanoparticle, or a composition thereof, wherein the nanoparticle comprises albumin cross-linked in mesh structure, wherein the mesh structure encapsulates a therapeutic nucleic acid, wherein the therapeutic nucleic acid is an inhibitor of ATG7. In some embodiments, the nanoparticle further comprises a cell penetrating peptide. In some embodiments, the cell penetrating peptide is iRGD. In some embodiments, the cross-linked albumin is present at greater than or equal to about 50% by weight to less than or equal to about 95% by weight, and wherein a crosslinking agent is present at greater than or equal to about 5% by weight to less than or equal to about 50% by weight. In some embodiment, the therapeutic nucleic acid is siRNA against ATG7. In some embodiments, the mesh structure has an average linear mesh size of greater than or equal to about 1 nm to less than or equal to about 4 nm. In some embodiments, the method further comprises administering a concurrent radiotherapy.

In another aspect, the invention features a method of generating an anti-tumor cytotoxic T cell-mediated immune response by administering an effective amount of a nanoparticle, or a composition thereof, wherein the nanoparticle comprises albumin cross-linked in mesh structure, wherein the mesh structure encapsulates a therapeutic nucleic acid, wherein the therapeutic nucleic acid is an inhibitor of STAT3. In some embodiments, the nanoparticle further comprises a cell penetrating peptide. In some embodiments, the cell penetrating peptide is iRGD. In some embodiments, the cross-linked albumin is present at greater than or equal to about 50% by weight to less than or equal to about 95% by weight, and wherein a crosslinking agent is present at greater than or equal to about 5% by weight to less than or equal to about 50% by weight. In some embodiments, the therapeutic nucleic acid is siRNA against STAT3. In some embodiments, the mesh structure has an average linear mesh size of greater than or equal to about 1 nm to less than or equal to about 4 nm.

In another aspect, the invention features a method of generating an anti-tumor cytotoxic T cell-mediated immune response by administering an effective amount of a nanoparticle, or a composition thereof, wherein the nanoparticle comprises albumin cross-linked in mesh structure, wherein the mesh structure encapsulates a therapeutic nucleic acid, wherein the therapeutic nucleic acid is an inhibitor of ATG7. In some embodiments, the nanoparticle further comprises a cell penetrating peptide. In some embodiments, the cell penetrating peptide is iRGD. In some embodiments, the cross-linked albumin is present at greater than or equal to about 50% by weight to less than or equal to about 95% by weight, and wherein a crosslinking agent is present at greater than or equal to about 5% by weight to less than or equal to about 50% by weight. In some embodiments, the therapeutic nucleic acid is siRNA against ATG7. In some embodiments, the mesh structure has an average linear mesh size of greater than or equal to about 1 nm to less than or equal to about 4 nm.

In another aspect, the invention features a method of generating an anti-tumor humoral immune response by administering an effective amount of a nanoparticle, or composition thereof, wherein the nanoparticle comprises albumin cross-linked in mesh structure, wherein the mesh structure encapsulates a therapeutic nucleic acid, wherein the therapeutic nucleic acid is an inhibitor of STAT3. In some embodiments, the nanoparticle further comprises a cell penetrating peptide. In some embodiments, the cell penetrating peptide is iRGD. In some embodiments, the cross-linked albumin is present at greater than or equal to about 50% by weight to less than or equal to about 95% by weight, and wherein a crosslinking agent is present at greater than or equal to about 5% by weight to less than or equal to about 50% by weight. In some embodiments, the therapeutic nucleic acid is siRNA against STAT3. In some embodiments, the mesh structure has an average linear mesh size of greater than or equal to about 1 nm to less than or equal to about 4 nm.

In another aspect, the invention features a method of generating an anti-tumor humoral immune response by administering an effective amount of a nanoparticle, or composition thereof, wherein the nanoparticle comprises albumin cross-linked in mesh structure, wherein the mesh structure encapsulates a therapeutic nucleic acid, wherein the therapeutic nucleic acid is an inhibitor of ATG7. In some embodiments, the nanoparticle further comprises a cell penetrating peptide. In some embodiments, the cell penetrating peptide is iRGD. In some embodiments, the cross-linked albumin is present at greater than or equal to about 50% by weight to less than or equal to about 95% by weight, and wherein a crosslinking agent is present at greater than or equal to about 5% by weight to less than or equal to about 50% by weight. In some embodiments, the therapeutic nucleic acid is siRNA against ATG7. In some embodiments, the mesh structure has an average linear mesh size of greater than or equal to about 1 nm to less than or equal to about 4 nm.

In various aspects, the current technology further provides a pharmaceutical composition including the nanoparticle.

In various aspects, the current technology yet further provides a method of making a nanoparticle, the method including jetting a liquid including a water-soluble protein having an average molecular weight of greater than or equal to about 8 kDa and less than or equal to about 700 kDa and water through a nozzle; and exposing the liquid to an electric field sufficient to solidify the liquid and form the nanoparticle defining a mesh structure having an average linear mesh size of greater than or equal to about 1 nm to less than or equal to about 4 nm.

In one aspect, the liquid further includes a crosslinking agent and during the exposing, the water-soluble protein is at least partially cross-linked.

In one aspect, the at least partially cross-linked water-soluble protein defines a mesh structure having an average linear mesh size of greater than or equal to about 1 nm to less than or equal to about 4 nm.

In one aspect, the electric field is formed by applying a potential difference between at least two electrodes from about 0.1 kV to about 25 kV.

In one aspect, the liquid further includes an additive selected from the group consisting of a therapeutic active ingredient, an imaging agent, a targeting moiety, and a combination thereof, wherein the additive is incorporated into the nanoparticle.

In one aspect, the additive is a therapeutic active ingredient that is a biomolecule.

In one aspect, the biomolecule is a nucleic acid (e.g., a therapeutic nucleic acid).

In one aspect, the biomolecule is DNA.

In various aspects, the current technology also provides a nanoparticle including a cross-linked water-soluble protein having an average molecular weight of greater than or equal to about 8 kDa to less than or equal to about 700 kDa and having disulfide bonds, wherein the nanoparticle is substantially free of a distinct crosslinking agent.

In one aspect, the cross-linked water-soluble protein defines a mesh structure.

In one aspect, the cross-linked water-soluble protein is selected from the group consisting of albumin, human serum albumin, ovalbumin, bovine serum albumin, transferrin, catalase, horseradish peroxidase, glucose oxidase, hemoglobin, IgG, enzymes, transport proteins, storage proteins, antibodies, aptamers, chemokines, hormonal proteins, polypeptides, and combinations thereof.

In some embodiments, the water soluble protein is albumin and the therapeutic active ingredient is a nucleic acid (e.g., DNA or RNA, such as siRNA, siRNA against STAT3, and siRNA against ATG7). In some embodiments, the current technology provides a method of treating a subject having a glioblastoma, the method including administering to the subject a nanoparticle in an effective amount to treat the glioblastoma, wherein the nanoparticle includes a cross-linked albumin mesh structure and a nucleic acid (e.g., DNA or RNA, such as siRNA, siRNA against STAT3, and siRNA against ATG7).

In one aspect, the nanoparticle further includes one or more of a therapeutic active ingredient, an imaging agent, a biomolecule, and a targeting moiety.

In various aspects, the current technology provides a method of treating a subject having a cancer, the method including administering to the subject the nanoparticle in an effective amount to treat the cancer. In some embodiments, the cancer is glioblastoma. In some embodiments, the cancer is diffuse astrocytoma.

In various aspects, the current technology further provides a pharmaceutical composition including the nanoparticle.

In various aspects, the current technology yet further provides a method of making a nanoparticle, the method including jetting a liquid including a water-soluble protein having an average molecular weight of greater than or equal to about 8 kDa to less than or equal to about 700 kDa and including disulfide bonds through a nozzle; and exposing the liquid to an electric field sufficient to cross-link and solidify the liquid and form the nanoparticle that is substantially free of a distinct crosslinking agent.

In one aspect, the water-soluble protein defines a mesh structure having an average linear mesh size of greater than or equal to about 1 nm to less than or equal to about 4 nm.

In one aspect, the electric field is formed by applying a potential difference between at least two electrodes from about 0.1 kV to about 25 kV.

In one aspect, the liquid further includes an additive selected from the group consisting of a therapeutic active ingredient, an imaging agent, a targeting moiety, and a combination thereof, wherein the additive is incorporated into the nanoparticle.

In one aspect, the therapeutic active ingredient is a biomolecule.

In one aspect, the biomolecule is a nucleic acid.

In one aspect, the biomolecule is DNA.

In one aspect, the water-soluble protein is selected from the group consisting of albumin, human serum albumin, ovalbumin, bovine serum albumin, transferrin, hemoglobin, catalase, horseradish peroxidase, glucose oxidase, IgG, an enzyme, a transport protein, a storage protein, an antibody, an aptamer, a chemokines, a hormonal protein, a polypeptide, and a combination thereof.

In various aspects, the current technology provides a multicompartmental nanoparticle including a first compartment defining at least a portion of an exposed surface of the multicompartmental nanoparticle and including a first composition having a water-soluble polymer having an average molecular weight of greater than or equal to about 8 kDa and less than or equal to about 700 kDa; and at least one additional compartment defining at least a portion of an exposed surface and including at least one additional composition distinct from the first composition.

In one aspect, the multicompartmental nanoparticle further includes a crosslinking agent conjugated to the water-soluble protein in the first compartment.

In one aspect, the water-soluble protein is present at greater than or equal to about 50% by weight to less than or equal to about 95% by weight and the crosslinking agent is present at greater than or equal to about 5% by weight to less than or equal to about 50% by weight.

In one aspect, prior to reacting with the water-soluble protein, the crosslinking agent includes a reactive group selected from the group consisting of an alkenyl group, an alkynyl group, a maleimide group, an active ester group, an anhydride group, an N-succinimidyl group, a triflate group, and combinations thereof.

In one aspect, the multicompartmental nanoparticle further includes one or more of a therapeutic active ingredient, an imaging agent, and a targeting moiety.

In one aspect, the multicompartmental nanoparticle includes a therapeutic active ingredient, which is a biomolecule.

In one aspect, the biomolecule is a nucleic acid.

In one aspect, the biomolecule is DNA.

In one aspect, the water-soluble protein is selected from the group consisting of albumin, ovalbumin, mucin, transferrin, insulin, lysozyme, hemoglobin, collagen, catalase, horseradish peroxidase, glucose oxidase, and a combination thereof.

In one aspect, the water-soluble protein is a first water soluble protein and the at least one additional compartment includes a second water-soluble protein.

In one aspect, the second water-soluble protein is selected from the group consisting of albumin, ovalbumin, mucin, transferrin, insulin, lysozyme, hemoglobin, collagen, catalase, horseradish peroxidase, glucose oxidase, and a combination thereof.

In various aspects, the current technology further provides a method of treating a subject having a cancer, the method including administering to the subject the multicompartmental nanoparticle in an effective amount to treat the cancer. In some embodiments, the cancer is glioblastoma. In some embodiments, the cancer is diffuse astrocytoma.

In various aspects, the current technology yet further provides a pharmaceutical composition including the multicompartmental nanoparticle.

In various aspects, the current technology provides a nanoparticle including a cross-linked water-soluble protein having an average molecular weight of greater than or equal to about 8 KDa and less than or equal to about 700 kDa and a therapeutic active ingredient.

In one aspect, the therapeutic active ingredient is selected from the group consisting of DNA, RNA, plasmids, short interfering sequence of double stranded RNA (siRNA), messenger RNA (mRNA), transfer RNA, ribosomal RNA, small nuclear RNA, single stranded DNA, CRISPR CAS-9, aptamers, antibodies, peptides, targeting molecules, vitamins, and combinations thereof.

In one aspect, the nanoparticle further includes a cross-linking agent conjugated to the water-soluble protein.

In one aspect, the cross-linked water soluble protein is present at greater than or equal to about 50% by weight to less than or equal to about 95% by weight and the cross-linking agent is present at greater than or equal to about 5% by weight to less than or equal to about 50% by weight.

In one aspect, prior to reacting with the water-soluble protein, the crosslinking agent includes a reactive group selected from the group consisting of an alkenyl group, an alkynyl group, a maleimide group, an active ester group, an anhydride group, an N-succinimidyl group, a triflate group, and a combination thereof.

In one aspect, the nanoparticle further includes one or more of an imaging agent, an additional biomolecule, and a targeting moiety.

In one aspect, the therapeutic active ingredient is selected from the group consisting of a drug, a steroid, and combinations thereof.

In one aspect, the drug is selected from the group consisting of: paclitaxel, cis-platin, doxorubicin, and combinations thereof.

In one aspect, the therapeutic active ingredient is selected from the group consisting of: an antibody, an aptamer, a chemokine, a peptide drug, and combinations thereof.

In one aspect, the water-soluble protein is selected from the group consisting of albumin, ovalbumin, mucin, transferrin, insulin, lysozyme, hemoglobin, collagen, catalase, horseradish peroxidase, glucose oxidase, and a combination thereof.

Further areas of applicability will become apparent from the description provided herein. The description and specific examples in this summary are intended for purposes of illustration only and are not intended to limit the scope of the present disclosure.

DRAWINGS

The drawings described herein are for illustrative purposes only of selected embodiments and not all possible implementations, and are not intended to limit the scope of the present disclosure.

Figures 5A, 5B, 5C, 5D:
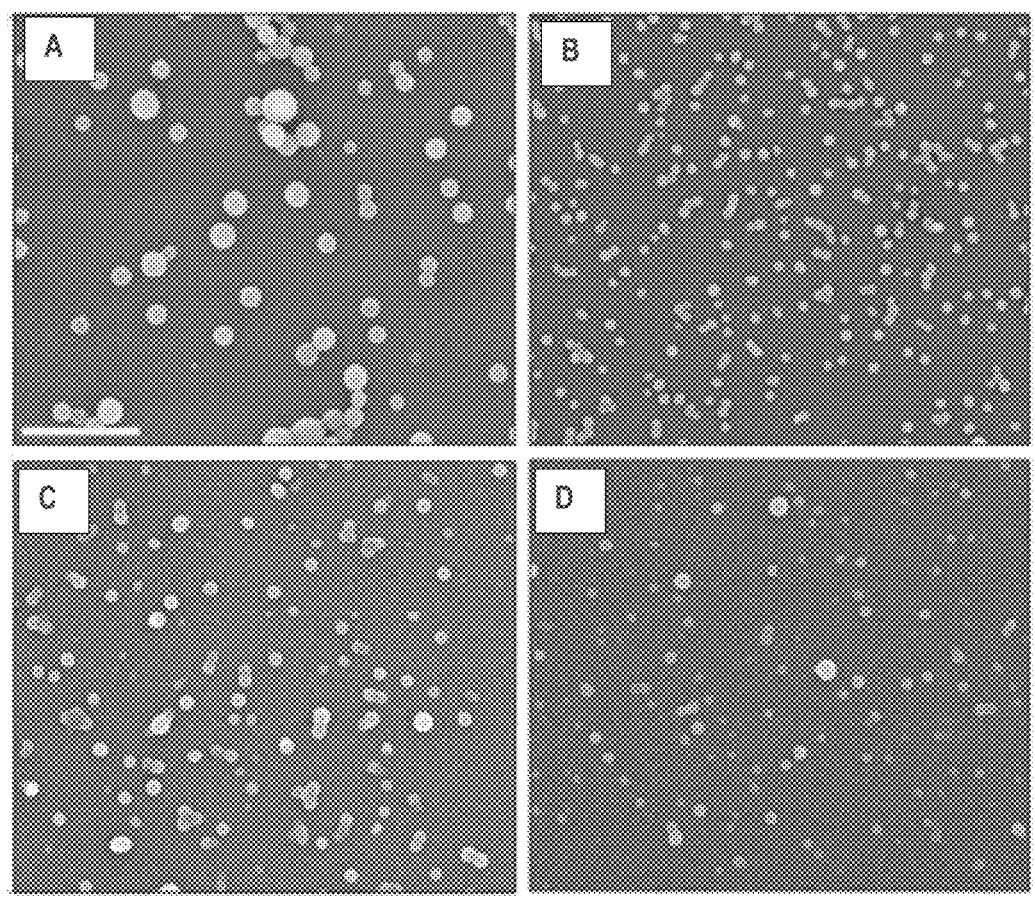

FIGS. 5A-5D show SEM images of different ovalbumin nanoparticles formed via an electrohydrodynamic jetting process in accordance with certain aspects of the present disclosure. FIG. 5A shows an ovalbumin nanoparticle with 10 w/w % NHS-PEG-NHS crosslinker (MW=2000 g/mol (2 k XL)). Scale bar is 1 μm and applies to all figures. FIG. 5B shows an ovalbumin nanoparticle with 30 w/w % 2 k XL. FIG. 5C shows an ovalbumin nanoparticle with 50 w/w % 2 k XL fabricated with 80:20 vol. % ethylene glycol/water. FIG. 5D shows 5 w/w % 20 k XL fabricated with 40:60 vol. % ethylene glycol/water.

Figures 6A, 6B, 6C, 6D:
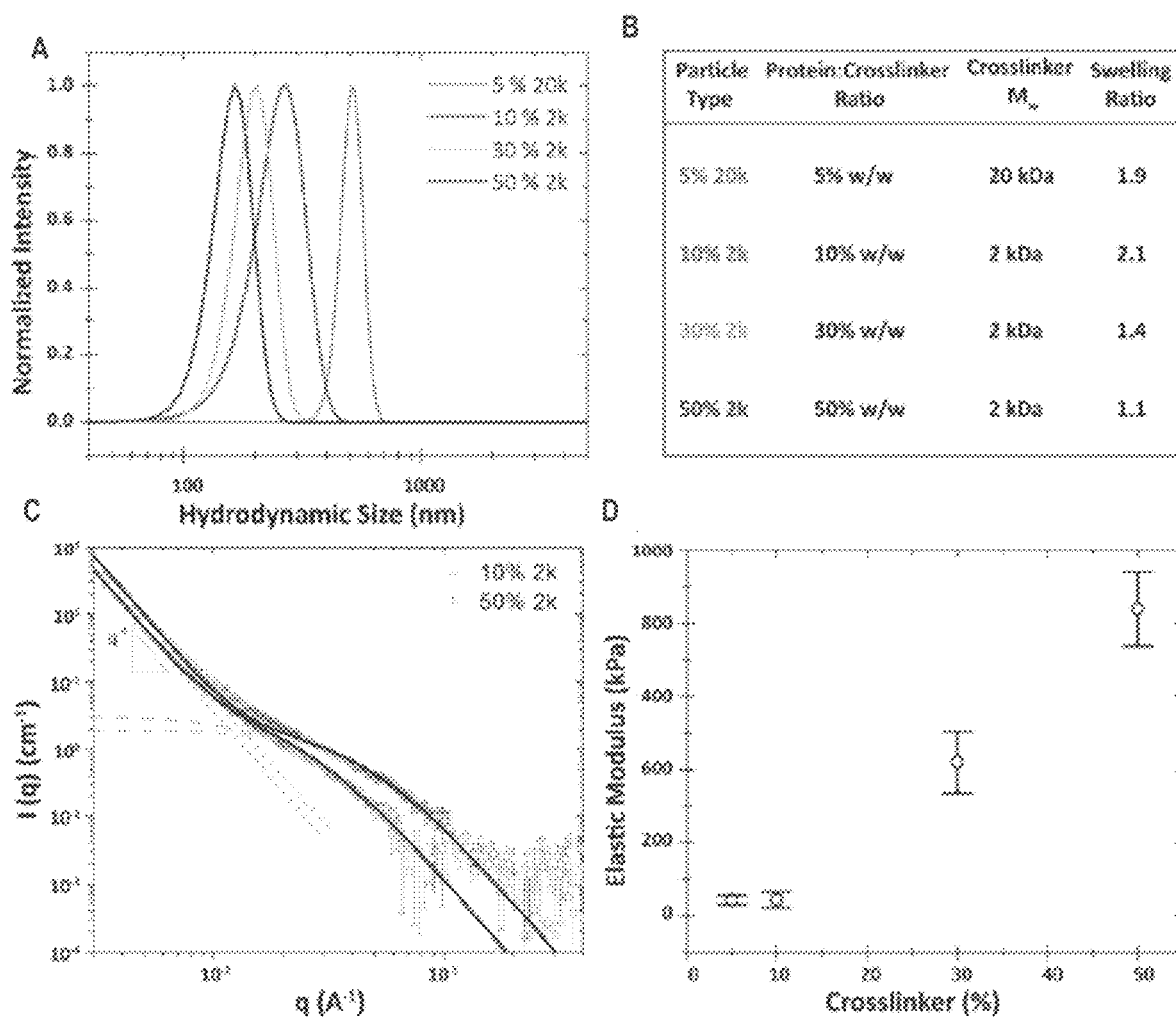

FIGS. 6A-6D. FIG. 6A shows size distributions of the ovalbumin (OVA) protein-based particles (pNPs) in FIGS. 5A-5D. The size distributions are obtained by measuring NP diameters using ImageJ. The size of hydrated pNPs is measured using DLS after NP collection and dispersion in PBS buffer. FIG. 6B is a table with parameters/conditions for electrospraying of the OVA pNPs. FIG. 6C is SANS data and fits for OVA pNPs with 10% and 50% XL. OVA pNPs are dispersed in $D_2O$ at 2 mg/mL. Data are fitted using the Debye-Anderson-Brumberger (DAB) model. FIG. 6D shows measured Young's modulus as a function of the pNP crosslinker amount. Data are obtained by fitting the force-distance profiles obtained from AFM measurements using the Hertz model for a conical indenter.

Figures 7A, 7B, 7C, 7D, 7E, 7F, 7G:
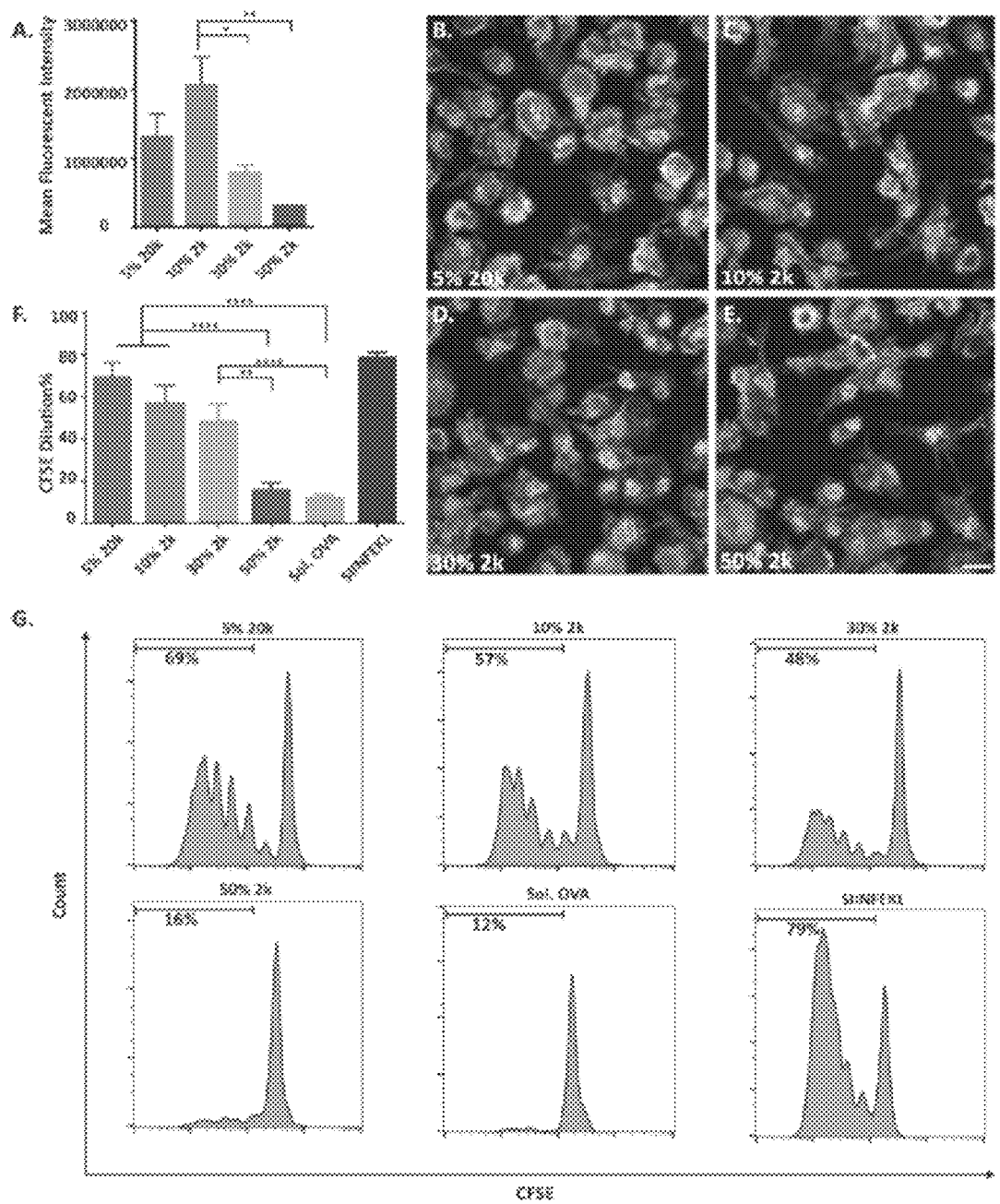

FIGS. 7A-7G. FIG. 7A shows uptake of fluorescently labeled ovalbumin (OVA) protein-based particles (pNPs) by bone marrow-derived dendritic cells (BMDCs). FIGS. 7B-7E show quantitative uptake data (MFI values) obtained by flow cytometry for ovalbumin nanoparticles with 5 w/w % NHS-PEG-NHS crosslinker, 10 w/w % NHS-PEG-NHS crosslinker, 30 w/w % NHS-PEG-NHS crosslinker, and 50% w/w % NHS-PEG-NHS crosslinker. Uptake is further visualized by confocal microscopy. BMDCs are incubated with OVA pNPs (10 μg/mL) for 24 hours. For flow cytometry, BMDCs are stained for DC marker CD11c+ using anti-CD11c+PE-Cy7; they are also stained with DAPI. For confocal microscopy, actin is stained with phalloidin488 and nuclei are stained with DAPI. The data represent the mean±SEM from triplicates of 3 experiments. The data are analyzed by one-way ANOVA, followed by Tukey's post-test, using GraphPad 6.0. A P-value of <0.05 is considered statistically significant (*P<0.05, P<0.01, *P<0.001; ****P<0.0001); P-values of >0.05 are considered not significant (ns). FIG. 7F shows OVA pNP-treated BMDCs induce proliferation of OT-I CD8+ cells. A percentage of proliferated OT-I CD8+ cells after co-culture with BMDCs incubated with 10 μg/mL OVA pNPs (5% 20 k XL, 10% 2 k XL, 30% 2 k XL, 50% 2 k XL) are shown. FIG. 7G shows representative flow cytometry histograms of FIG. 7F. The data represent the mean±SEM from triplicates of three experiments. The data are analyzed by linear-mixed model with Tukey's post-test using RStudio software. A P-value of <0.05 is considered statistically significant (*P<0.05, P<0.01, *P<0.001; ****P<0.0001); P-values of >0.05 are considered not significant (ns).

Figure 8A:
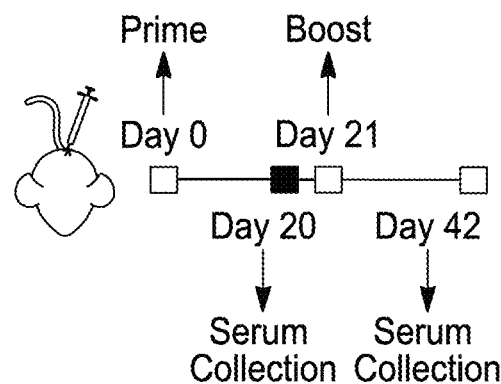
Figure 8B:
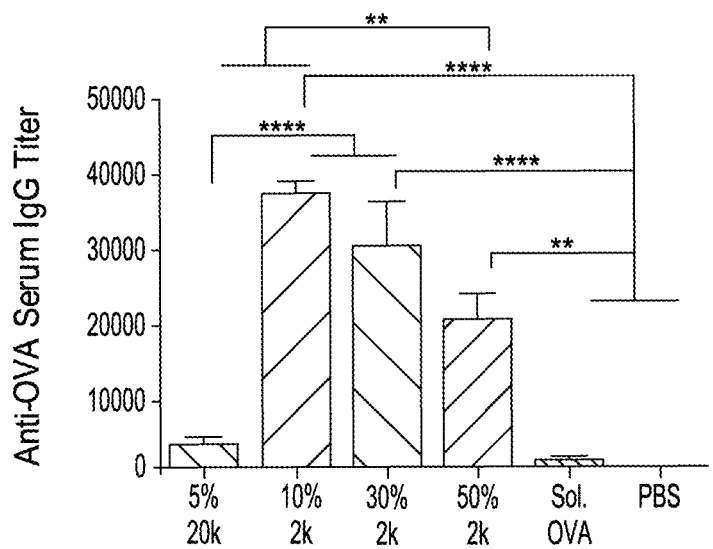
Figure 8C:
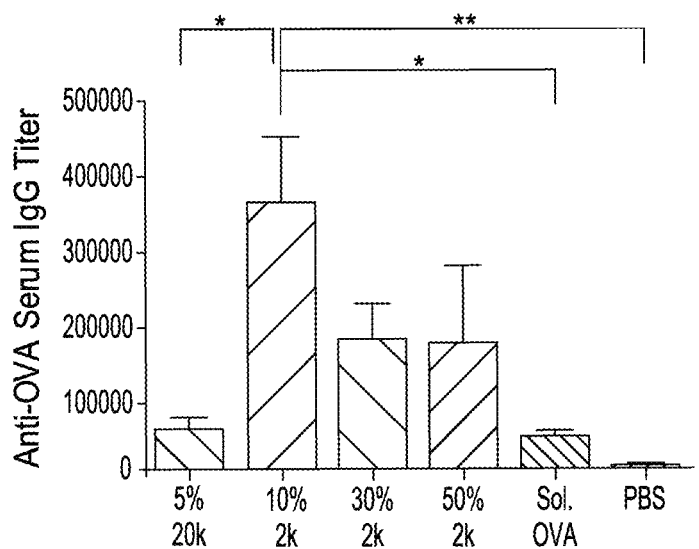
Figure 8D:
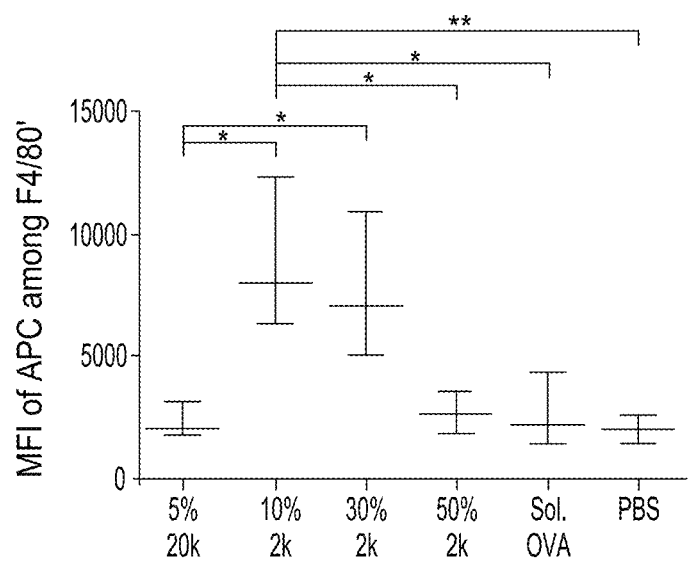
Figure 8E:
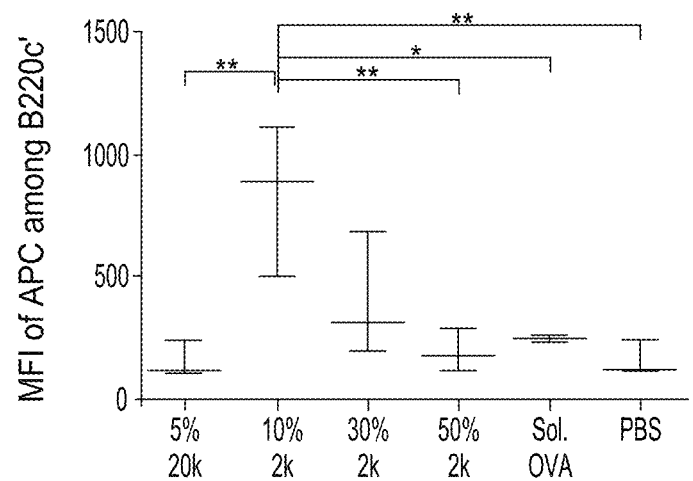
Figure 8F:
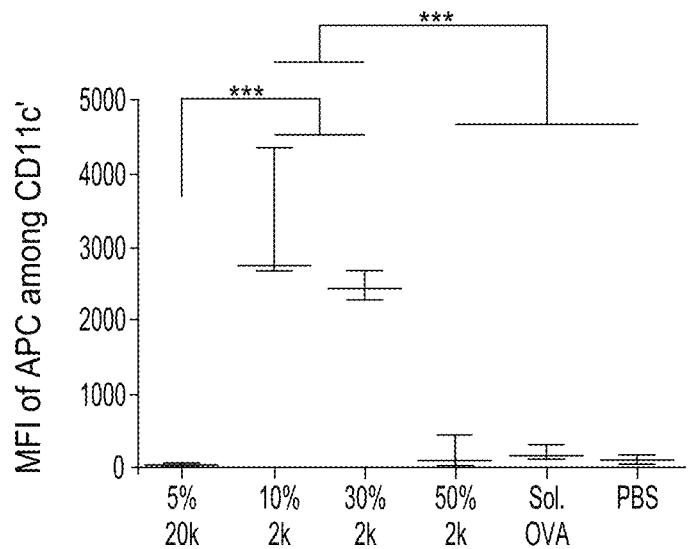

FIGS. 8A-8F. FIGS. 8A-8F show humoral immune responses elicited by polymerized OVA pNPs in vivo. FIG. 8A show vaccine doses and regimen. Naïve C57BL/6 mice are injected with OVA pNPs and soluble CpG subcutaneously at the tail base on Day 0 (prime immunization) and 21 (boost immunization). Data are analyzed using multiple t-test. P<0.05 is considered statistically different (*P<0.05, P<0.01, *P<0.001, and ****P<0.0001); P>0.05 is considered not significant. Serum anti-OVA IgG titers are measured on day 20 (shown in FIG. 8B—prime response) and day 28 (FIG. 8C—boost response). The data are fitted by logarithmic regression. The titer is calculated by solving for the inverse dilution factor resulting in an absorbance value of 0.5. Data represent mean±SEM (n=5). Groups are compared using one-way ANOVA with Tukey's post-test. P<0.05 is considered statistically different (*P<0.05, P<0.01, *P<0.001, and ****P<0.0001). P>0.05 is considered not significant. Delivery of pNPs to dLNs: MFI of AlexaFluor 647 associated with OVA NPs among (FIG. 8D) F4/80+ macrophages, (FIG. 8E) B220+ B cells and (FIG. 8F) CD11c+ DCs obtained from a single cell suspension from draining lymph nodes. Groups are compared using one-way ANOVA with Tukey's post-test. P<0.05 is considered statistically different (*P<0.05, P<0.01, *P<0.005). P>0.05 is considered not significant.

Figure 9A:
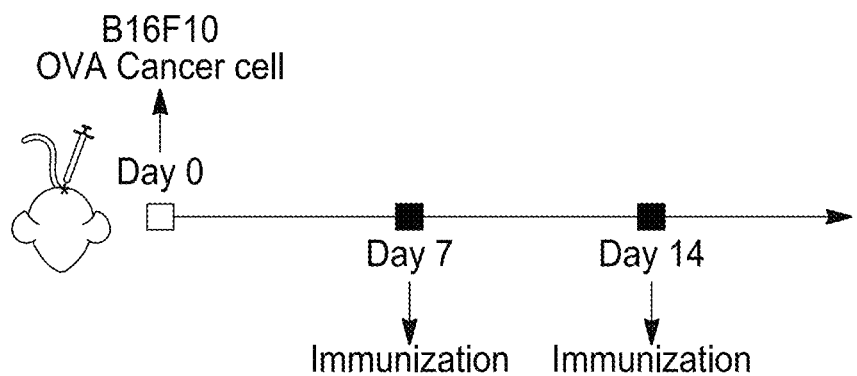
Figure 9B:
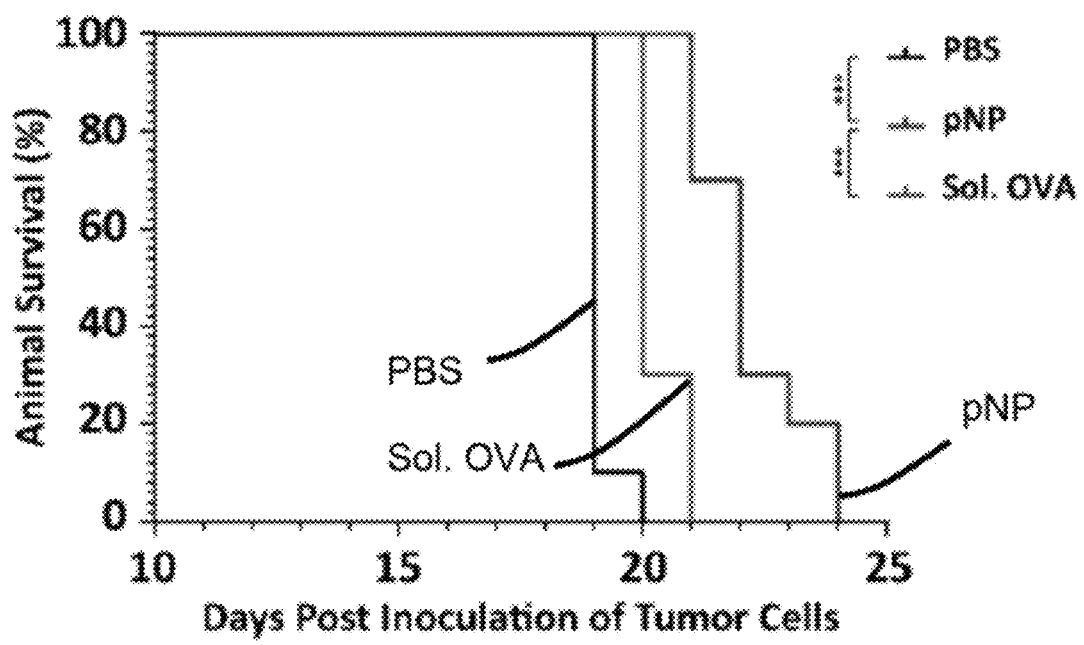

FIGS. 9A-9B. FIGS. 9A-9B show therapeutic effect of OVA pNPs. In FIG. 9A, a vaccine doses and regimen for a murine model is shown. FIG. 9B shows animal survival. C57BL/6 mice are inoculated subcutaneously with 1×105 B16F10-OVA cells on day 0. On days 7 and 14, mice are treated with indicated formulations (OVA pNP, soluble OVA, PBS) containing 10 μg/dose OVA and 15 μg/dose CpG (100 μL dose). Data represent mean±SEM (n=10). Groups are compared using Kaplan-Meier estimator analysis. P<0.05 is considered statistically different (*P<0.05). P>0.05 is considered not significant.

Figures 10A, 10B, 10C, 10D, 10E, 10F, 10G:
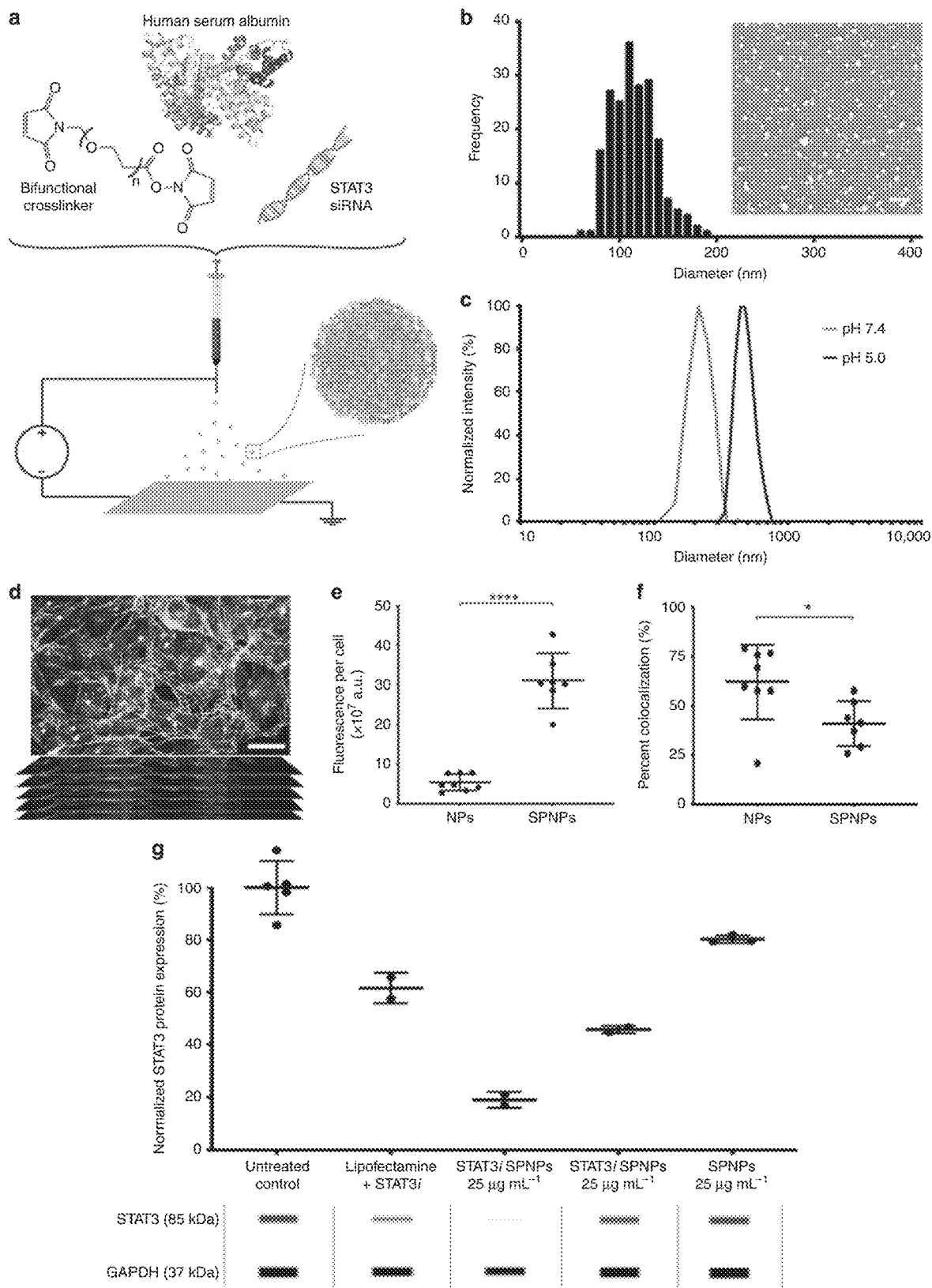

FIGS. 10A-10G show that STAT3 expression is effectively silenced in vitro by siRNA-loaded SPNPs. FIG. 10A is a schematic of the jetting formulation for crosslinked, STAT3i-loaded, iRGD-conjugated, targeted albumin NPs (STAT3iSPNPs). FIG. 10B shows particle size characterization and analysis was performed using scanning electron microscopy (SEM). Average particle diameter, 115±23.4 nm. Scale bar is 1 μm. FIG. 10C shows that particles undergo swelling in their hydrated state and further swell at reduced pH. Average diameters: pH 7.4, 220±26.1 nm. pH 5.0, 396±31.2 nm. FIG. 10D is a representative confocal z-stack image of cells cultured in the presence of SPNPs (blue=nucleus, green=actin, yellow=lysosomes, red=SPNPs). Composite images of cells incubated with SPNPs (with and without iRGD) were collected from a single independent experiment to study intracellular particle fate. Scale bar=30 μm. FIGS. 10E and 10F show quantification of particle uptake and lysosomeparticle colocalization. FIG. 10E shows local release of iRGD from SPNPs increases particle uptake in GL26 glioma cells by greater than five-fold (*$p<0.0001$). FIG. 10F** shows that internalized SPNPs colocalize with lysosomes to a lesser extent than untargeted particles (*$p=0.0235$). Data are presented as mean values±s.d. (synthetic protein nanoparticles (SPNPs) n=7, NPs n=8, independent composite z-stack images; two-tailed unpaired t-test). FIG. 10G shows that STAT3 siRNA-loaded SPNPs significantly reduce in vitro expression of target protein in GL26 glioma cells compared to untreated and empty particle control groups. Data are presented as mean values±s.d. (SPNPs, n=3; Lipofectamine+STAT3i, STAT3i SPNPs (25 and 2.5 μgmL−1, n=2 biological replicates). Representative bands obtained with the Protein-Simple Wes instrument for both STAT3 (siRNA target protein) and GAPDH (loading control) are displayed for each experimental group.

Figure 11:
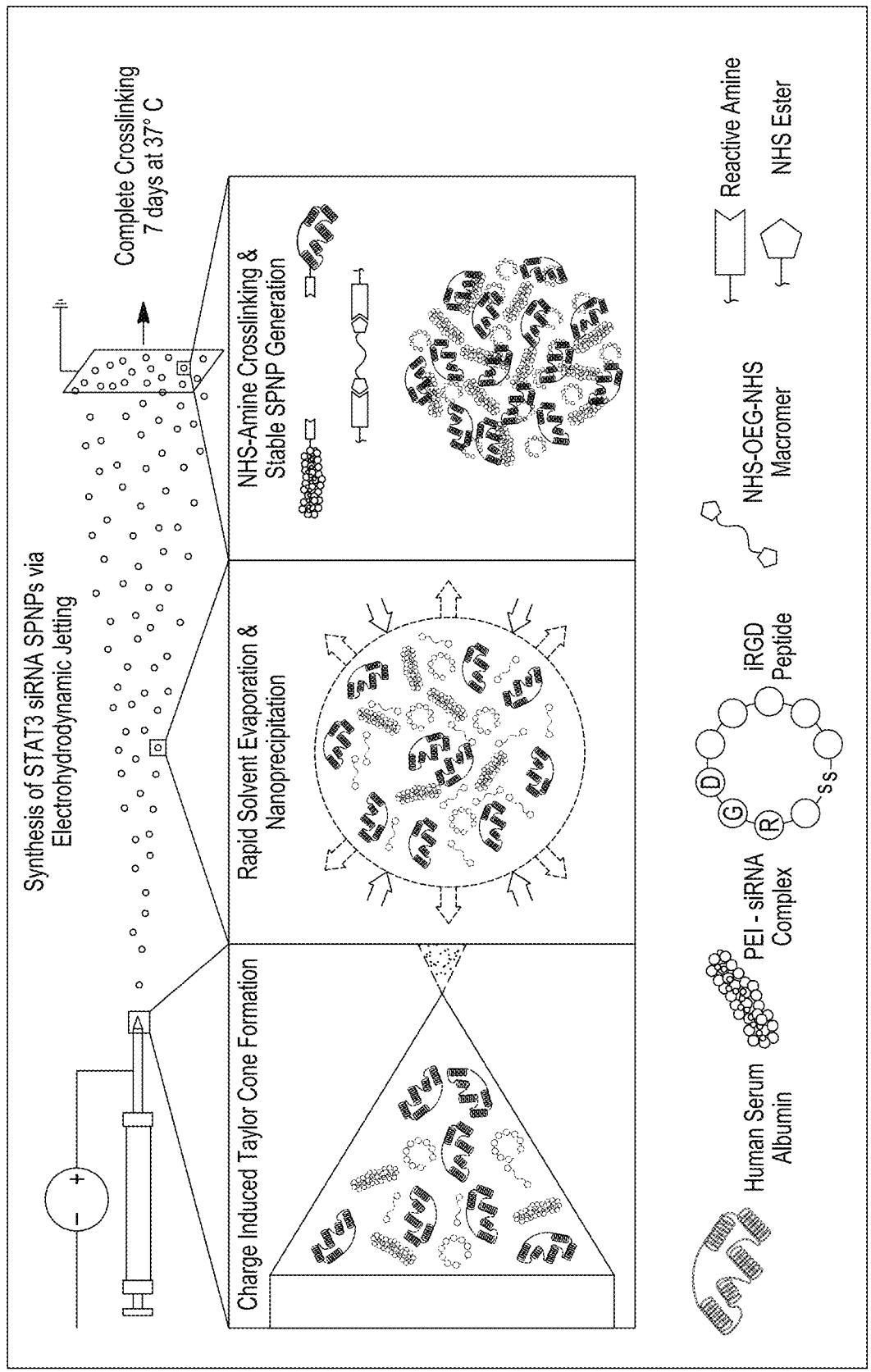

FIG. 11 is a schematic showing the synthesis of STAT3i SPNPs. Electrohydrodynamic (EHD) jetting uses a dilute solution of all components to be incorporated into the ultimate protein nanoparticle (here: HSA, OEG macromer, STA3i-PEI complex, and iRGD in an aqueous system). Using controlled flow through a single capillary, the application of an electric field distorts the droplet to form a stable Taylor Cone from which a jet of charged droplets emanates. Once atomized, rapid evaporation of the solvent induces nearly instantaneous nanoprecipitation of all non-volatile components to form solid protein nanoparticles. The bifunctional OEG macromer covalently links the protein and PEI units through reactive amine groups, resulting in a continuous network. The STAT3i is complexed to the PEI through electrostatic interactions, while the iRGD is encapsulated.

Figure 12:
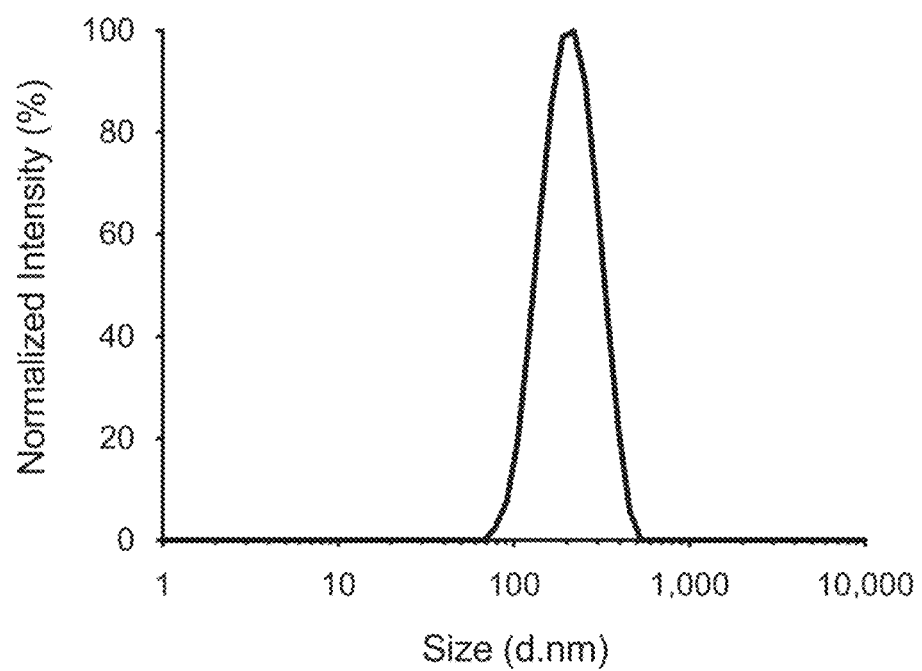

FIG. 12 is a graph showing that SPNPs are stable at physiological conditions. Characterization of SPNPs size was measured by dynamic light scattering (DLS) following the collection process and storage in PBS (pH 7.4) at 4° C. Particles were observed to swell with an increase in average size compared to their dry, crosslinked state. Average diameter=220 nm. No change was observed in average particle diameter over a period of 1 month at the above conditions.

Figure 13:
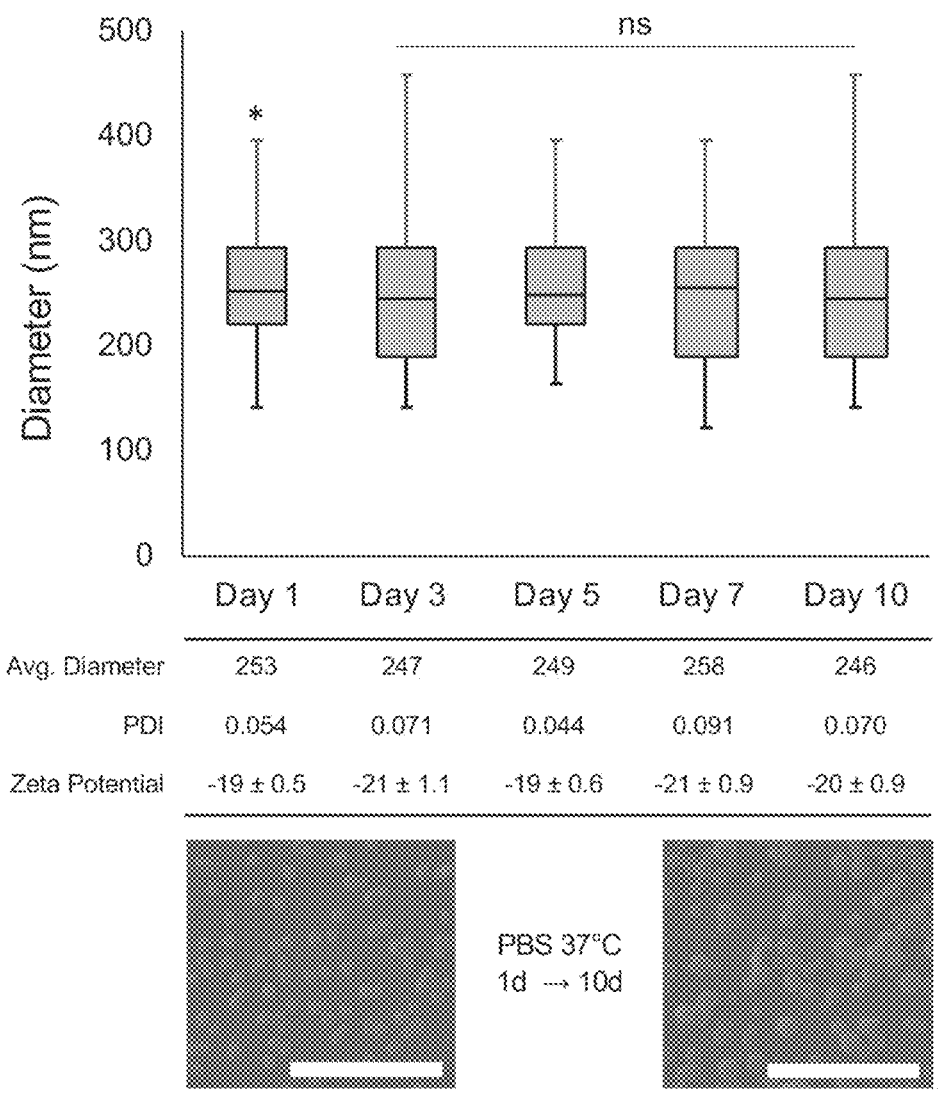

FIG. 13 shows that SPNPs remain stable in solution under relevant physiological conditions. (Top) After a single day in PBS at 37° C., SPNPs show no significant change in particle size as measured by dynamic light scattering (DLS). Particles appear to both remain intact and do not aggregate under these conditions. Similarly, the polydispersity index (PDI) and zeta potential values remain consistent over the ten day incubation period. Hydrodynamic diameter data from n=5 technical replicates was collected and averaged provided the data met minimum quality standards including a correlation function with a single inflection point. Box and whisker plot data are presented as mean values, first and third quartiles (box) and minimum/maximum values (whiskers), Statistical significance determined with one-way ANOVA and Tukey's multiple comparison test, * $p=0.044$. (Bottom) No change in particle shape or morphology is observed following the incubation at physiological conditions as imaged by scanning electron microscopy (SEM). Scale bars are 2 μm.

Figure 14:
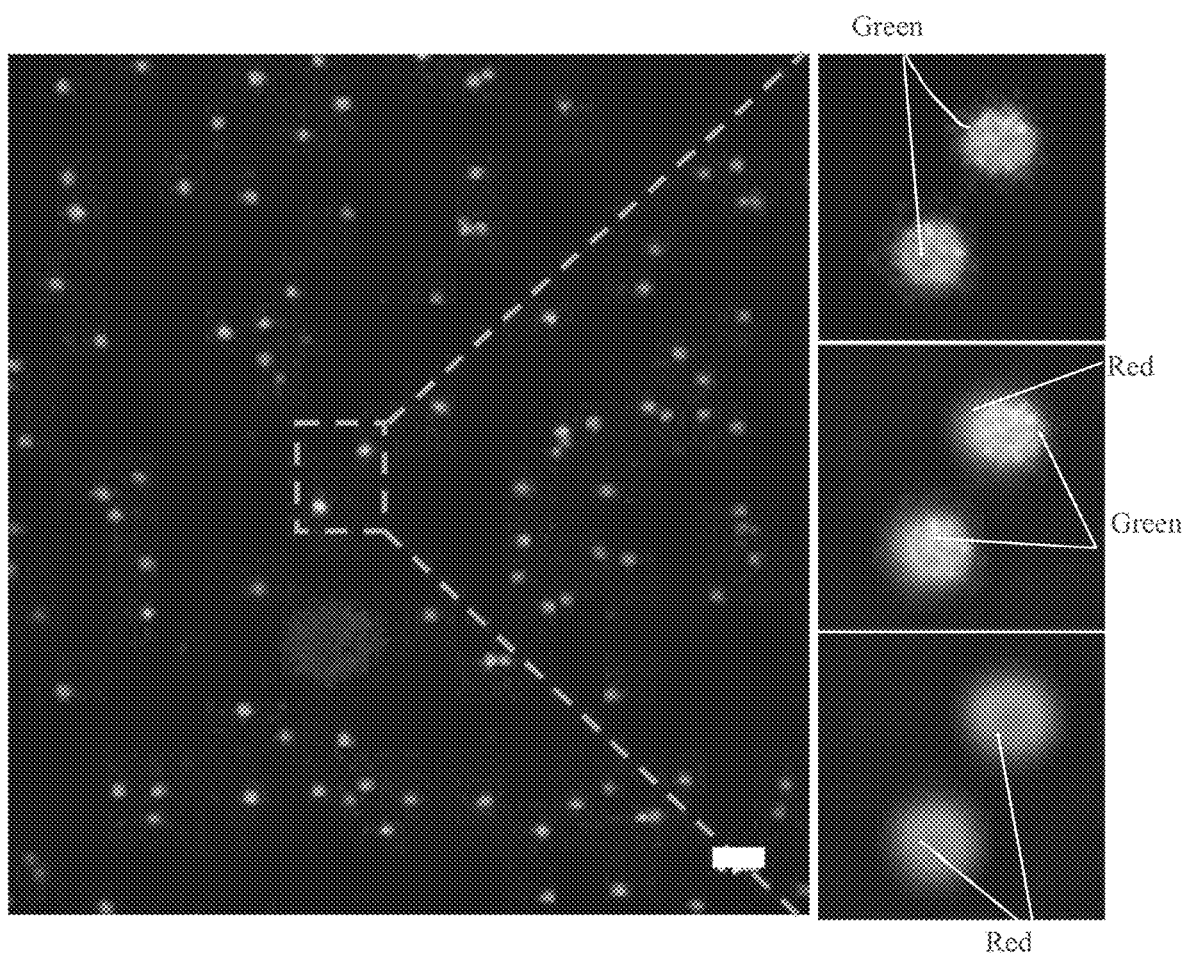

FIG. 14 is a series of fluorescent micrographs showing that SPNPs loaded with Cyanine3-siRNA exhibit controlled siRNA release. Alexa Fluor 488 (green) labeled SPNPs were loaded with a fluorescently (Cy3, red) labeled, scrambled siRNA. Several images were collected across a single prepared sample using super-resolution, Stimulation Emission Depletion (STED) microscopy. Colocalization of the two signals was used to confirmed the encapsulation of siRNA within the particles. Scale bar is 1 μm.

Figure 15:
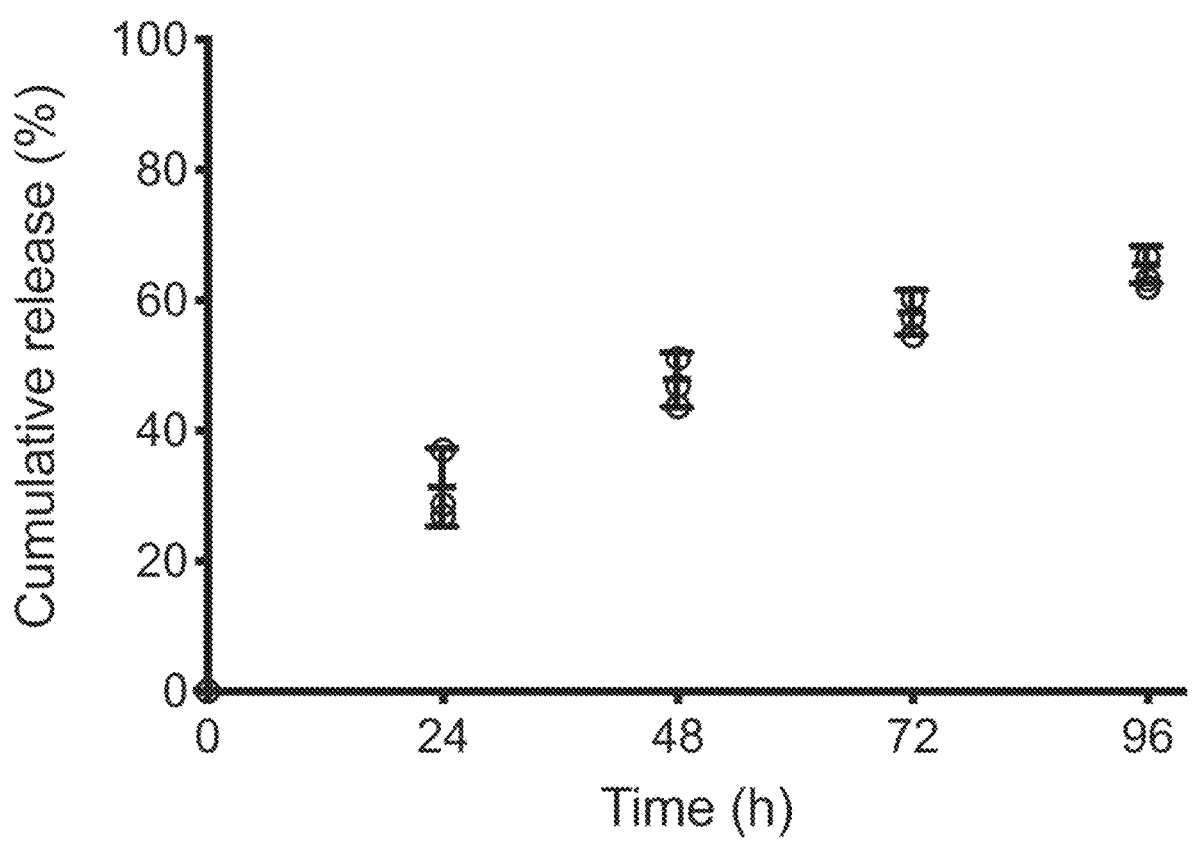

FIG. 15 is a graph showing controlled siRNA release from SPNPs. Loading and subsequent release of Cy3-labeled scrambled siRNA demonstrates a controlled and extended release of incorporated NP cargo. While 60% of the initially encapsulated siRNA is released in the first 96 hours at pH 7.4 and 37° C., continued release is observed for up to 21 days. Complete release confirms a loading efficiency of 96%. Data are presented as mean values±s.d. (n=3 biological replicates).

Figure 16:
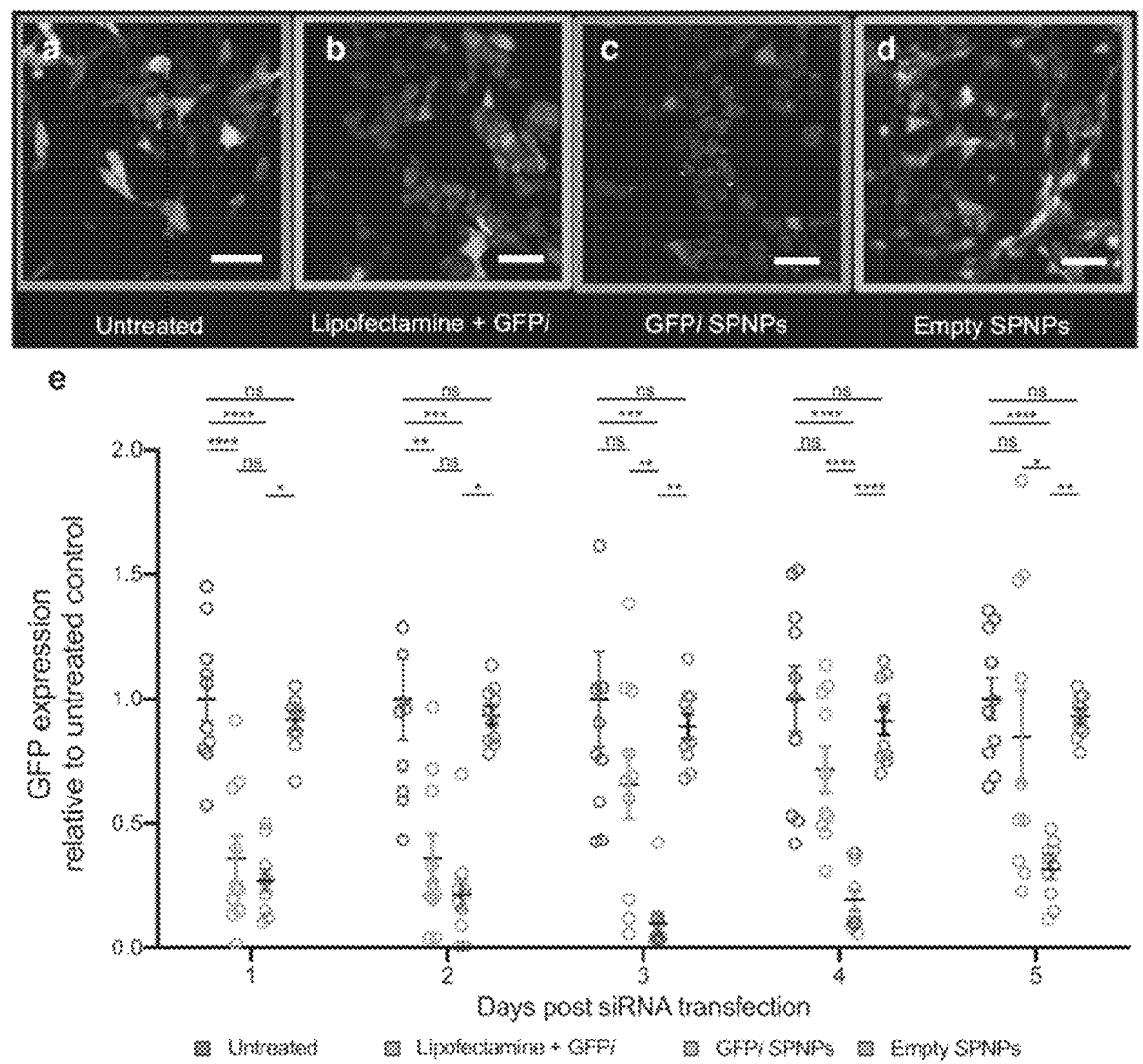

FIG. 16 shows in vitro GFP siRNA-loaded SPNPs reduce target protein expression. (a)-(d) Representative Confocal Scanning Laser Microscopy (CSLM) images of GL26-Cit cells incubated with NPs at 48 h time point. (a) Control group receiving no treatment. (b) Positive control group transfected with GFP siRNA (GFPi) using Lipofectamine 2000. (c) Cells treated with GFPi loaded nanoparticles at a concentration of 25 μg NPs per mL. (d) Cells treated with empty albumin nanoparticles. (e) GFP expression plotted relative to untreated control group over a period of 5 days. A significant and prolonged suppression of target protein is observed in cells that received the siRNA-loaded nanoparticles. A similar knockdown was observed in cells transfected with free siRNA using Lipofectamine at early time points, but a rapid recovery was observed after 48 h. Data are presented as mean values±SEM relative to untreated control (n=10 independent composite images; two-tailed, unpaired t-tests; ** $p<0.0001$, * $p<0.001$, ** $p<0.01$, * $p(1)=0.028$, * $p(2)=0.007$, * $p(5)=0.012$). Scale bars=50 μm.

Figures 17A, 17B:
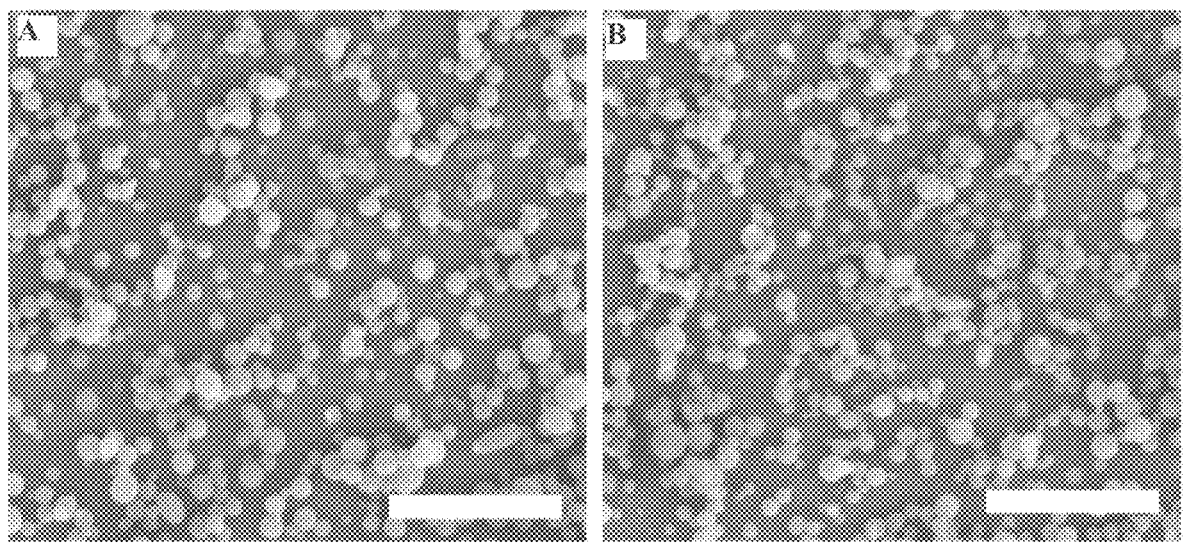

FIGS. 17A-17B show siRNA-loaded SPNPs exhibit similar size and morphology to control SPNPs. The addition of the siRNA/PEI complex to the jetting solution to create siRNA loaded SPNPs (FIG. 17A) results in no significant change in particle size, shape or surface morphology when compared to control (empty) SPNPs (FIG. 17B). When suspended in PBS, no significant difference in zeta potential (siRNA-loaded SPNPs z=−20±1.2, Control SPNPs z=−19±2.9) was observed. Imaging and characterization was performed following the synthesis of particles for all in vitro and in vivo experiments. Across ten independently synthesized batches, similar results were observed when comparing SPNPs with and without siRNA/PEI. Scale bars are 2 μm.

Figure 18:
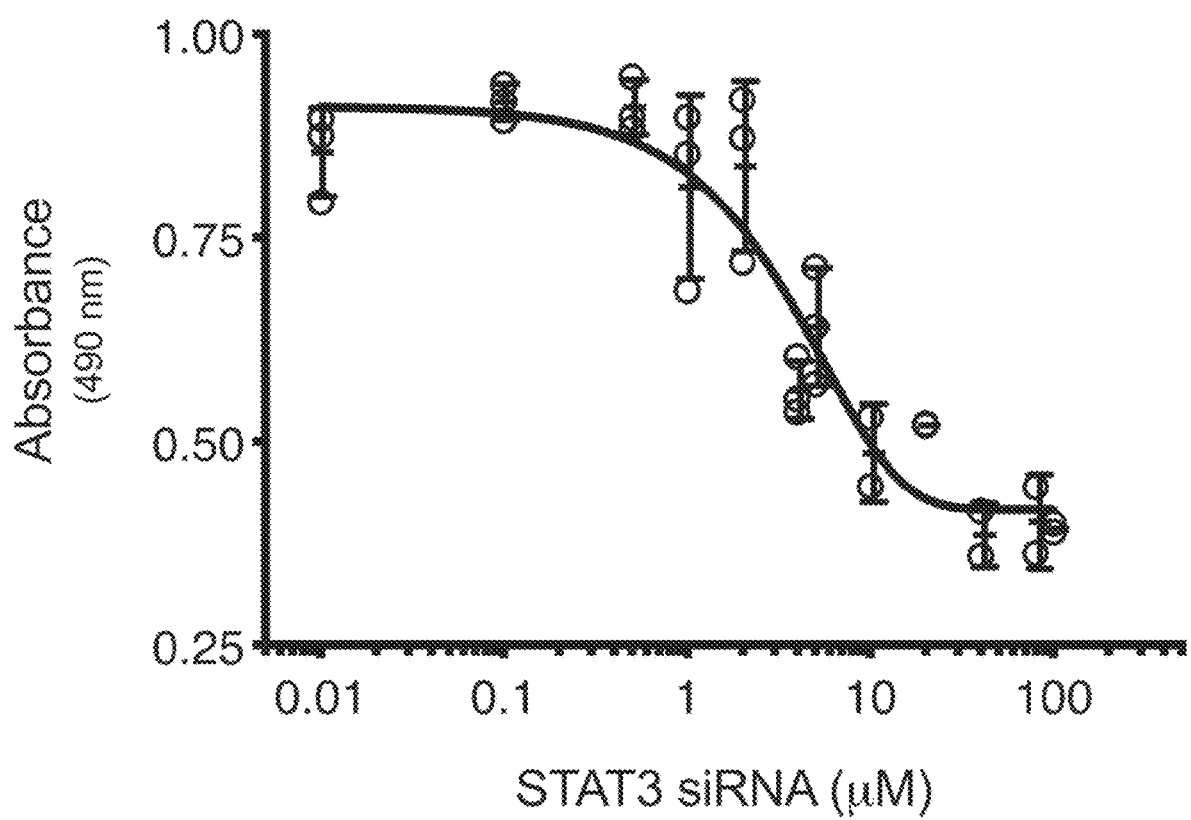

FIG. 18 shows that STAT3 siRNA activity is non-toxic towards glioma cells. Evaluating toxicity associated with free STAT3i, no toxicity was observed at relevant therapeutic concentrations. Concentrations delivered via SPNPs showed a significant silencing ability ($6.5 \times 10^{-4}$ μM), 6,000× less than the IC50 (3.85 μM) for soluble siRNA delivered via traditional transfection. Data are presented as mean values±s.d. (n=3 biological replicates).

Figure 19:
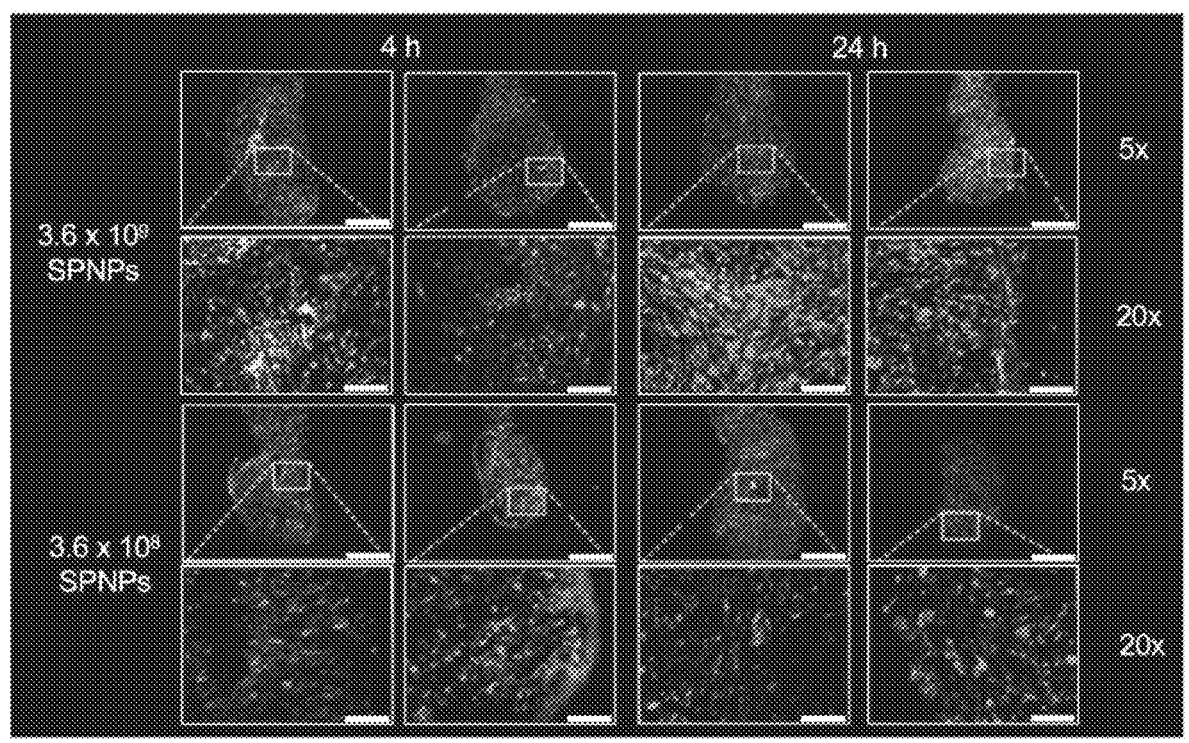

FIG. 19 is a series of photomicrographs showing synthetic protein nanoparticles (SPNPs) distribution in the tumor mass following intracranial injection. Following the implantation of m-Tomato expressing GL26 tumors (red), C57BL/6 mice received 3 μL intracranial injections of either $3.6 \times 10^8$ or $3.6 \times 10^9$ SPNPs (cyan) per mouse. Images suggest that the particles actively and rapidly distribute throughout the tumor mass. Scale bars=150 μm (5×), 600 μm (20×).

Figure 20:
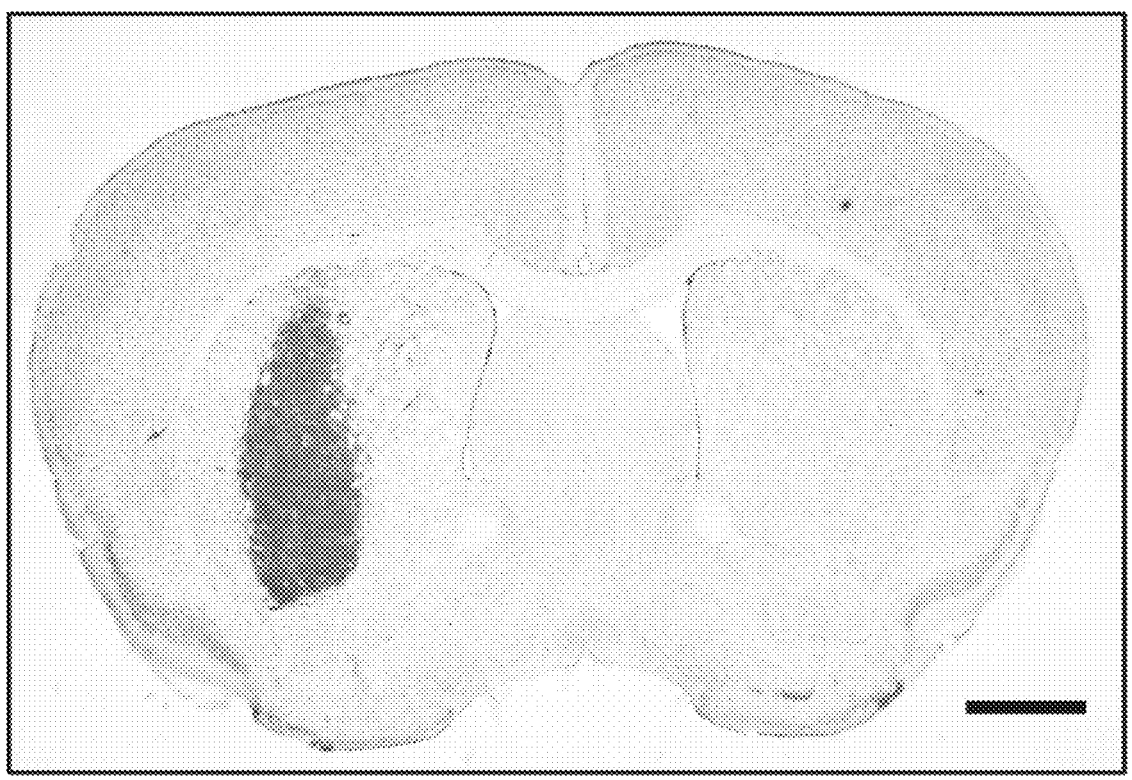

FIG. 20 is an image from which a volume of GL26 GBM at 7 DPI. C57BL/6 mice were implanted with 20,000 GL26 cells orthotopically and brains were processed for Nissl staining at 7 DPI. Staining and imaging was conducted as a single independent experiment. Scale bar=1 mm. Tumor volume=9.61 mm$^3$. Tumor area=$10^7$ pixel units.

Figures 21A, 21B, 21C, 21D, 21E, 21F:
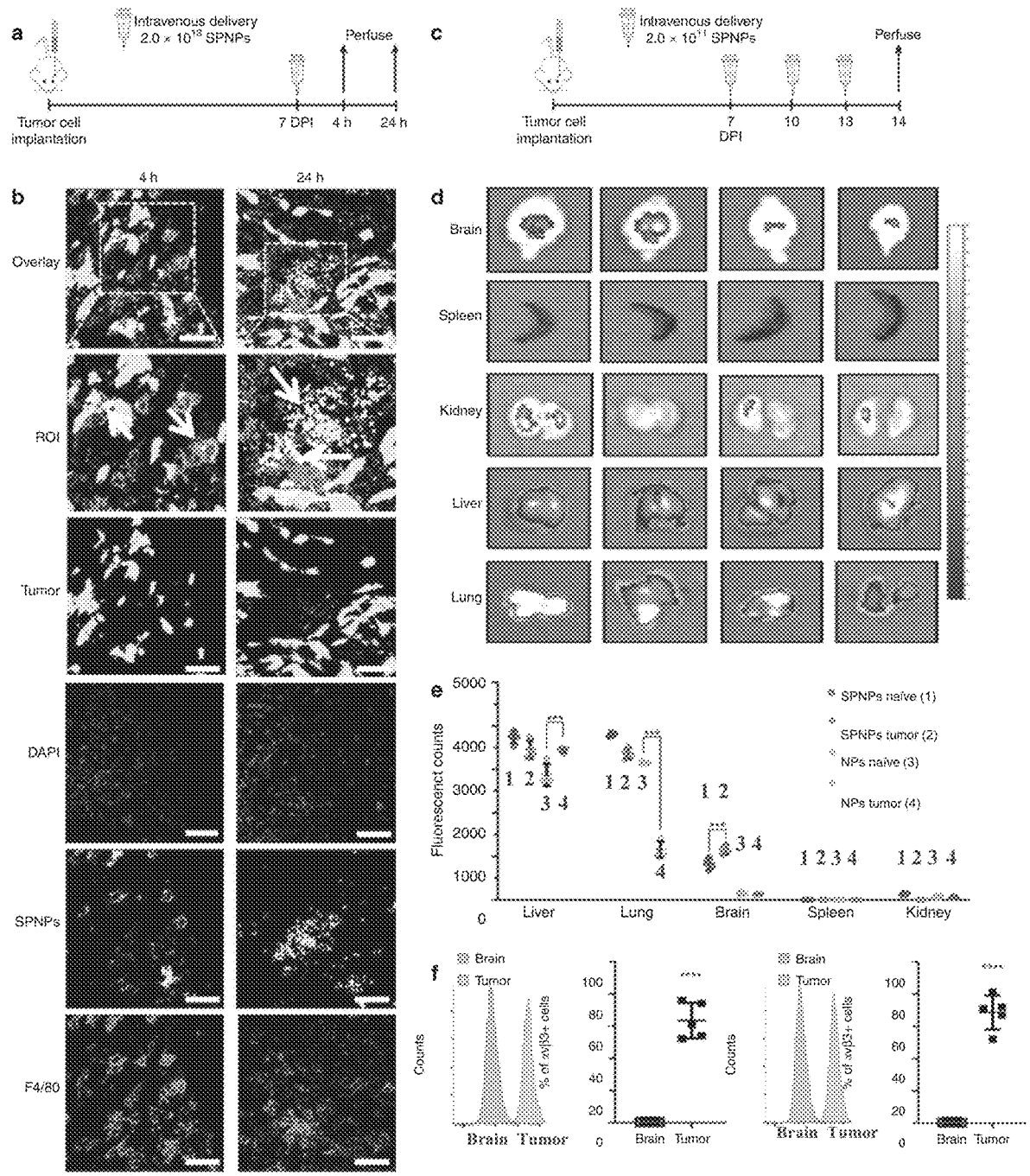

FIGS. 21A-21F show results from in vivo brain targeting and biodistribution of SPNPs. FIG. 21A shows a timeline for the tumor-targeting study. Mice were IV administrated a single dose of $2.0 \times 10^{13}$ SPNPs or empty NPs (no iRGD) via the tail vein seven days post GL26 tumor cells implantation. Confocal imaging of sectioned brains was performed 4 and 24 h post particle administration. FIG. 21B shows that Alexa Fluor 647 labeled SPNPs (cyan) colocalize (indicated with yellow arrows) with macrophages (red) and tumor cells (green, mCitrine). Notably less NPs are observed in the tumor microenvironment 4 h post systemic delivery compared to 24 h. Representative images from a single experiment consisting of three biological replicates per group are displayed. Scale bars=50 μm. FIG. 21C shows a timeline representation of the biodistribution study. Mice were IV administered $2.0 \times 10^{11}$ SPNPs or empty NPs 7, 10, and 13 days post tumor cell implantation or saline injection. FIG. 21D shows fluorescence imaging of tumor-naive and tumor-bearing mice organs sacrificed at 24 h post final NP delivery. FIG. 21E shows quantitative analysis of NP biodistribution within the tumor and peripheral organs. Data are presented as mean values±s.d. (n=4 biological replicates, two-way ANOVA; *$p<0.0001$). FIG. 21F shows quantitative flow cytometry results of vβ3 and avβ5 integrin expression in normal brain tissue and GL26 tumors. Data are presented as mean values±s.d. (n=5 biological replicates; two-tailed unpaired t-test; **$p<0.0001$).

Figure 22:
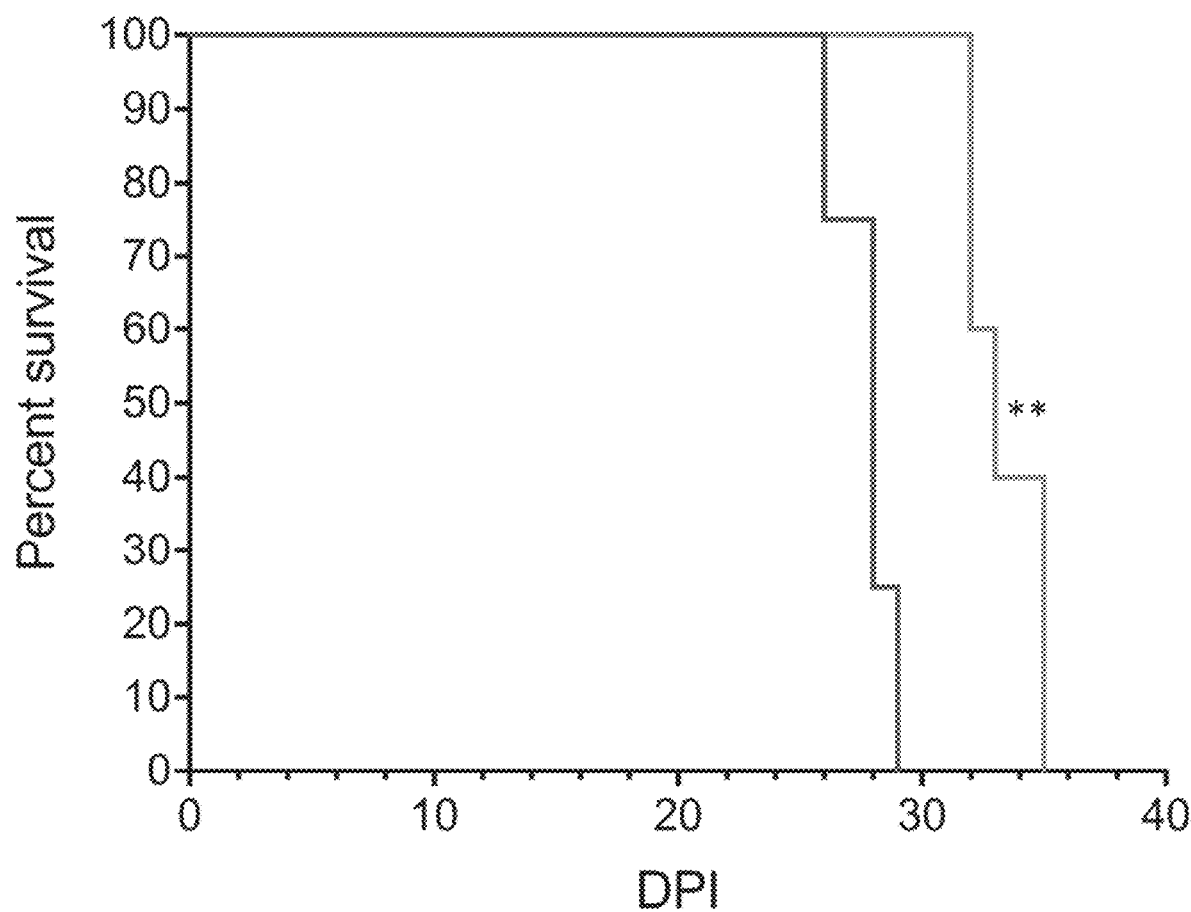

FIG. 22 is a Kaplan-Meier survival curve for single dose of STAT3i SPNPs. C57BL6 mice were implanted with GL26 cells. A single dose of 2.0×1011 STAT3i SPNPs were delivered via tail vein injection five days post tumor implantation. Mice treated with siRNA-loaded particles (red, n=5) had a median survival of 33 days, 5 days longer than mice in the saline treated control group (blue, n=4). Data were analyzed using the log-rank (Mantel-Cox) test. ** p=0.0029, MS=median survival.

Figure 23:
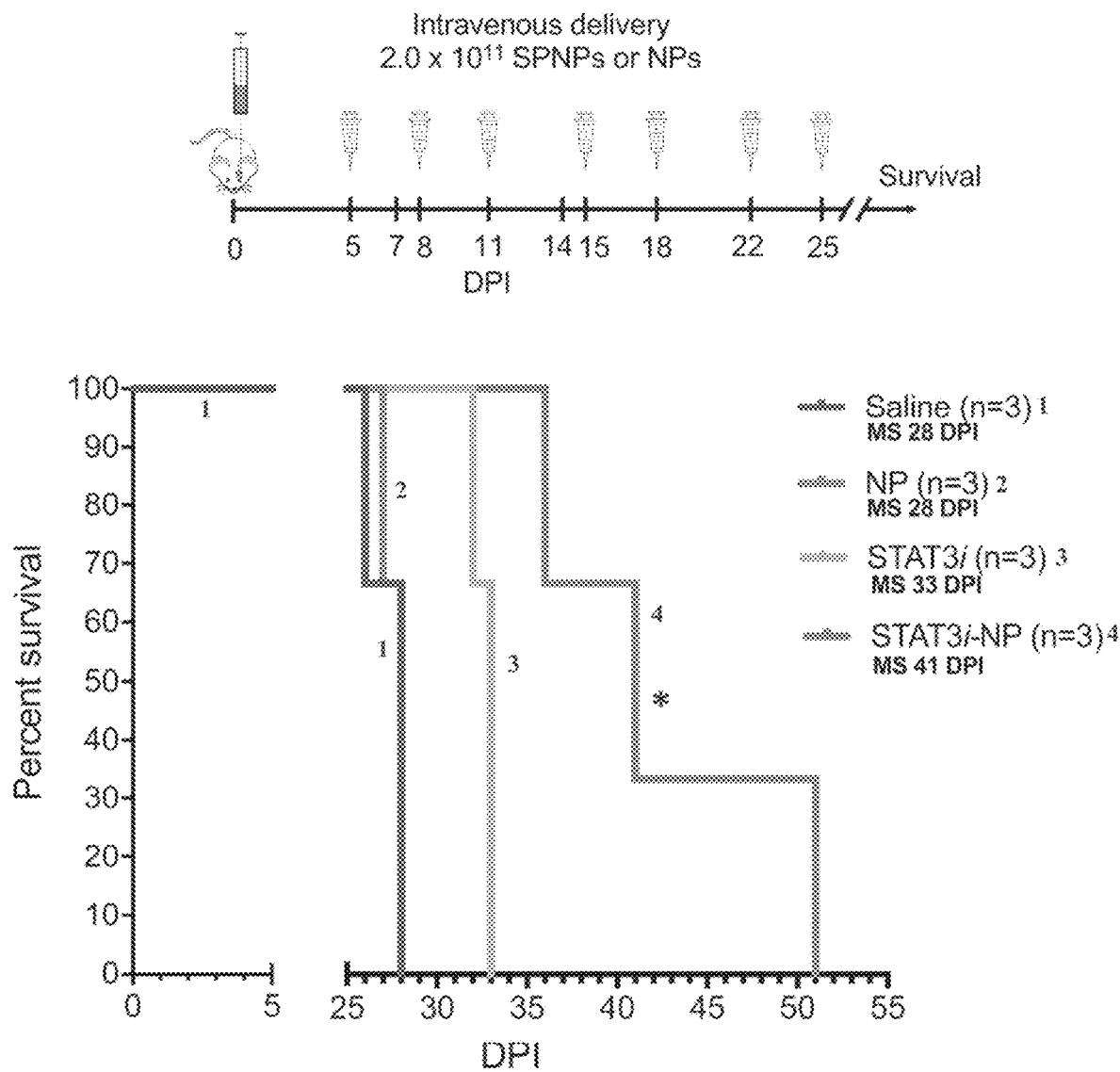

FIG. 23 shows three-week STAT3i SPNP treatment regimen extends median survival. C57BL/6 mice were implanted with GL26 cells, at 5 DPI mice were treated with 2.0×1011 STAT3i SPNPs. STAT3i SPNPs delivered via tail vein (IV) injection. STAT3i SPNPs elicited a 46% increase in median survival compared to saline treated control mice (MS=41 vs. 28). Soluble IV administered STAT3i showed a moderate therapeutic effect (MS=33 vs. 28) while mice treated with vehicle SPNPs saw no effect. Data were analyzed using the log-rank (Mantel-Cox) test. * p=0.0052, MS=median survival.

Figure 24A:
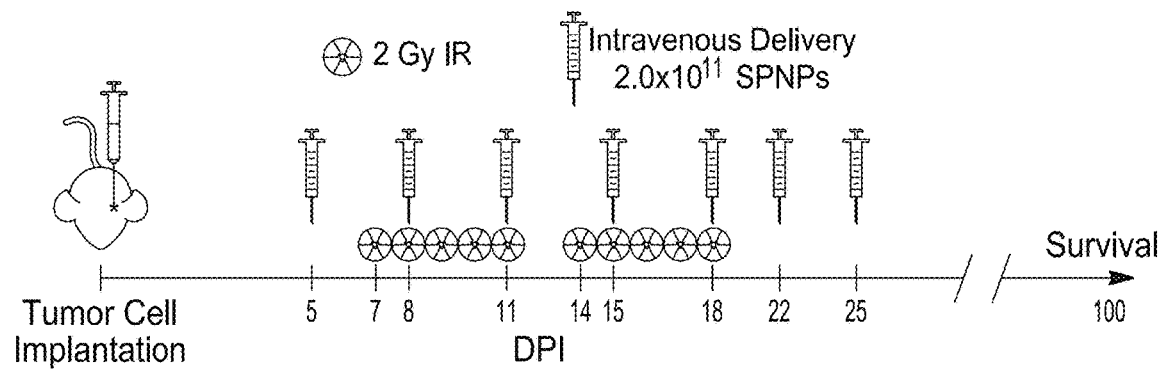
Figure 24B:
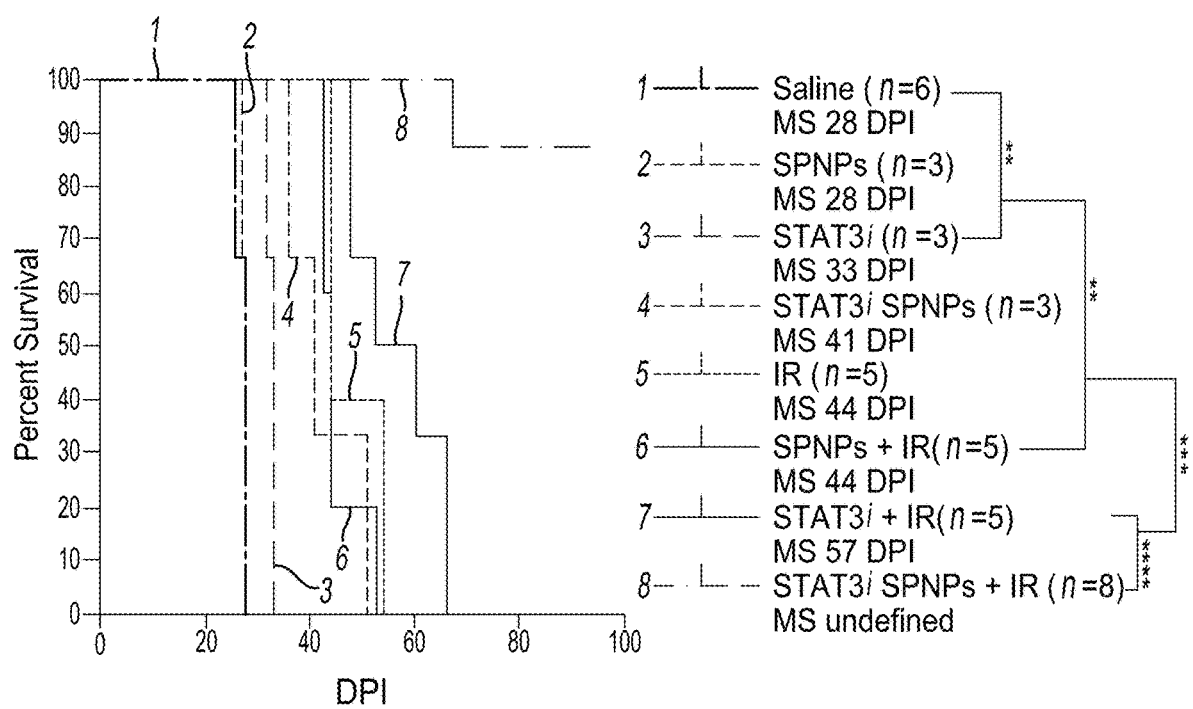
Figure 24C:
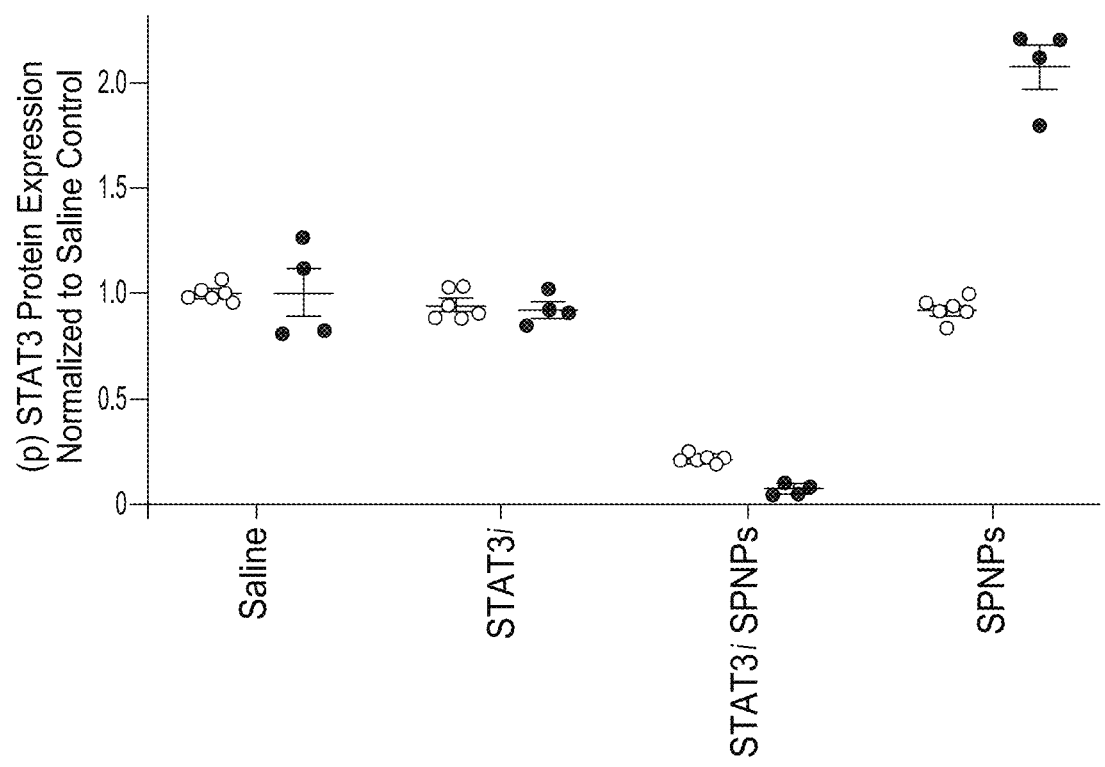
Figure 24D:
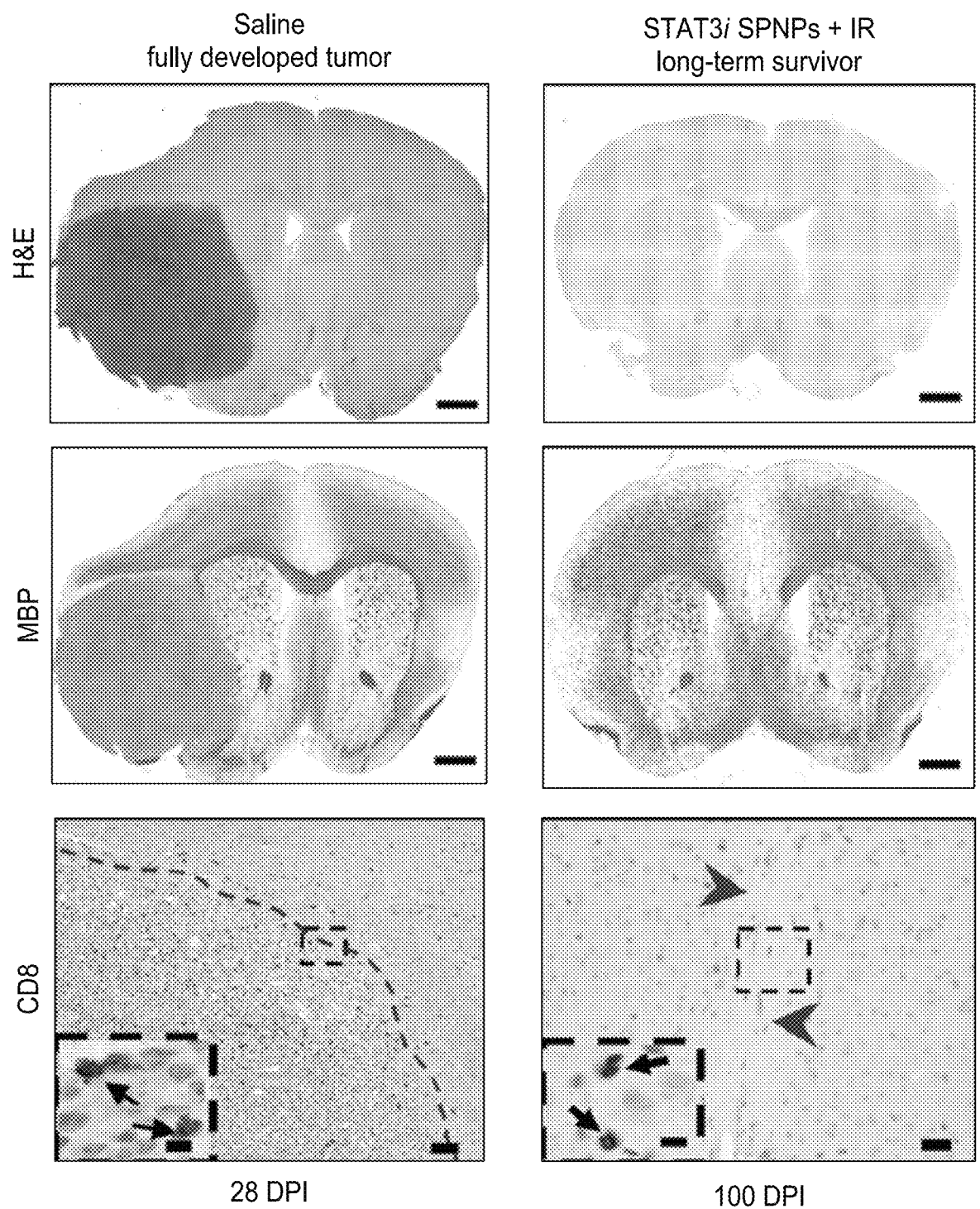
Figure 24E:
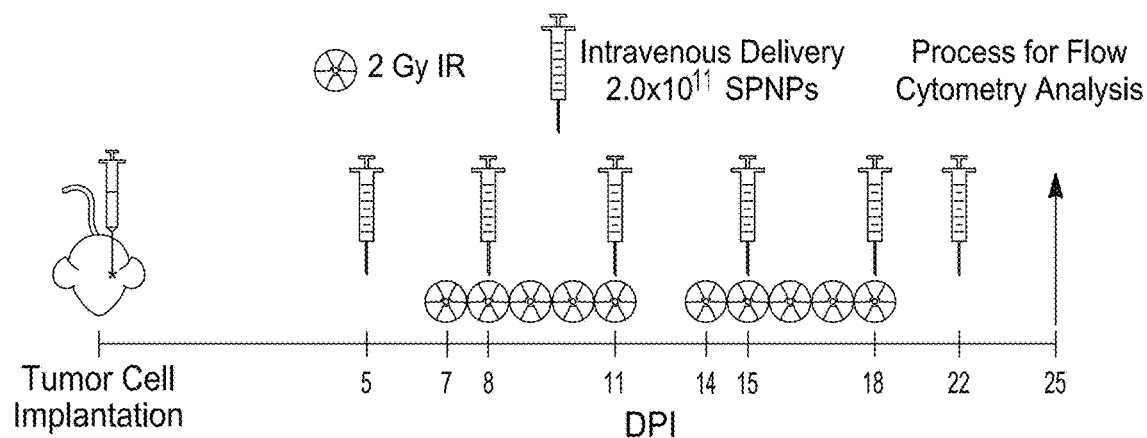
Figure 24F:
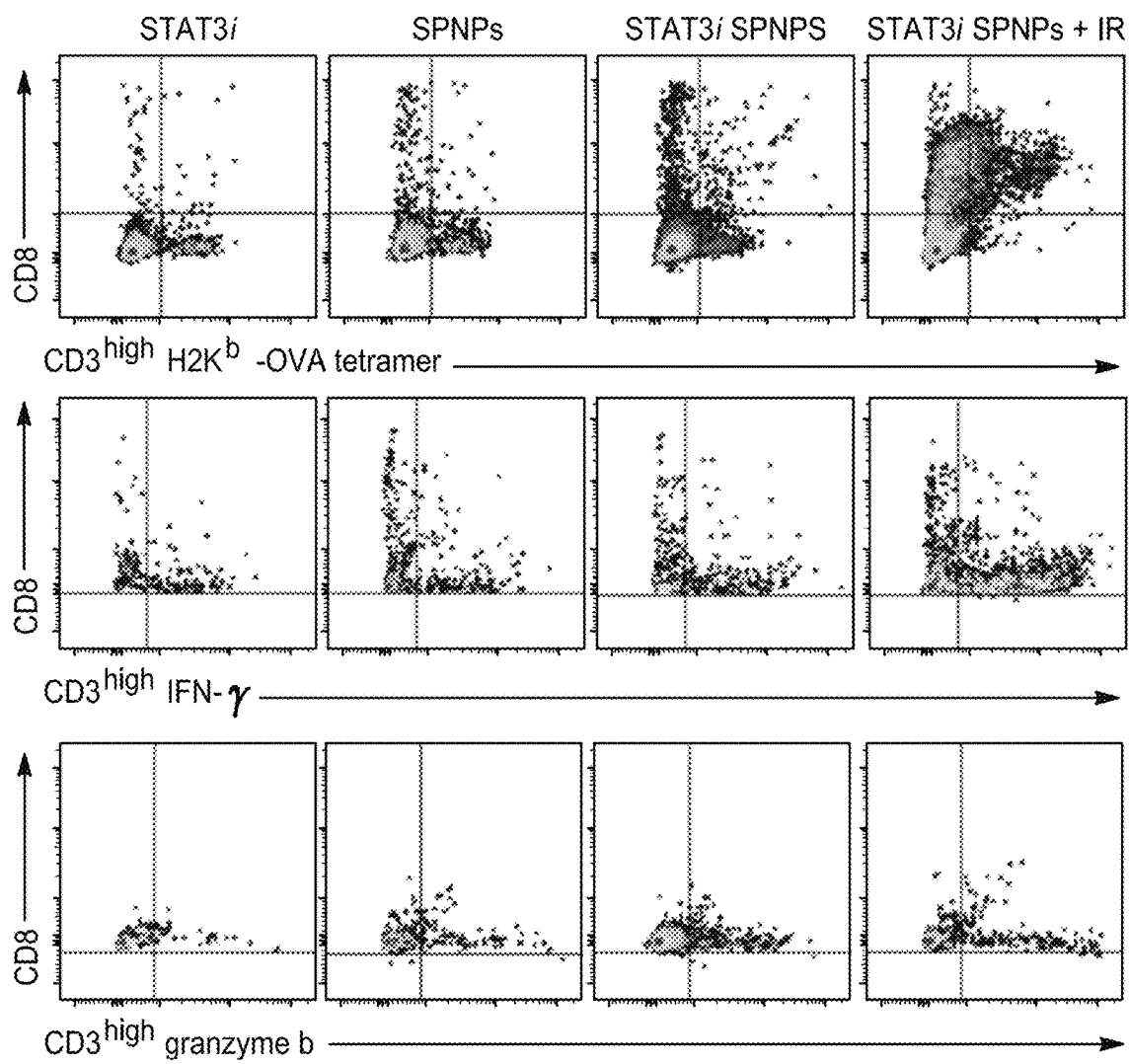
Figure 24G:
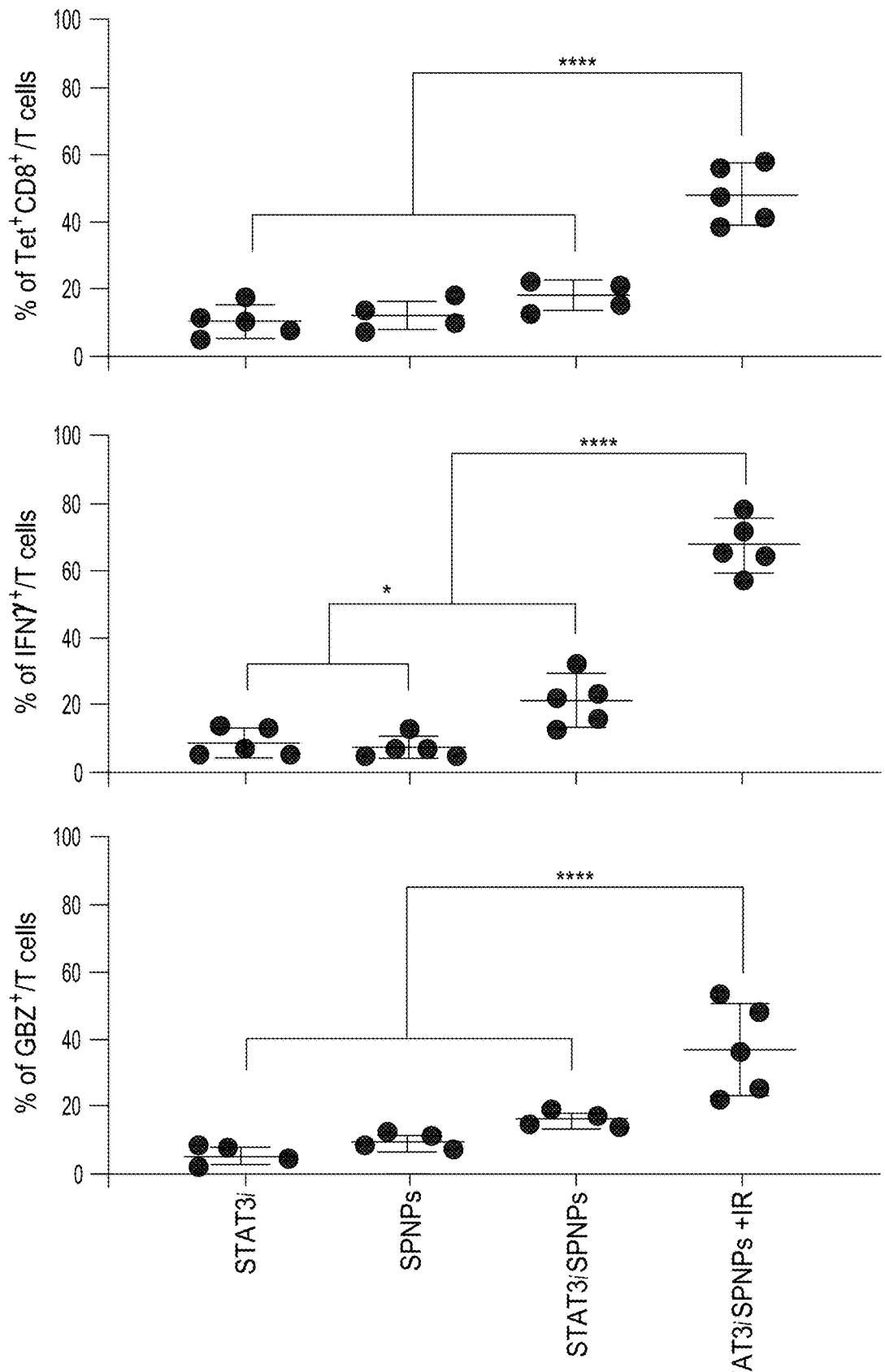

FIGS. 24A-G show that STAT3i SPNPs+IR results in increased survival and primes an adaptive immune response. FIG. 24A shows a timeline of treatment for the combined NP+IR survival study. FIG. 24B shows a Kaplan-Meier survival curve. Significant increase in median survival is observed in all groups receiving IR. Mice (7/8) treated with STAT3i SPNPs+IR reach long-term survival time point (100 DPI) with no signs of residual tumor (Log-rank (Mantel-Cox) test; **$p<0.0001$, *$p<0.001$, $p<0.01$). FIG. 24C shows quantified STAT3 expression for resected brains from the survival study; brains were collected when mice displayed signs of neurological deficits. A significant reduction is STAT3 (black) and pSTAT3 (red) expression was observed in the STAT3i SPNP cohort relative to untreated control. Both soluble STAT3i and empty SPNPs (with no siRNA) did not have high total STAT3 expression but they had increased levels of active phosphorylated STAT3 expression (pSTAT3). Data are presented as mean values±s.d. relative to untreated control (n=2 biological replicates for each group). Due to minimal biological samples available, three technical replicates were performed on each sample to validate the experimental protocol and rule out measurement error. FIG. 24D shows IHC staining for untreated control and STAT3i SPNP+IR long-term survivor. (Top) H&E staining shows the fully formed tumor in the saline control group (28 DPI). When treated with the combination of STAT3i SPNPs+IR, no tumor or signs of necrosis were observed. (Middle) MBP staining shows preserved brain structures with no apparent changes in oligodendrocyte integrity in mice that received STAT3i SPNPs+IR treatment compared to the saline control. Scale bars=1 mm. (Bottom) CD8 staining shows no overt inflammation in mice that received STAT3i SPNPs+IR treatment compared to the saline control. Representative images from a single experiment consisting of three biological replicates per group are displayed. Scale bars=100 μm (inset, 20 μm). FIG. 24E shows a timeline of TME immune population by flow cytometry. FIG. 24F shows a flow cytometry analysis of CD8 cells in the TME. Representative flow plots for each group are displayed. FIG. 24G shows quantitative analysis of tumor-specific CD8+ T cells within the TME. GL26-OVA tumors were analyzed by staining for the SIINFEKL-Kb tetramer. Activation status of CD8+ T cells within the TME was analyzed by staining for granzyme B (Gzb) and IFNg after stimulation with the tumor lysate. Data are presented as mean values±s.d. (n=5 biological replicates; one-way ANOVA and Tukey's multiple comparison tests; **$p<0.0001$).

Figure 25:
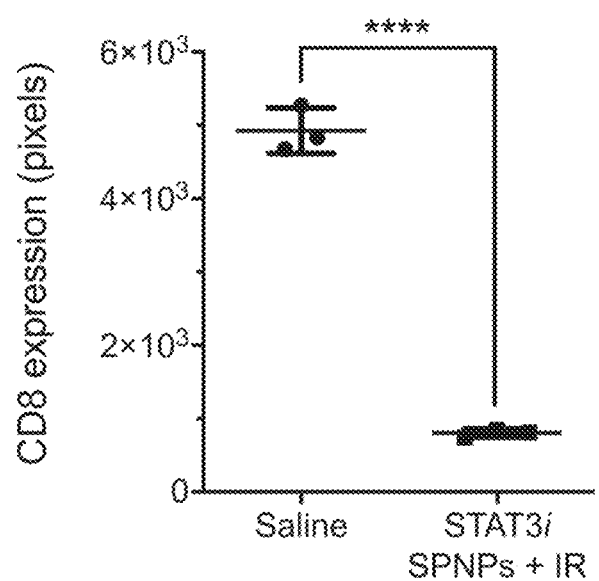

FIG. 25 shows quantification of CD8 Expression in TME. Immunofluorescence staining of tumors in either saline or STAT3i SPNP+IR treatment groups was quantified using otsu threshold by ImageJ. Data represent total number of positive cells for CD8 in saline (28 DPI) versus STAT3i SPNPs+IR (90 DPI) long-term survivor. Data are presented as mean±s.d. (n=3 biological replicates; two-tailed unpaired t-test; **** $p<0.0001$).

Figure 26:
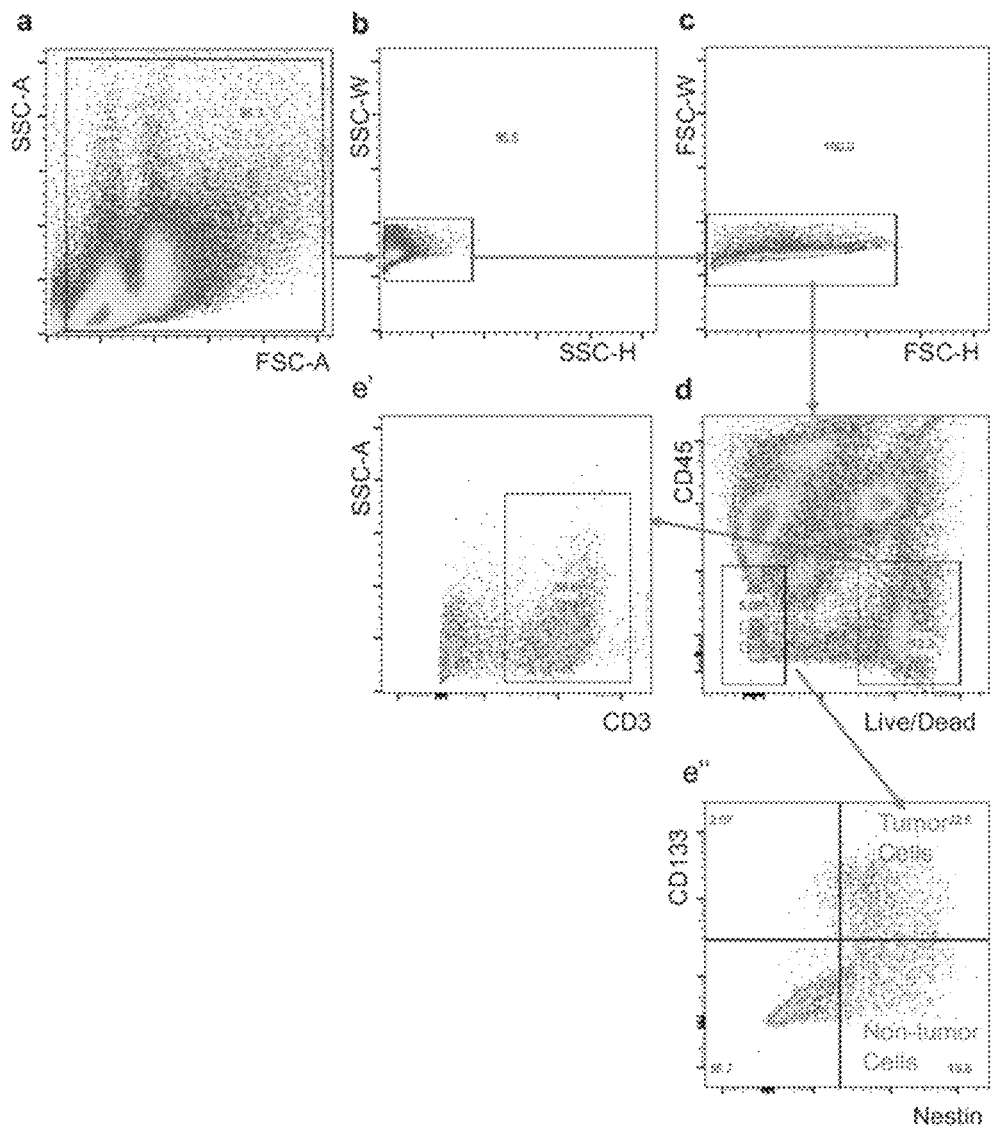

FIG. 26 is a set of flow cytometry data showing the sequential gating strategy for flow cytometry analysis of immunolabeled cells. (a) Immunolabeled cells were gated to exclude cellular debris. (b)-(c) Doublet discrimination gating was performed to filter out cellular aggregates prior to analysis. (d) CD45+/Live cells were gated to identify GBM infiltrating M1 (CD45+/F480+/CD206-), and M2 (CD45+/F480+/CD206+) macrophages shown in FIG. 15a as well as cDCs (CD45+/CD11c+/B220-) shown in FIG. 15b. CD45-/Live cells were gated to identify tumor cells. (e') Identification of live CD3+ cells from the CD45+/Live parent gate in (d) to determine the amount of GBM specific T cells (CD45+/CD3+/CD8+/H2 Kb-OVA tetramer+), and cytotoxic T cells (CD45+/CD3+/CD8+/IFN-y or CD45+/CD3+/CD8+/granzyme B) in the TME shown in FIG. 13f (e") Identification of CD133+/nestin+GBM cells from the CD45-/live parent gate in (d) for avβ3 and avβ5 integrin expression analysis shown in FIG. 10F.

FIGS. 27A-27L show that STAT3i SPNPs+IR results in no abnormal toxicity. FIG. 27A is a timeline of treatment to assess the effect of STAT3i SPNP+IR treatment. Blood and liver samples were collected from GL26 GBM bearing mice treated with saline, STAT3i, SPNP, STAT3i SPNP or STAT3i SPNP+IR at 23 DPI following complete therapeutic regimen. b-i For each treatment group, levels of (b) hemoglobin, (c) hematocrit, (d) lymphocytes, (e) monocytes, (f) neutrophils, (g) platelet, (h) red blood cell (RBC), and (i) white blood cell (WBC) counts were quantified in FIGS. 27B-27i. Data are presented as mean values±s.d. (n=3 biological replicates; one-way ANOVA and Tukey's multiple comparison tests; ns=p>0.05). j Histology performed on resected livers following a complete treatment of GMB tumor-bearing mice find isolated regions of mild coagulative necrosis deemed to be well-contained and therefore would not induce a biological effect on liver function. In all groups, with the exception of the saline-treated control, signs of hepatocellular necrosis were observed. This is attributed to water or glycogen accumulation in hepatocytes associated with a change in energy balance rather than a degenerative change. Representative images from a single experiment consisting of independent biological replicates are displayed. Scale bars=100 μm (20×), 50 μm (40×). FIGS. 27K and 27L show that, following complete STAT3i SPNPs+IR treatment, circulating antibodies against (k) mouse serum albumin nanoparticles were not observed in serum of GL26 tumor-bearing mice. When exchanging (l) human serum albumin in the formulation, maintaining all other components, measurable serum HSA-specific antibody levels are observed. Data are presented as mean values±s.d. (n=3 biological replicates; one-way ANOVA and Tukey's multiple comparison tests; ****p<0.0001).

FIG. 28 is a table describing the mouse serum biochemical analysis following intravenous STAT3i SPNP+IR treatment. (n=3).

Figure 29:
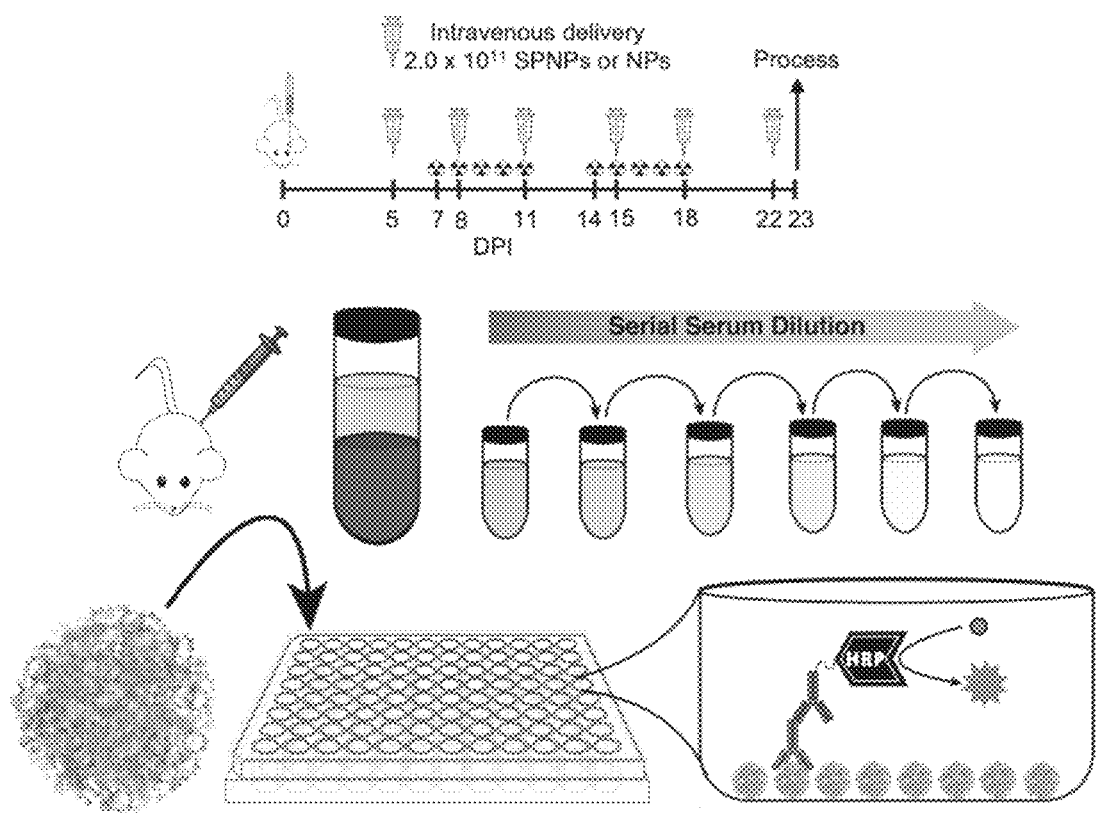

FIG. 29 is a schematic showing evaluation of circulating antibodies against STAT3i SPNPs. Following complete STAT3i SPNPs+IR treatment, a modified ELISA protocol was used to detect the presence of circulating antibodies against SPNPs in serum of GL26 tumor bearing mice.

Figure 30A:
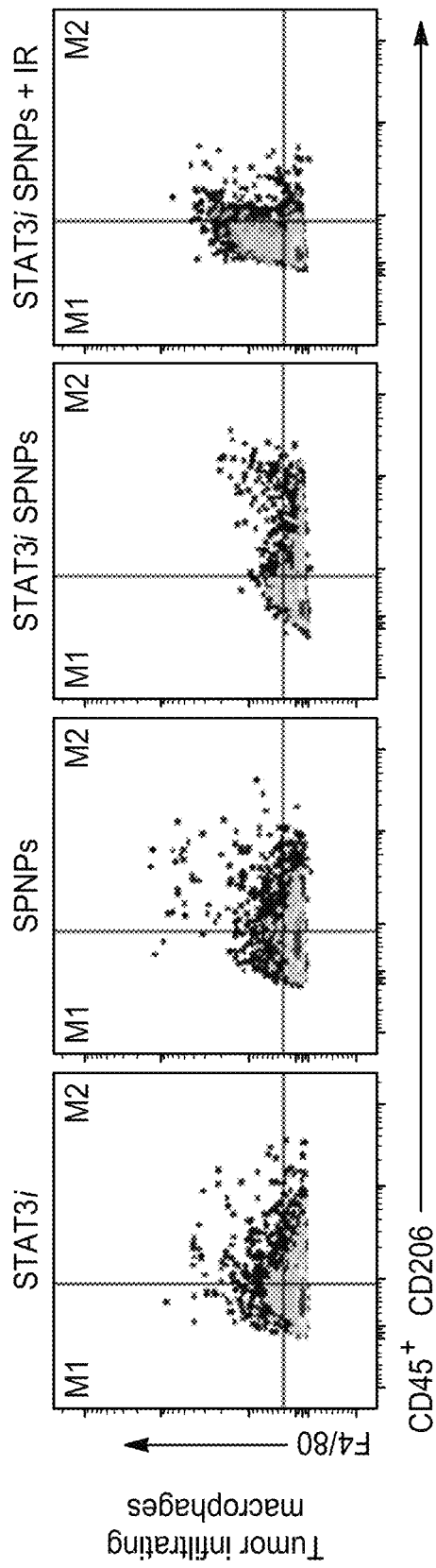
Figure 30B:
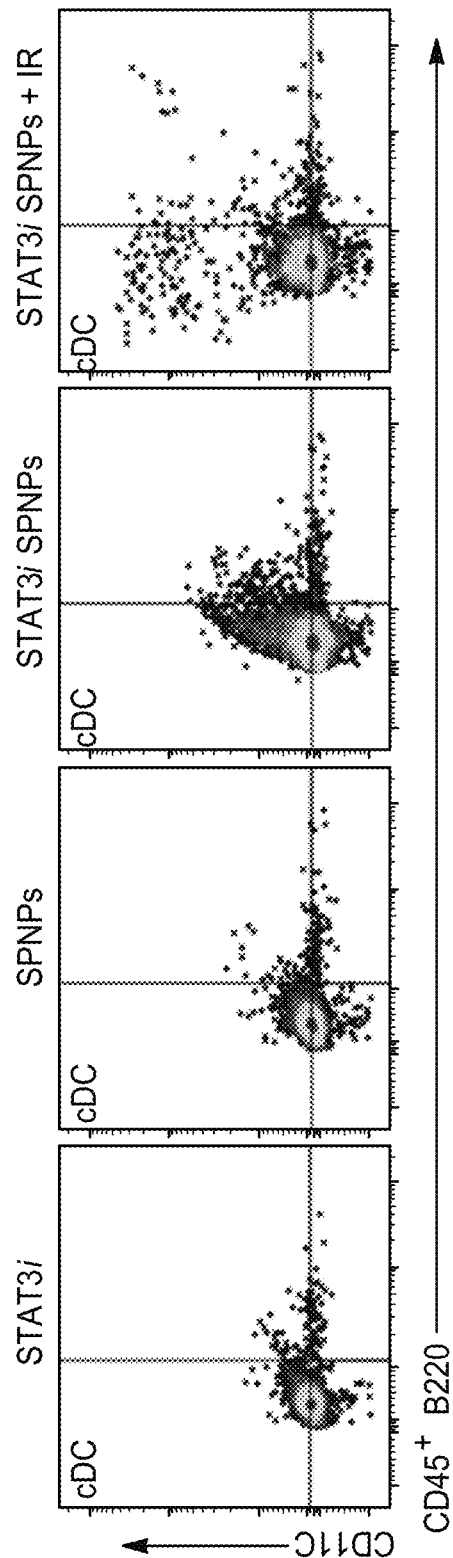
Figure 30C:
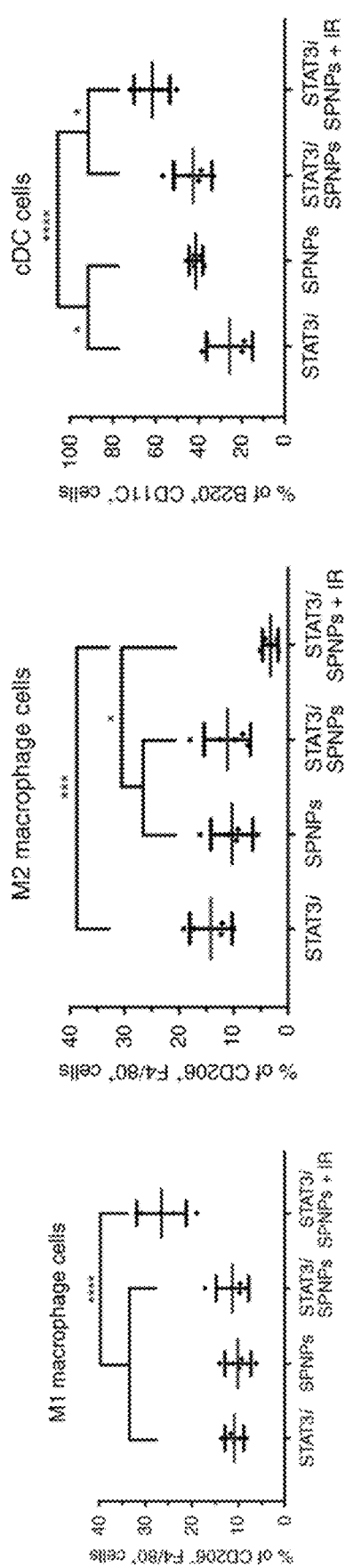
Figure 30D:
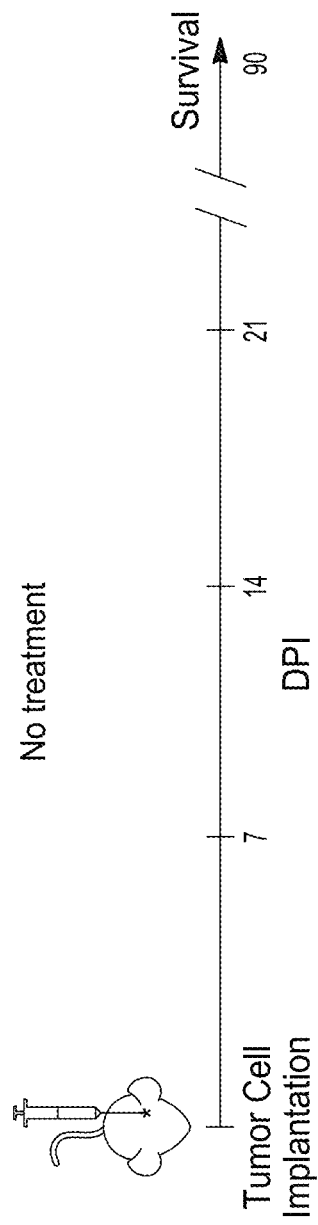
Figure 30E:
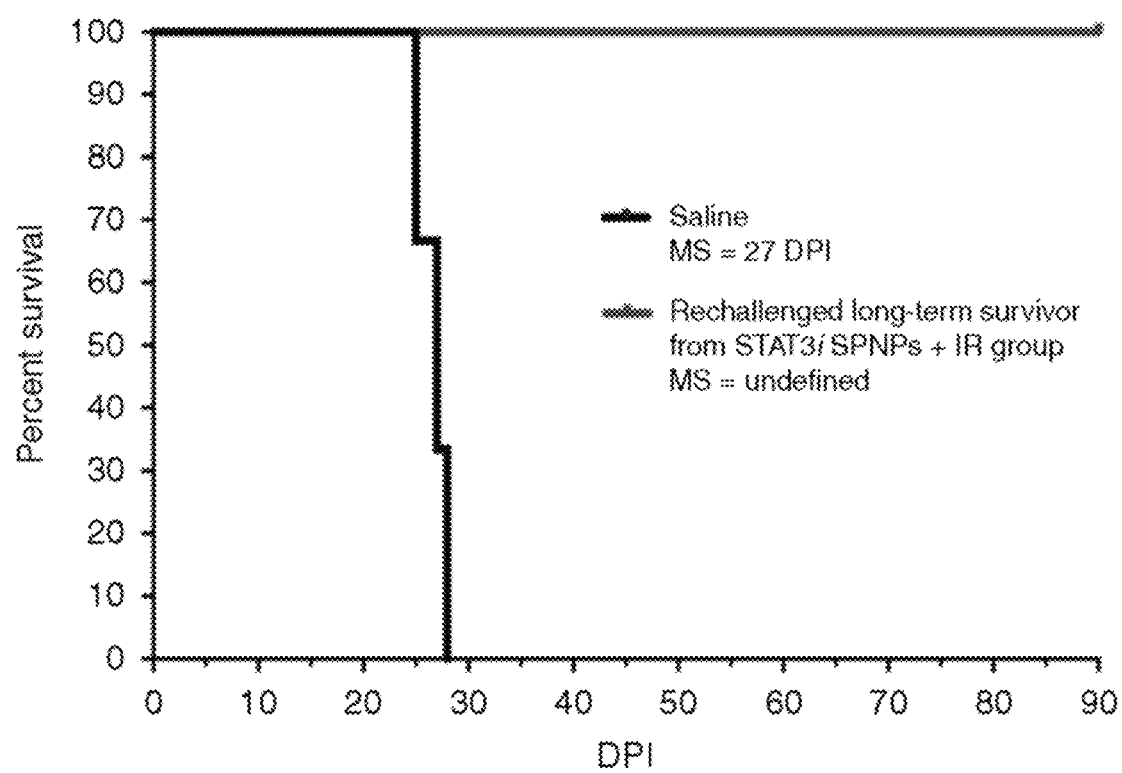
Figure 30F:
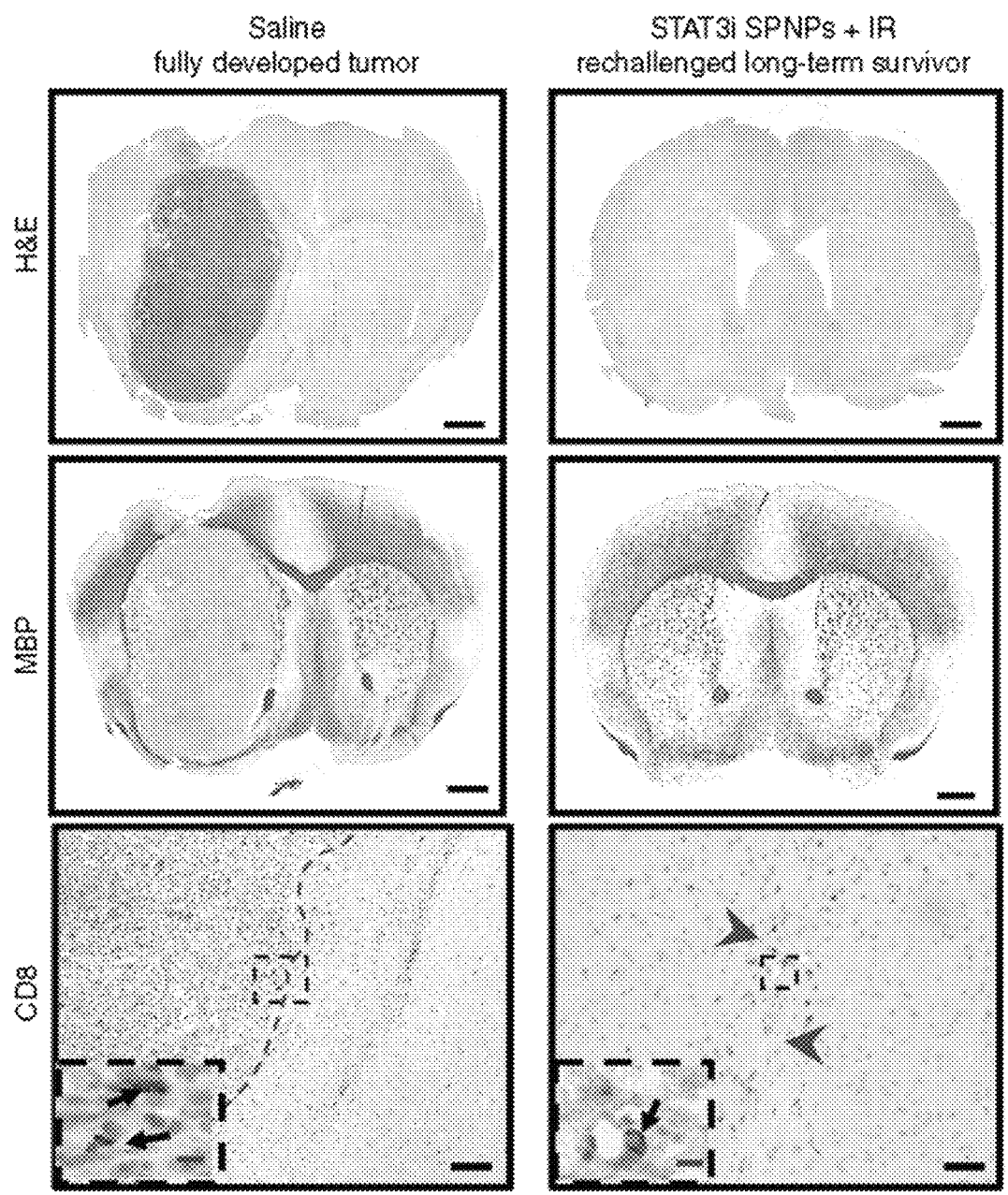

FIGS. 30A-30F show that SPNPs protect against GBM rechallenge. FIGS. 30A and 30B show flow analysis of tumor-infiltrating (a) macrophage and (b) conventional dendritic cell (cDCs) populations in the TME following NP+IR treatment regimen. Representative flow plots for each group are displayed. FIG. 30C shows quantitative analysis of the immune cellular infiltrates showed a shift in the relative macrophage (M1vs. M2) present in the TME. In the free siRNA, empty SPNPs, and STAT3i SPNPs groups no significant change in the macrophage population were observed. Conversely, STAT3i SPNPs+IR treatment induces both a surge of ~2.5-fold increase in M1 population and a sharp 3- to 4-fold decrease in M2 macrophages. Among cDCs, progressively larger numbers of the cell population were observed moving from free siRNA to SPNPs groups. The combined treatment of STAT3i SPNPs with IR displayed the highest number of cDCs in the brain TME. Data are presented as mean values±s.d. (=5 biological replicates; one-way ANOVA and Tukey's multiple comparison tests; **p<0.0001, *p<0.001, *p (M2)=0.028, 0.013, *p(cDC)=0.038, 0.011). FIG. 30D shows a timeline for rechallenging the long-term survivor for STAT3i SPNPs+IR survival study rechallenged, where following tumor implantation, no further treatment was provided. FIG. 30E shows a Kaplan-Meier survival curve shows all rechallenged survivors reach a second long-term survival timepoint of 90 DPI in the absence of any therapeutic interventions. FIG. 30F shows H&E (Top, Scale bars=1 mm), MBP (Middle, Scale bars=1 mm), and CD8 (Bottom, Scale bars, 100 μm (inset 20 μm)) IHC staining comparing the brains of untreated and rechallenged long-term survivors. Representative images from a single experiment consisting of three biological replicates per group are displayed. No overt signs of remaining tumor, necrosis, inflammation, or disruption of normal brain architecture was observed in rechallenged long-term survivors from STAT3i SPNPs treatment group.

Figure 31:
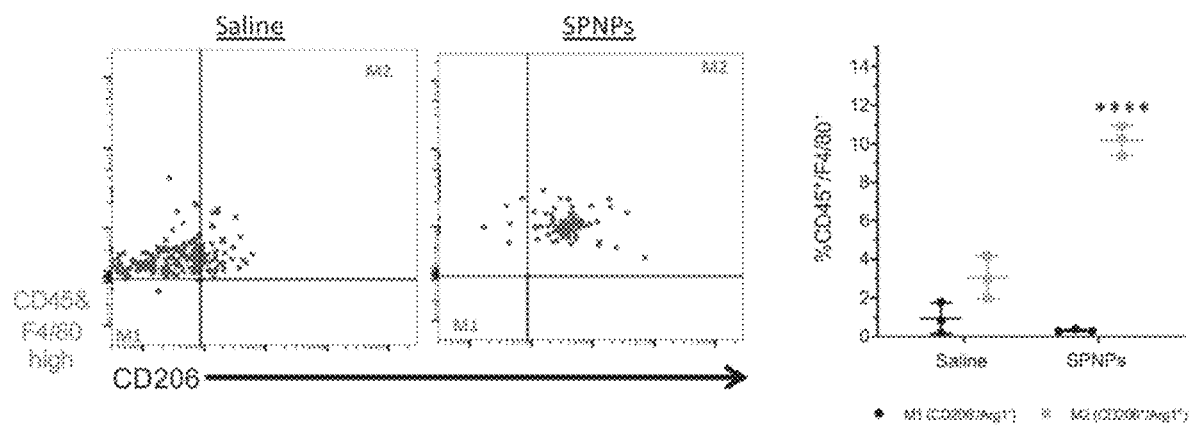

FIG. 31 shows that SPNPs treatment induces a shift in the TME macrophage balance. Treatment of GL26 tumor-bearing mice with empty SPNPs produced a shift in macrophage populations within the tumor microenvironment. An increase in the M2 macrophages relative to saline treated control animals was observed. Data are presented as mean values±s.d. (n=3 biological replicates; two-way ANOVA; ****p<0.0001)

Figure 32:
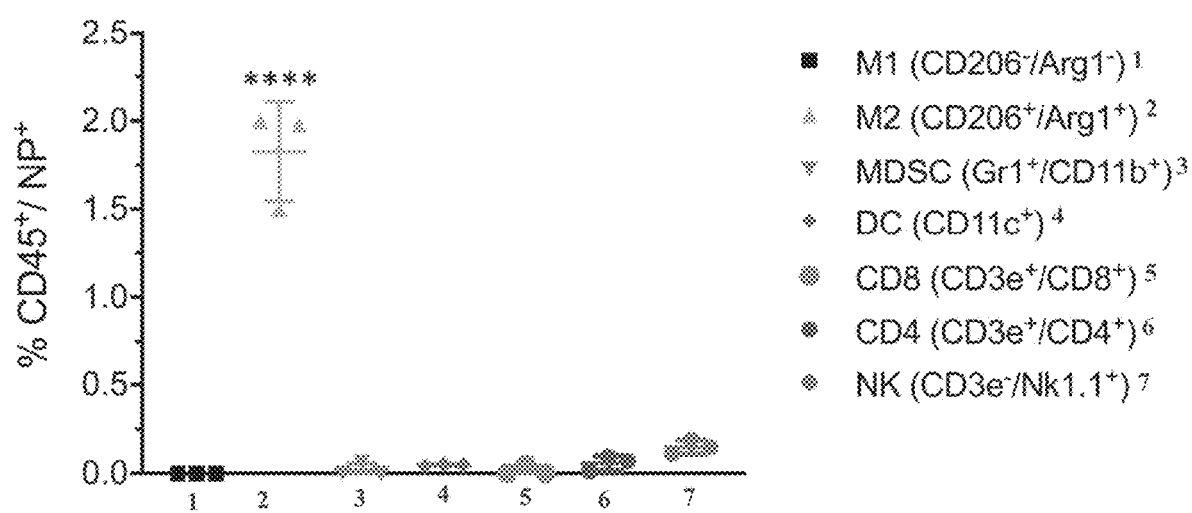

FIG. 32 shows that, among TME immune cells, only M2 macrophages showed significant uptake of SPNPs. Flow cytometry analysis of immune cells collected from the tumor microenvironment of SPNPs treated mice show significant nanoparticle uptake by M2 macrophages and minimal uptake by all other immune cell types. Data are presented as mean values±s.d. (n=3 biological replicates; two-way ANOVA; ****p<0.0001).

Figure 33:
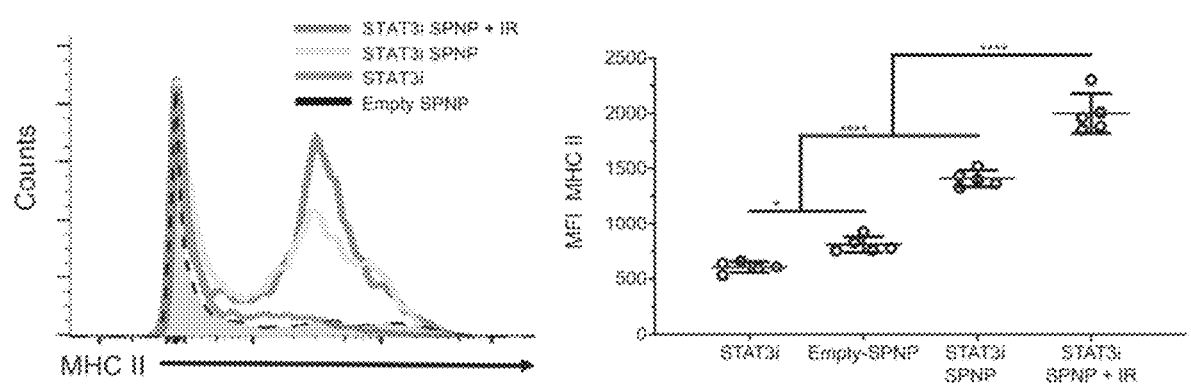

FIG. 33 shows dendritic cell MHC II expression. Activation status of DCs in the draining lymph node of GBM bearing mice treated with STAT3i, empty SPNP, STAT3i SPNP, and STAT3i SPNP+IR was assessed one day post the last day of treatment (23 DPI). Representative histograms display MHC II expression level on the DCs (purple=STAT3i, black=empty SPNP, red=STAT3i SPNP+IR, green=STAT3i SPNP). Data is presented as mean values±s.d. (n=5 biological replicates; one way ANOVA; **** p<0.0001, * p=0.036).

Figure 34:
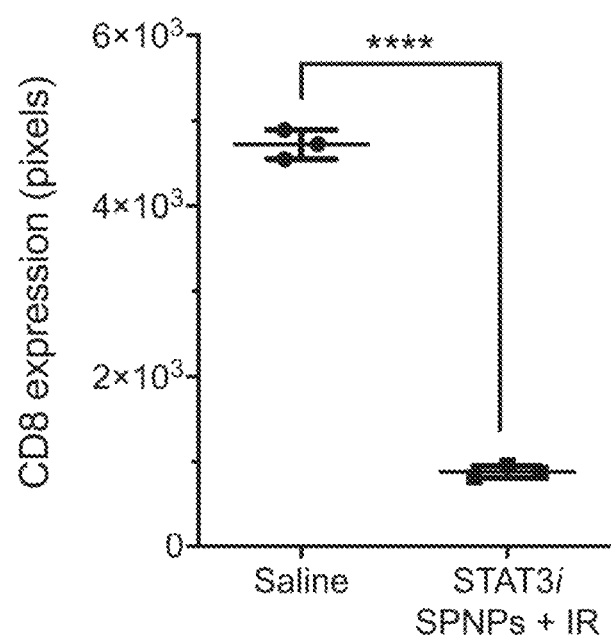

FIG. 34 is a graph showing quantification of CD8 expression in rechallenged long-term survivor TME. Immunofluorescence staining of tumors in each treatment group was quantified using otsu threshold by ImageJ. Data represent total number of positive cells for CD8 in saline (28 DPI) versus STAT3i SPNPs+IR (90 DPI post rechallenged; 180 DPI post initial tumor implantation) rechallenged long-term survivor. Data are presented as mean values±s.d. (n=3 biological replicates; two-tailed, unpaired t-test; **** p<0.0001).

Corresponding reference numerals indicate corresponding parts throughout the several views of the drawings.

DETAILED DESCRIPTION

Example embodiments are provided so that this disclosure will be thorough, and will fully convey the scope to those who are skilled in the art. Numerous specific details are set forth such as examples of specific compositions, components, devices, and methods, to provide a thorough understanding of embodiments of the present disclosure. It will be apparent to those skilled in the art that specific details need not be employed, that example embodiments may be embodied in many different forms and that neither should be construed to limit the scope of the disclosure. In some example embodiments, well-known processes, well-known device structures, and well-known technologies are not described in detail.

The terminology used herein is for the purpose of describing particular example embodiments only and is not intended to be limiting. As used herein, the singular forms "a," "an," and "the" may be intended to include the plural forms as well, unless the context clearly indicates otherwise. The terms "comprises," "comprising," "including," and "having," are inclusive and therefore specify the presence of stated features, elements, compositions, steps, integers, operations, and/or components, but do not preclude the presence or addition of one or more other features, integers, steps, operations, elements, components, and/or groups thereof. Although the open-ended term "comprising," is to be understood as a non-restrictive term used to describe and claim various embodiments set forth herein, in certain aspects, the term may alternatively be understood to instead be a more limiting and restrictive term, such as "consisting of" or "consisting essentially of." Thus, for any given embodiment reciting compositions, materials, components, elements, features, integers, operations, and/or process steps, the present disclosure also specifically includes embodiments consisting of, or consisting essentially of, such recited compositions, materials, components, elements, features, integers, operations, and/or process steps. In the case of "consisting of," the alternative embodiment excludes any additional compositions, materials, components, elements, features, integers, operations, and/or process steps, while in the case of "consisting essentially of," any additional compositions, materials, components, elements, features, integers, operations, and/or process steps that materially affect the basic and novel characteristics are excluded from such an embodiment, but any compositions, materials, components, elements, features, integers, operations, and/or process steps that do not materially affect the basic and novel characteristics can be included in the embodiment.

Any method steps, processes, and operations described herein are not to be construed as necessarily requiring their performance in the particular order discussed or illustrated, unless specifically identified as an order of performance. It is also to be understood that additional or alternative steps may be employed, unless otherwise indicated.

When a component, element, or layer is referred to as being "on," "engaged to," "connected to," or "coupled to" another element or layer, it may be directly on, engaged, connected or coupled to the other component, element, or layer, or intervening elements or layers may be present. In contrast, when an element is referred to as being "directly on," "directly engaged to," "directly connected to," or "directly coupled to" another element or layer, there may be no intervening elements or layers present. Other words used to describe the relationship between elements should be interpreted in a like fashion (e.g., "between" versus "directly between," "adjacent" versus "directly adjacent," etc.). As used herein, the term "and/or" includes any and all combinations of one or more of the associated listed items.

Although the terms first, second, third, etc. may be used herein to describe various steps, elements, components, regions, layers and/or sections, these steps, elements, components, regions, layers and/or sections should not be limited by these terms, unless otherwise indicated. These terms may be only used to distinguish one step, element, component, region, layer or section from another step, element, component, region, layer or section. Terms such as "first," "second," and other numerical terms when used herein do not imply a sequence or order unless clearly indicated by the context. Thus, a first step, element, component, region, layer or section discussed below could be termed a second step, element, component, region, layer or section without departing from the teachings of the example embodiments.

Spatially or temporally relative terms, such as "before," "after," "inner," "outer," "beneath," "below," "lower," "above," "upper," and the like, may be used herein for ease of description to describe one element or feature's relationship to another element(s) or feature(s) as illustrated in the figures. Spatially or temporally relative terms may be intended to encompass different orientations of the device or system in use or operation in addition to the orientation depicted in the figures.

Throughout this disclosure, the numerical values represent approximate measures or limits to ranges to encompass minor deviations from the given values and embodiments having about the value mentioned as well as those having exactly the value mentioned. Other than in the working examples provided at the end of the detailed description, all numerical values of parameters (e.g., of quantities or conditions) in this specification, including the appended claims, are to be understood as being modified in all instances by the term "about" whether or not "about" actually appears before the numerical value. "About" indicates that the stated numerical value allows some slight imprecision (with some approach to exactness in the value; approximately or reasonably close to the value; nearly). If the imprecision provided by "about" is not otherwise understood in the art with this ordinary meaning, then "about" as used herein indicates at least variations that may arise from ordinary methods of measuring and using such parameters. For example, "about" may comprise a variation of less than or equal to 5%, optionally less than or equal to 4%, optionally less than or equal to 3%, optionally less than or equal to 2%, optionally less than or equal to 1%, optionally less than or equal to 0.5%, and in certain aspects, optionally less than or equal to 0.1%.

In addition, disclosure of ranges includes disclosure of all values and further divided ranges within the entire range, including endpoints and sub-ranges given for the ranges.

Example embodiments will now be described more fully with reference to the accompanying drawings.

Figure 1:
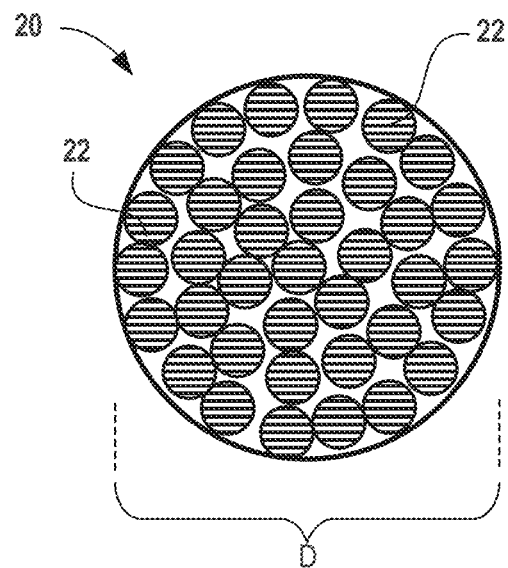
FIG. 1 shows a cross-section view of an example of a nanoparticle formed of water-soluble proteins according to certain aspects of the present disclosure.

In various aspects, the present disclosure provides a nanoparticle formed of a protein. For example, a representative view of one such a nanoparticle 20 in the form of a sphere is shown in FIG. 1. The nanoparticle 20 includes a plurality of proteins 22 that are cross-linked and together define the nanoparticle 20. The nanoparticle 20 may have a diameter "D" or major dimension that is in the nanoscale range.

A nanoparticle is a material that has a variety of shapes or morphologies, however, generally has at least one spatial dimension that is less than about 1 μm (i.e., 1,000 nm), optionally less than about 0.75 μm (i.e., 750 nm), optionally less than about 0.5 μm (i.e., 500 nm), and in certain aspects, less than about 0.25 μm (i.e., 200 nm). In some instances, the nanoparticle has a least one spatial dimension that is less than about 300 nm (e.g., diameter of less than 300 nm (e.g., mean diameter of less than 300 nm or median diameter of less than 300 nm), e.g., diameter between 100 nm and 300 nm (e.g., mean diameter between 100 nm and 300 nm or median diameter between 100 nm and 300 nm), e.g., from 100 to 150 nm, from 150 to 200 nm, from 200 to 250 nm, or from 250 to 300 nm, e.g., about 150 nm, about 200 nm, about 250 nm, or about 300 nm). In some instances, the nanoparticle has at least one spatial dimension that is less than about 100 nm (e.g., diameter of less than 100 nm (e.g., mean diameter of less than 100 nm or median diameter of less than 100 nm), e.g., diameter between 10 nm and 100 nm (e.g., mean diameter between 10 nm and 100 nm or median diameter between 10 nm and 100 nm), e.g., about 95 nm, about 90 nm, about 85 nm, about 80 nm, about 75 nm, about 70 nm, about 65 nm, about 60 nm, about 55 nm, about 50 nm, or about 40 nm (e.g., mean diameter of about 95 nm, about 90 nm, about 85 nm, about 80 nm, about 75 nm, about 70 nm, about 65 nm, about 60 nm, about 55 nm, about 50 nm, or about 40 nm or median diameter of about 95 nm, about 90 nm, about 85 nm, about 80 nm, about 75 nm, about 70 nm, about 65 nm, about 60 nm, about 55 nm, about 50 nm, or about 40 nm)). In certain aspects, a nanoparticle has at least one spatial dimension, such as a diameter, that is greater than or equal to about 5 nm and less than or equal to about 1,000 nm, optionally greater than or equal to about 5 nm to less than or equal to about 500 nm, optionally greater than or equal to about 10 nm to less than or equal to about 1,000 nm, optionally greater than or equal to about 10 nm to less than or equal to about 500 nm, optionally greater than or equal to about 25 nm to less than or equal to about 1,000 nm, optionally greater than or equal to about 25 nm to less than or equal to about 500 nm, optionally greater than or equal to about 50 nm to less than or equal to about 1,000 nm, optionally greater than or equal to about 50 nm to less than or equal to about 500 nm, optionally greater than or equal to about 100 nm to less than or equal to about 1,000 nm, and in certain aspects, optionally greater than or equal to about 100 nm to less than or equal to about 500 nm.

The nanoparticle may have a variety of geometries or morphologies, including, by way of non-limiting example, substantially round shapes, like spheres and ellipsoids/ovals, rectangles, polygons, discoids/discs, ellipsoids, toroids, cones, pyramids, rods/cylinders, and the like. In certain aspects, the nanoparticle may have a substantially round shape, such as spheres, ellipsoids, hemispheres, and the like.

In certain variations, the nanoparticle comprises a water-soluble protein that may be cross-linked. The water-soluble protein may have an average molecular weight of greater than or equal to about 8 kDa and less than or equal to about 700 kDa, so long as it is water soluble. In certain variations, the cross-linked water-soluble protein nanoparticles define a caged or mesh structure. By mesh structure, it is meant that the nanoparticle has a cross-linked protein network that defines three-dimensional structures having openings, voids, or pores defined therein. The mesh size is one defining aspect of the protein nanoparticles according to the present teachings.

Figure 2:
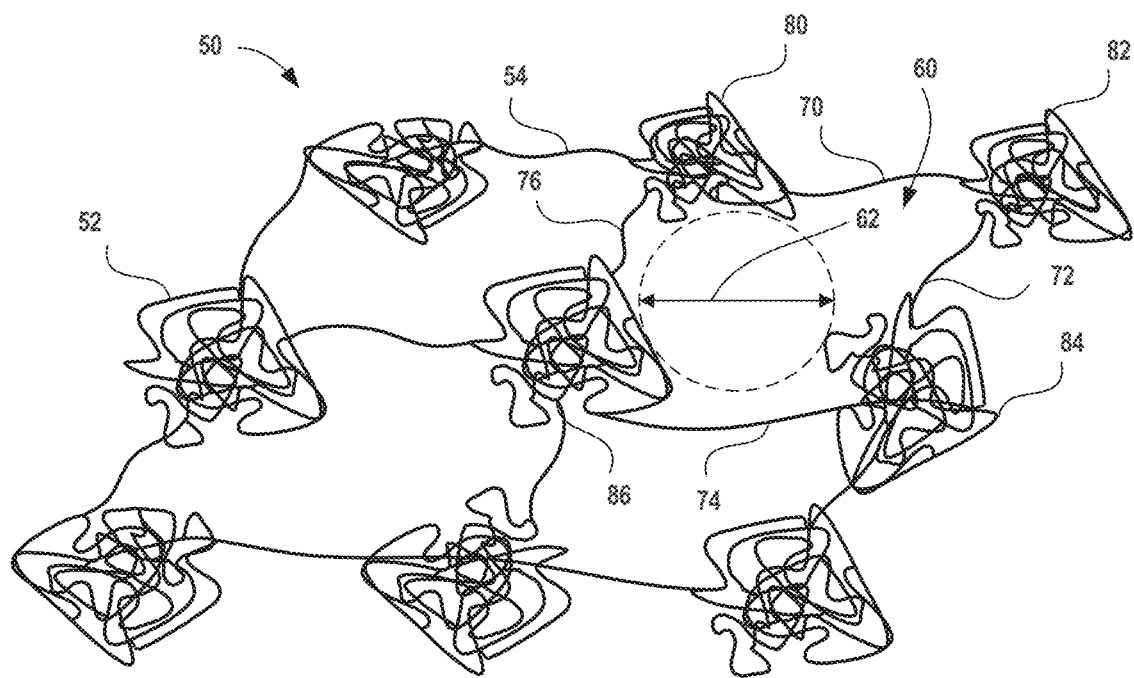
FIG. 2 shows a detailed view of a nanoparticle having cross-linked proteins defining a representative mesh structure according to certain aspects of the present disclosure.

For purposes of illustration, FIG. 2 shows a detailed view of a representative non-limiting mesh structure 50 within a nanoparticle comprising a cross-linked water-soluble protein. While the nanoparticle may be considered to be porous, in contrast to more traditional porous materials, the mesh structure may be considered to be a more open structure with a high porosity level so that a large portion of the nanoparticle comprises openings defined between each pore. Further, the openings are interconnected with one another. In other words, the cross-linked protein defines a cage-like or structural lattice-type framework that may be considered to be interconnected struts and bridges that create the mesh structure 50. In certain aspects, the mesh structure 50 may have an overall open volume (aside from the water-soluble proteins and optional crosslinking agents) of greater than or equal to about 50 volume %, optionally greater than or equal to about 60 volume %, optionally greater than or equal to about 70 volume %, and optionally greater than or equal to about 80 volume % of the overall nanoparticle volume.

FIG. 2 shows one layer of the mesh structure 50 in a nanoparticle prepared in accordance with certain aspects of the present disclosure. A plurality of proteins 52 are connected by cross-linking bridges 54. In certain variations, the cross-linking bridges 54 may be distinct crosslinking agents reacted with (e.g., conjugated to) the water-soluble protein.

In other variations, the water-soluble proteins may be self-cross-linked without any distinct crosslinking agent present. As shown in FIG. 2, an opening 60 is defined between a first crosslink bridge 70, a first protein 80, a second crosslink bridge 72, a second protein 82, a third crosslink bridge 74, a third protein 84, a fourth crosslink bridge 76, and a fourth protein 86. As can be seen, the first crosslink bridge 70 is reacted with and links the first protein 80 and second protein 82. The second crosslink bridge 72 links the second protein 82 and third protein 84. The third crosslink bridge 74 links the third protein 84 and fourth protein 86. Finally, the fourth crosslink bridge 76 links the fourth protein 86 and the first protein 80. As will be appreciated by those of skill in the art, the various proteins and bridges may extend in other directions to form a three-dimensional structure or mesh framework. The mesh structure 50 thus has a plurality of interior voids or openings 60 that have a representative rectangular shape in a regular repeating three-dimensional mesh pattern; however, the openings 60 are not necessarily limited to these shapes or positions and may have different shapes and arrangements within the mesh structure 50.

The openings 60 within the mesh structure 50 may be understood to have an average mesh size. Mesh size ($\xi$), also referred to as correlation length, can be understood to represent a maximum size of solutes/molecules that can pass through the mesh structure 50, where the dimensions of such a molecule are labeled 62 in FIG. 2. In certain aspects, an average linear mesh size ($\xi$) (e.g., represented by dimension 62) in the mesh structure 50 may be greater than or equal to about 1 nm to less than or equal to about 4 nm (e.g., from 1 nm to 3 nm, or from 2 nm to 4 nm, e.g., from 1 nm to 2 nm, from 2 nm to 3 nm, or from 3 nm to 4 nm, e.g., about 1 nm, about 2 nm, about 3 nm, or about 4 nm). Inside the openings 60 in the hollow cage-like mesh structure 50, it is possible to load a variety of therapeutic molecules, such as therapeutic active ingredients, biomolecules (e.g., nucleic acids (e.g., DNA, RNA) and/or proteins), enzymes, small molecules, imaging agents, and the like.

Thus, the average mesh size within protein nanoparticles is an important factor affecting controlled release of therapeutic agents or imaging agents. As will be described further below, the methods of electrohydrodynamic jetting used to fabricate polymerized protein nanoparticles permits tuning a crosslinking density, for example, by simply changing a ratio of crosslinking agent to protein in the particle formulation solution step without the need for any further post-fabrication modification. By way of non-limiting example, electrohydrodynamic jetting enables fine-tuning of mesh sizes of protein-based nanoparticles by simply changing the ratio of protein to crosslinking agent. In the case of ovalbumin, where the ratio of crosslinking agent to protein is increased from 10% to 50%, the mesh size in the nanoparticle (length scale, average spacing decreases from about 3.98+0.12 nm to about 2.15+0.01 nm. In certain aspects, the cross-linked water-soluble protein is present at greater than or equal to about 50% by weight to less than or equal to about 95% by weight (e.g., about 50% by weight, about 55% by weight, about 60% by weight, about 65% by weight, about 70% by weight, about 75% by weight, about 80% by weight, about 85% by weight, about 90% by weight, or about 95% by weight (e.g., dry weight) of the nanoparticle) and the crosslinking agent is present at greater than or equal to about 5% by weight to less than or equal to about 50% by weight (e.g., about 5% by weight, about 10% by weight, about 15% by weight, about 20% by weight, about 25% by weight, about 30% by weight, about 35% by weight, about 40% by weight, about 45% by weight, or about 50% by weight (e.g., dry weight) of the nanoparticle). In one variation, the cross-linked water-soluble protein is present at about 60% by weight and the crosslinking agent is present at about 40% by weight.

In some instances, a cross-linking agent providing a suitable mesh size has an average molecular weight from 100 kDa to 100,000 kDa (e.g., from 500 kDa to 50,000 kDa, or from 1,000 kDa to 25,000 kDa, e.g., from 100 kDa to 500 kDa, from 500 kDa to 1,000 kDa, from 1,000 kDa to 2,000 kDa, from 2,000 kDa to 5,000 kDa, from 5,000 kDa to 10,000 kDa, from 10,000 kDa to 20,000 kDa, from 20,000 kDa to 50,000 kDa, or from 50,000 kDa to 100,000 kDa, e.g., about 2,000 kDa, about 5,000 kDa, about 8,000 kDa, about 10,000 kDa, or about 20,000 kDa). In some instances, a cross-linking agent providing a suitable mesh size is a linear polymer (e.g., a bifunctional linear polymer) and has an average molecular weight from 100 kDa to 100,000 kDa (e.g., from 500 kDa to 50,000 kDa, or from 1,000 kDa to 25,000 kDa, e.g., from 100 kDa to 500 kDa, from 500 kDa to 1,000 kDa, from 1,000 kDa to 2,000 kDa, from 2,000 kDa to 5,000 kDa, from 5,000 kDa to 10,000 kDa, from 10,000 kDa to 20,000 kDa, from 20,000 kDa to 50,000 kDa, or from 50,000 kDa to 100,000 kDa, e.g., about 2,000 kDa, about 5,000 kDa, about 8,000 kDa, about 10,000 kDa, or about 20,000 kDa). In some instances, the cross-linking agent providing a suitable mesh size is a linear polymer (e.g., a bifunctional linear polymer) having an average molecule weight of about 2,000 kDa.

In certain variations, the nanoparticle comprises a water-soluble protein having an average molecular weight of greater than or equal to about 8 kDa to less than or equal to about 700 kDa, optionally greater than or equal to about 10 kDa to less than or equal to about 400 kDa. In some instances, the nanoparticle comprises a water-soluble protein having an average molecular weight from 8 kDa to 15 kDa, from 10 kDa to 20 kDa, from 15 kDa to 25 kDa, from 25 kDa to 50 kDa, from 50 kDa to 100 kDa, from 100 kDa to 200 kDa, from 200 kDa to 300 kDa, from 300 kDa to 400 kDa, from 400 kDa to 500 kDa, from 500 kDa to 600 kDa, or from 600 kDa to 700 kDa.

While a large variety of proteins can be used, in certain aspects, the protein is water-soluble (e.g., the un-crosslinked protein is water-soluble). Thus, the protein may be dissolved in water or carriers that are aqueous solutions that may comprise predominantly water. In certain aspects, proteins that are excluded from suitable proteins include transmembrane proteins, polytopic proteins that aggregate and precipitate in water, and proteins with a very high molecular weight, e.g., a molecular weight greater than 700 kDa, greater than or equal to about 750 kDa, or greater than or equal to about 800 kDa. In some instances, the protein of the nanoparticle is not laminin. In other instances, the protein is not fibronectin. In yet other instances, the protein is not laminin or fibronectin. In some instances, the protein of the nanoparticle is not a native matrix protein (e.g., not a naturally occurring extracellular matrix protein). Further, in certain aspects, small proteins with molecular weights less than 8 kDa are avoided, such as hirudin, which is only made up of 65 amino acids and has a molecular weight of about 6.7 kDa.

In certain aspects, the water-soluble protein having the desired molecular weight is selected from the group consisting of: albumin, ovalbumin, mucin, transferrin, insulin, lysozyme, hemoglobin, collagen, and combinations thereof. It should be noted that some of these proteins have varying molecular weights, so the protein selected desirably has a molecular weight in the range discussed above to ensure capability to be electrohydrodynamically jetted in an aqueous liquid, as will be described further below.

In certain aspects, the nanoparticle may further comprise a crosslinking agent reacted with the water-soluble protein. Prior to reacting with the water-soluble protein, the cross-linking agent may comprise a reactive group selected from the group consisting of: an alkenyl group, an alkynyl group, a maleimide group, an active ester group, an anhydride group, an N-succinimidyl group, a triflate group, and combinations thereof. In one variation, the crosslinking agent may be an amine-reactive crosslinker comprising a polyethylene glycol. For example, the crosslinking agent may be a homo-bifunctional polyethylene glycol crosslinker, O'-bis [2-(N-Succinimidyl-succinylamino)ethyl]polyethylene glycol (NHS-PEG-NETS), where the PEG units formed amide bonds with amino groups, such as lysine residues, in the water-soluble protein.

In certain other variations of the present disclosure, a nanoparticle may be substantially free of a distinct cross-linking agent and may be self-cross-linked. In such variations, the protein may be a relatively large water-soluble protein, for example, having an average molecular weight of greater than or equal to about 8 kDa to less than or equal to about 700 kDa. Further, the water-soluble proteins comprise disulfide bonds in their sequence to facilitate self-cross-linking. The cross-linked water-soluble protein may be selected from the group consisting of: albumin, ovalbumin, human serum albumin, bovine serum albumin, transferrin, hemoglobin, IgG, enzymes, transport proteins, storage proteins, antibodies, aptamers, chemokines, hormonal proteins, polypeptides, and combinations thereof. In certain variations, the self-cross-linked water-soluble protein defines a mesh structure, such as those described above.

Any of the nanoparticles described above may also comprise one or more additional active ingredients, imaging agents, or targeting moieties, by way of example, as will be discussed further herein. As noted above, these compounds or moieties may be disposed in the openings of a mesh structure defined by the cross-linked protein and optionally the crosslinking agent reacted thereto. In certain aspects, the protein-based nanoparticles comprise at least one therapeutic or pharmaceutically active ingredients, such as exclusive or generic pharmaceutical active ingredients/drugs, new chemical entities, and combinations thereof. In accordance with certain aspects of the present disclosure, the nanoparticles are suitable for use in a wide variety of biofunctional or bioactive applications. A "biofunctional" or "bioactive" substance refers to a chemical substance, such as a small molecule, macromolecule, metal ion, or the like, that causes an observable change in the structure, function, optical function, or composition of a cell when a cell is exposed to such a substance. Examples of observable changes include increased or decreased expression of one or more mRNAs, increased or decreased expression of one or more proteins, phosphorylation of a protein or other cell component, inhibition or activation of an enzyme, inhibition or activation of binding between members of a binding pair, an increased or decreased rate of synthesis of a metabolite, increased or decreased cell proliferation, changes in optical properties, and the like. In certain aspects, the nanoparticles of the disclosure deliver active ingredients to a target, in some embodiments, to tissue or an organ of an organism. In other aspects, the nanoparticles provide binding to certain target regions in an organism to modify optical or physical properties to improve diagnostic procedures. Various categories of active ingredients are discussed herein; however, it will be understood that while general attributes of each of the categories of components may differ, there may be some common attributes and any given material may serve multiple purposes within two or more of such listed classes or categories.

In various aspects, the protein-based nanoparticles according to certain aspects of the present disclosure fulfill one or more of the following advantages. First, the protein-based nanoparticles provide the ability to design drug delivery vehicles for various active ingredient types and concentrations. Second, the protein-based nanoparticles circulate and remain for long periods within the organism, thus avoiding filtration and removal, immune system recognition and/or complement activation. Third, the protein-based nanoparticles can provide an active targeting ability to deliver highly specific active ingredients to target tissues (for example, to a tumor site) to minimize systemic effects. This is particularly advantageous for chemotherapeutic treatments for cancer, where damage of attendant tissues can be minimized. Lastly, the protein-based nanoparticles can provide functional imaging that allows for distinguishing specific and non-specific binding.

The protein-based nanoparticles may comprise an active ingredient. An active ingredient is a compound or composition that diagnoses, prevents, or treats a physiological or psychological disorder or condition, or can provide a cosmetic or aesthetic benefit. In certain aspects, an active ingredient agent is targeted to a particular target, such as organs, tissues, medical implants or devices, hair, skin, mouth, eyes, circulatory system, and the like. For example, in various aspects, the nanoparticles having one or more active ingredients can be used in various pharmaceutical and/or cosmetic compositions. A "pharmaceutically and/or cosmetically acceptable composition" refers to a material or combination of materials that are used with mammals or other organisms having acceptable toxicological properties for beneficial use with such an animal. Pharmaceutically and/or cosmetically acceptable compositions include drug and therapeutic compositions, oral care compositions, nutritional compositions, personal care compositions, cosmetic compositions, diagnostic compositions, and the like.

In various aspects, the protein-based nanoparticles may be used in a wide variety of different types of compositions having a bio-functional or bioactive material and are not limited to the variations described herein. However, the present disclosure contemplates nanoparticles comprising one or more active ingredients that provides a diagnostic, therapeutic, prophylactic, cosmetic, sensory, and/or aesthetic benefit to an organism, such as a mammal. In certain aspects, an active ingredient prevents or treats a disease, disorder, or condition of hard or soft tissue in an organism, such as a mammal. As a non-limiting example, the current technology provides a method of treating a subject having cancer, the method comprising administering to the subject the protein-based nanoparticles in an effective amount to treat the cancer, wherein the cancer can be, for example, a carcinoma, a sarcoma, leukemia, a lymphoma, a myeloma, a germinoma, or a brain or spinal cord cancer (e.g., glioblastoma, diffuse astrocytoma). The cancer can be brain cancer, such as a glioma or astrocytoma, such as glioblastoma or diffuse astrocytoma, brain cancer, breast cancer, stomach cancer, colon cancer, rectal cancer, liver cancer, pancreatic cancer, lung cancer, cervical cancer, uterine cancer, ovarian cancer, prostate cancer, testicular cancer, bladder cancer, renal cancer, head and neck cancer, throat cancer, Hodgkin's disease, non-Hodgkin's lymphoma, multiple myeloma, leukemia, or skin cancer. In certain variations, the cancer is characterized by one or more intracranial tumors and may be a glioma or astrocytoma, such as diffuse astrocytoma or glioblastoma.

The ensuing description of suitable active ingredients is merely exemplary and should not be considered as limiting as to the scope of active ingredients that can be introduced into the protein-based nanoparticles according to the present disclosure, as all suitable active ingredients known to those of skill in the art for these various types of compositions are contemplated. Suitable active ingredients for use in such pharmaceutically and/or cosmetically acceptable compositions are well known to those of skill in the art and include, by way of example, pharmaceutical active ingredients found in the Merck Index, An Encyclopedia of Chemicals, Drugs, and Biologicals, Thirteenth Edition (2001) by Merck Research Laboratories and the International Cosmetic Ingredient Dictionary and Handbook, Tenth Ed., 2004 by Cosmetic Toiletry and Fragrance Association, each incorporated herein by reference. Each additional reference cited or described herein is hereby expressly incorporated by reference in its respective entirety. Certain suitable active ingredients, or pharmaceutically active ingredients or drugs, are known to those of skill in the art and include, but are not limited to, low-molecular weight molecules, quantum dots, natural and artificial macromolecules, such as proteins, sugars, peptides, DNA, RNA (including short interfering RNA (siRNA), e.g., siRNA against STAT3 or siRNA against ATG7).

A variety of low molecular weight molecules can be employed, particularly those having a molecular weight of less than about 10,000, optionally less than about 1,000, and optionally less than about 500. Suitable therapeutic active ingredients may include anti-proliferative agents; anti-rejection drugs; anti-thrombotic agents; anti-coagulants; antioxidants; free radical scavengers; nutrients; nucleic acids; saccharides; sugars; nutrients; hormones; cytotoxin; hormonal agonists; hormonal antagonists; inhibitors of hormone biosynthesis and processing; antigestagens; antiandrogens; anti-inflammatory agents; non-steroidal anti-inflammatory agents (NSAIDs); antimicrobial agents; antiviral agents; antifungal agents; antibiotics; chemotherapy agents; antineoplastic/anti-miotic agents; anesthetic, analgesic or pain-killing agents; antipyretic agents, prostaglandin inhibitors; platelet inhibitors; DNA de-methylating agents; cholesterol-lowering agents; vasodilating agents; endogenous vasoactive interference agents; angiogenic substances; cardiac failure active ingredients; targeting toxin agents; vitamins; nutraceuticals; and combinations thereof. The description of these suitable organic compounds/pharmaceutical active ingredients/new chemical entities is merely exemplary and should not be considered as limiting as to the scope of compounds or active ingredients which can be applied to a surface according to the present disclosure, as all suitable organic molecules and/or active ingredients known to those of skill in the art for these various types of compositions are contemplated. Furthermore, an organic compound may have various functionalities and thus, can be listed in an exemplary class above; however, may be categorized in several different classes of active ingredients.

By way of example, suitable active ingredient molecules include chemotherapeutic drugs, such as doxorubicin (molecular mass of about 543.5 g/mol); paclitaxel or Taxol™ (molecular mass of about 853.9 g/mol), cholesterol lowering drug, lovastatin (molecular mass of about 404.5 g/mol), NSAID analgesic ibuprofen (molecular mass of 206.3 g/mol). Quantum dots are optically active nanostructures, for example, cadmium tellurium (CdTe). Macromolecules include a wide range of compounds, generally including polymers and biomolecules having relatively large molecular weights. Such macromolecules can be naturally occurring or synthesized. Certain amino acids, peptides (amino acids liked via peptide bonds); polypeptides (linear chains of peptides), and even other and proteins (primary, secondary, and tertiary folded polypeptides), including enzymes are contemplated as active ingredients. Exemplary active ingredient proteins include heat shock protein 70 (HSP70) for dendritic cells and folic acid for cancer cells. Exemplary toxins for use as active ingredients include saporin and Botulinum toxins. Exemplary sugars include silyilic acid leucocytes and glucuronic acid, for example. In some aspects, the therapeutic active ingredient is a nanoparticle or nanocrystal having a particle size that is below the particle size of the protein-based nanoparticles. For example, the nanoparticles or nanocrystals may have a particle size of less than about 50 nm, optionally less than about 20 nm, and in some aspects, less than 10 nm. Useful active ingredient nanoparticles include magnetite ($Fe_3O_4$), magnesium oxide, and metal based nanoparticles, comprising gold, silver, and the like. In other embodiments, the protein-based nanoparticle does not include other nanoparticles (e.g., the protein-based nanoparticle may be substantially free of other nanoparticles (e.g., metal-based nanoparticles (e.g., metal oxide nanoparticles))).

In certain variations, the nanoparticle may comprise a therapeutic active ingredient is selected from the group consisting of: a drug, a steroid, and combinations thereof. In certain variations, the drug is selected from the group consisting of: paclitaxel, cis-platin, doxorubicin, and combinations thereof. In other variations, the therapeutic active ingredient is selected from the group consisting of a nucleic acid (e.g., DNA, RNA (e.g., mRNA, tRNA, rRNA, snRNA, or siRNA, e.g., siRNA against STATS, siRNA against ATG7), a plasmid, CRISPR CAS-9, or an aptamer), a protein or peptide (e.g., an antibody or other targeting molecule), a chemokine, a peptide drug, and combinations thereof.

In other variations, the active ingredient of the nanoparticles of the disclosure may be used for diagnostic purposes, and may be considered to be an imaging agent, such as in various diagnostic medical imaging procedures (for example, radiographic imaging (X-ray), fluorescence spectroscopy, Forster/fluorescent resonance energy-transfer (FRET), computed tomography (CT scan), magnetic resonance imaging (MM), positron emission tomography (PET), other nuclear imaging, and the like). Active imaging agents for use with diagnostic imaging include contrast agents, such as barium sulfate for use with MRI, for example or for example fluorescein isothiocyanate (FITC).

In other aspects, the protein-based nanoparticles may include other ingredients like polymers, dyes and colorants, inorganic ingredients including nanoparticles, nanomaterials, and nanocrystals, fragrances, and mixtures thereof.

In certain aspects, the protein-based nanoparticles can be provided in pharmaceutical compositions. In certain pharmaceutical compositions, the active ingredient is provided in a suitable pharmaceutical excipient, as are well known in the art. Thus, administration of protein-based nanoparticles in a pharmaceutical composition can be, for example, intravenous, topical, subcutaneous, transcutaneous, intramuscular, oral, intra-joint, parenteral, peritoneal, intranasal, by inhalation, or within or coating a medical device or implant. Pharmaceutical compositions are optionally provided in the form of solid, semi-solid, lyophilized powder, or liquid dosage forms, such as, for example, tablets, pills, capsules, powders, solutions, suspensions, emulsions, suppositories, retention enemas, creams, ointments, lotions, aerosols or the like, in unit dosage forms suitable for administration of precise dosages.

In accordance with certain aspects of the present disclosure, advanced design of protein-based nanoparticles can make them capable of promoting active ingredient delivery to a localized region, such as cancer targeting (e.g., intracranial tumor targeting, glioblastoma targeting). In certain aspects, the nanoparticles can serve as targeting elements for circulating blood cells carrying the active ingredient payload (e.g., chemotherapy drug) to a tumor. In certain embodiments, the protein-based nanoparticles can comprise a targeting moiety. For example, a targeting moiety, such as an antibody, a peptide, a ligand, or an aptamer, a liposome, a polysome, micelles, dendrimers, surface active agents (e.g., PEG-ylated or having a surface bearing a zwitterion), and the like, which may be conjugated with an active ingredient itself or with the nanoparticles loaded with an active therapeutic agent. A nanoparticle can be designed to have such properties by providing such materials within the material forming the protein-based nanoparticle, or may be provided by later treating, reacting, or coating the material forming the protein-based nanoparticle to achieve such properties.

In various aspects, the protein-based nanoparticles can deliver an effective amount of the active ingredient to a target region within an organism (e.g., a subject, such as a human subject). An "effective" amount of an active ingredient is an amount that has a detectable effect for its intended purpose and/or benefit. Preferably, the effective amount is sufficient to have the desired therapeutic, nutritional, cleansing, aesthetic, diagnostic, and/or prophylactic effect on the target region of an organism (e.g., a mammal) to whom and/or to which the composition comprising the protein-based nanoparticles is administered. The specific effective amount of the active ingredient, including appropriate dosages and concentrations, will vary with such factors as the composition in which the active ingredient is provided, the site of intended delivery, the route of administration, the particular condition or subject being treated, the nature of concurrent therapy (if any), the specific active used, the specific dosage form, and the carrier employed, all of which are well known to those of skill in the art.

The specific effective amount of the active ingredient desirably creates an observable change in the subject, such as increased or decreased expression of one or more mRNAs, increased or decreased expression of one or more proteins, increased or decreased cell proliferation, phosphorylation of a protein or other cell component, inhibition or activation of an enzyme, inhibition or activation of binding between members of a binding pair, an increased or decreased rate of synthesis of a metabolite, changes in optical properties, and the like. In certain aspects, the nanoparticles of the disclosure deliver active ingredients to a target, in some embodiments, to tissue or an organ of the subject/organism.

Preferably, the effective amount is sufficient to have the desired therapeutic and/or prophylactic effect (or other effects, like nutritional, cleansing, aesthetic, diagnostic, etc.) on the target region of the subject/organism (e.g., a mammal) to whom and/or to which the composition comprising the nanoparticles is administered. The specific effective amount of the active ingredient in the nanoparticle, including appropriate dosages and concentrations, will vary with such factors as the nanoparticle composition in which the active ingredient is provided, bioavailability, the site of intended delivery, the route of administration, the particular condition or subject being treated, the nature of concurrent therapy (if any), the specific active used, the specific dosage form, and the carrier employed, all of which are well known to those of skill in the art. In certain aspects, the In certain aspects, a safe and effective amount of an active ingredient in a nanoparticle is about 0.0001 to about 95 weight % of the total weight of the nanoparticle (on a dry basis). It should be noted that where the nanoparticle is distributed in a carrier or composition, that the overall concentration will be significantly less than in the nanoparticles. In certain aspects, the active ingredient is present in the nanoparticle at a concentration of about 0.001 to about 75% of the total nanoparticle weight. In other aspects, the active ingredient is present at from about 0.01 to about 20%; optionally of about 1% to about 20%; and optionally 5% to about 20%. However, as discussed above, the concentration of active ingredient is highly dependent on various factors well known to those of skill in the art, including required dosage for the target region, bioavailability of the active ingredient and the release kinetics of the phase in which the active ingredient is located, among others.

Thus, in certain instances, the nanoparticles of the invention can be used as part of a method of treating a subject having a cancer, e.g., a cancer characterized as having one or more intracranial tumors, e.g., diffuse astrocytoma or glioblastoma. Additionally or alternatively, the nanoparticles can be used as part of a method of treating a subject having a cancer (e.g., a cancer characterized as having one or more intracranial tumors, e.g., diffuse astrocytoma, glioblastoma) in combination with an additional therapeutic regimen, such as concurrent radiotherapy. The methods may involve administering an effective amount of a nanoparticle to a subject having cancer. An "effective" amount of a nanoparticle means that it delivers an active ingredient in an amount that has a detectable effect for its intended purpose and/or benefit.

In certain instances, the invention features a nanoparticle for use in a method of generating an anti-tumor cytotoxic T cell-mediated immune response, wherein the nanoparticle comprises albumin cross-linked in mesh structure, wherein the mesh structure encapsulates a therapeutic nucleic acid. The therapeutic nucleic acid is optionally an inhibitor of STAT3. In another variation, the therapeutic nucleic acid is an inhibitor of ATG7. In another aspect, the invention features a nanoparticle for use in a method of generating an anti-tumor humoral immune response, wherein the nanoparticle comprises albumin cross-linked in mesh structure, wherein the mesh structure encapsulates a therapeutic nucleic acid, wherein the therapeutic nucleic acid is an inhibitor of STAT3. In yet another aspect, the invention features a nanoparticle for use in a method of generating an anti-tumor humoral immune response, wherein the nanoparticle comprises albumin cross-linked in mesh structure, wherein the mesh structure encapsulates a therapeutic nucleic acid, wherein the therapeutic nucleic acid is an inhibitor of ATG7. For example, the nanoparticle may include a cell penetrating peptide, such as iRGD. In some embodiments, the cross-linked albumin is present at greater than or equal to about 50% by weight to less than or equal to about 95% by weight, and wherein a crosslinking agent is present at greater than or equal to about 5% by weight to less than or equal to about 50% by weight. In some embodiments, the therapeutic nucleic acid is siRNA against STAT3. In some embodiments, the therapeutic nucleic acid is siRNA against ATG7. In some embodiments, the mesh structure has an average linear mesh size of greater than or equal to about 1 nm to less than or equal to about 4 nm.

In certain aspects, a safe and effective amount of an active ingredient in a protein-based nanoparticle is about 0.001 to about 75 weight % of the total weight of phase (on a dry basis). It should be noted that where the nanoparticle is distributed in a carrier or composition, that the overall concentration will be significantly less than in the nanoparticle particles themselves. In other aspects, the active ingredient is present in the protein-based nanoparticles at from about 0.01 to about 50%; optionally of about 1% to about 40%; optionally of about 1% to about 20%; and optionally 5% to about 20%. However, as discussed above, the concentration of active ingredient is highly dependent on various factors well known to those of skill in the art, including required dosage for the target region, bioavailability of the active ingredient and the release kinetics of the protein-based nanoparticles in which the active ingredient is located, among others. By using electrohydrodynamic jetting to form the nanoparticles, as will be described in greater detail herein, a high loading of drug into the protein carrier is possible. Protein-based nanoparticles with active ingredient loadings above 50% are possible.

In yet other variations, a nanoparticle comprising a cross-linked water-soluble protein having an average molecular weight of greater than or equal to about 8 kDa and less than or equal to about 700 kDa and may comprise a biomolecule, such as DNA, RNA, plasmids, siRNA, mRNA, transfer RNA, ribosomal RNA, small nuclear RNA, single stranded DNA, CRISPR CAS-9, aptamers, antibodies, peptides, targeting molecules, vitamins, and any combinations thereof.

In certain other aspects, the present disclosure contemplates a method of making a nanoparticle. The method includes jetting a liquid through a nozzle. The liquid comprises a water-soluble protein having an average molecular weight of greater than or equal to about 8 kDa and less than or equal to about 700 kDa and water (e.g., water containing one or more solutes, e.g., buffers). The method also includes exposing the liquid to an electric field sufficient to solidify the liquid and form the nanoparticle defining a mesh structure having an average linear mesh size of greater than or equal to about 1 nm to less than or equal to about 4 nm. Thus, the methods provided herein may be considered to be electrified jetting, such as that disclosed by Roh et al. in "Biphasic Janus Particles With Nanoscale Anisotropy", Nature Materials, Vol. 4, pp. 759-763 (October, 2005), as well as in U.S. Pat. No. 7,767,017 to Lahann et al. The contents of each of these respective references are hereby incorporated by reference in their respective entireties. However, it should be noted that the techniques described in the Roh and Lahann et al. references pertain to polymers rather than proteins, as described herein.

Figure 3:
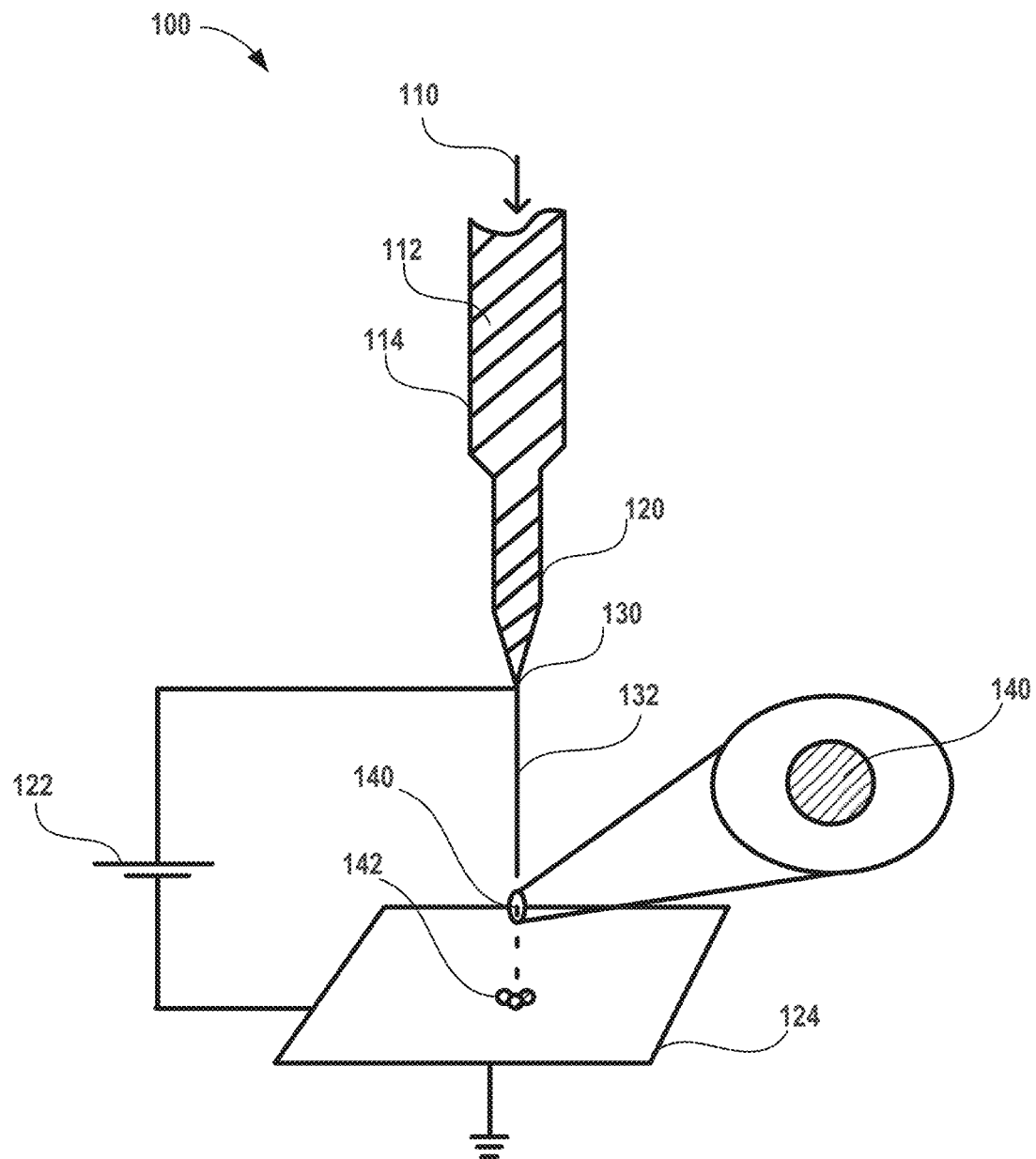
FIG. 3 shows an example of a schematic of an electrohydrodynamic jetting system for forming nanoparticles comprising a water-soluble protein in accordance with certain aspects of the present disclosure.

Electrified jetting is a process used to develop liquid jets having a nanometer-sized diameter, using electro-hydrodynamic forces. As shown in FIG. 3, an electrohydrodynamic jetting system 100 includes a source 110 of a liquid 112 contained in a channel 114 that is fed to a nozzle 120. A syringe pump (not shown) may be used to drive the liquids 112 into the nozzle 120. At the nozzle 120, a pendant droplet 132 is formed of conducting liquid 112. The nozzle 120 is in electrical communication with a power supply 122 that can be applied during the jetting operation. As shown, there is also an electrically conductive and grounded plate 124 disposed below and spaced apart from the nozzle 120. The power supply 122 is also in electrical communication with the plate 124. Thus, the droplet 130 is exposed to an electric potential of a few kilovolts generated by the power supply 122, where the force balance between electric field and surface tension causes the meniscus of the pendent droplet 130 to develop a conical shape, the so-called Taylor cone (not shown). Above a critical point, a highly charged liquid jet or ejected stream 132 is ejected from an apex of the cone.

In one variation, the electric field is generated by the potential difference between nozzle 120 and plate 124. Typically, an electric field is formed by applying a potential difference between at least two electrodes from about 0.1 kV to about 25 kV (e.g., from about 0.1 kV to about 0.5 kV, from about 0.5 kV to about 1.0 kV, from about 1.0 kV to about 5 kV, from about 5 kV to about 10 kV, from about 10 kV to about 15 kV, from about 15 kV to about 20 kV, or from about 20 kV to about 25 kV, e.g., about 0.1 kV, about 0.5 kV, about 1.0 kV, about 2.0 kV, about 5.0 kV, about 10 kV, about 15 kV, about 20 kV, or about 25 kV). Various configurations of plates and geometries may be used to generate the electric field as known to those of skill in the art and are contemplated by the present disclosure. In the variation shown in FIG. 3, the ejected stream 132 is fragmented due to instabilities generated by the electric field, thereby forming a spray of droplets 140 that form the protein-based nanoparticles 142. The solvents in the liquid 112 in the ejected stream 132 are rapidly removed (e.g., volatilized or evaporated) from the stream during the jetting process.

Morphological control can be achieved with the exemplary electric jetting formation methods described herein. Therefore, the ejected stream 132 exiting the nozzle 120 as a pendant droplet 130 can be fragmented to small droplets 140, instead of sustained and elongated jetting that leads to a continuous fiber. The size of the droplets 140 can also be controlled. Such control is attained by changing either the material properties of jetting liquids or the working parameters of electrified jetting that breaks-up the jet stream. It should be appreciated, however, that the final morphology of the ejected stream 132 is not always the same as those of the solid nanoparticle 142 products collected on the substrates. The shape of final nanoparticles 142 can also be controlled by a sol-gel transition process or by subsequent processing after formation by electric jetting.

Since the electrified jetting methods are related to electrohydrodynamic processes, the properties of the jetting liquid and operating parameters are interrelated. Moreover, when the jetting liquids are not one-component systems (i.e., mixtures of two or more compounds), the jetting liquid is a solution having properties governed by several parameters of the solvent and solutes. It should be appreciated that liquid properties, solution parameters, and operating parameters are related, as recognized by those of skill in the art. Relevant material properties include viscosity, surface tension, volatility, thermal and electrical conductivity, dielectric permittivity, and density. Relevant solution properties include concentrations, molecular weight, solvent mixtures, surfactants, doping agent, and crosslinking agents. Finally, relevant operating parameters include flow rate of the liquid streams, electric potential, temperature, humidity, and ambient pressure. With regard to the operating parameters, the average size and size distributions of the droplets 130 in electrospraying with cone-jet mode also are believed to be dependent on the flow rate (e.g., pumping rate of the jetting liquid). At a fixed flow rate, one or several relatively monodisperse classes of nanocomponent diameters are formed. At minimum flow rate, the modality of the distributions and diameter of the droplet itself also show their minima. When the flow rate is changed, the electric field can be adjusted by changing either distance or electric potential between the electrodes in order to sustain a stable cone-jet mode. Higher flow rates may be accompanied by a higher electrical field applied for mass balance of jetting liquids. When the diameter of droplets is larger than desired, solvent evaporation does not fully occur before the droplets reach the collecting substrate, so the resulting droplets may be wet and flat.

In various aspects, the use of the electric jetting methods provided herein afford greater control over the morphology and design of the protein-based nanoparticles as opposed to other methods of forming nano-components (such as precipitation, sonication during liquid jetting, and the like). One of the major differences between electrohydrodynamic cojetting of polymers, as had been done in the past, and protein nanoparticles is the fact that the components react with each other during jetting. For protein jetting, the initial solution was expected to be unstable and it was surprising and unexpected that polymer-containing solutions could be jetted.

In certain aspects, the liquid comprises water and optionally aqueous carriers. The liquid may include components that adjust pH, such as acids (e.g., acetic acid) or bases. In certain variations, the liquid may comprise a crosslinking agent. During the exposing, the water-soluble protein is at least partially cross-linked. However, the cross-linking may continue after the nanoparticle is formed and solidifies.

As noted above, the nanoparticle formed by such a process may comprise a cross-linked water-soluble protein that defines a mesh structure having an average linear mesh size of greater than or equal to about 1 nm to less than or equal to about 4 nm. In certain variations, the liquid further comprises an additive selected from the group consisting of: a therapeutic active ingredient, an imaging agent, a biomolecule, a targeting moiety, and combinations thereof. The additive is thus incorporated into the nanoparticle.

It should be noted that electrohydrodynamic jetting methods of proteins form different products from other techniques used to form protein particles. In the electrohydrodynamic jetting method, the droplets produced are sufficiently small that complete solvent evaporation over millisecond characteristic times does not require pre-heating of the solution or bath. The solid protein nanoparticles are collected on the grounded plate (e.g., plate 124). Consequently, there is no risk of thermally damaging dissolved labile molecules and the protein itself.

In contrast, there are different conventional methods to fabricate protein nanoparticles. In desolvation/coacervation, the addition of a "desolving" agent, such as ethanol or acetone, is required. The desolving agent then dehydrates the protein resulting in conformational change from a stretched to coil conformation. The proteins can be cross-linked, commonly by using glutaraldehyde, but the protein has undergone a conformational change that can be undesirable.

Protein nanoparticles can also be stabilized by denaturing the protein before desolvation, for example, by using a reducing agent such as BME ((3-mercaptoethanol). In other techniques, emulsification is used by mixing an aqueous protein solution with an immiscible oil or organic solvent solution, and sonicating the mixture. This causes the proteins to homogenize and form small droplets. The solvent/non-solvent is subsequently removed to yield nanoparticles. However, the sonication process can damage the native protein structure.

In yet other variations, thermal gelation is used by stirring proteins while they are being denatured at a high heat. The proteins unfold, aggregate, and then the growth of nanoclusters is stopped by immediately sinking them in an ice water bath. They can restabilize through disulfide bonds and hydrogen bonding.

In these methods, protein nanoparticle fabrication requires addition of alcohols, as moderately hydrophobic solvents, that destabilize the protein native structures, or they require a reducing agent such as BME that denatures the protein. In the emulsification, high sonication is required that can damage protein native structure. In the thermal gelation, the protein is denatured at a high heat.

However, by using the present electrohydrodynamic jetting methods, the protein-based nanoparticles may be substantially free of denaturing or conformational changes in the protein, aside from crosslinking. CD spectroscopy conducting on albumin-based nanoparticles prepared by such a technique show that albumin is not denatured in human serum albumin nanoparticles. Also in the case of ovalbumin nanoparticles, the particles still maintain their bioactivity after electrohydrodynamic jetting, which successfully results in activation of immune cells.

In certain aspects, a protein-based nanoparticle comprises a plurality of proteins. A majority of proteins maintain a predominantly native conformation. Proteins with a native conformation show similar or identical circular dichroism spectra to the proteins in the free state. In certain aspects, the majority of proteins that maintain a predominantly native conformation is greater than or equal to about 75% of the proteins in the nanoparticle, optionally greater than or equal to about 80% of proteins in the nanoparticle, optionally greater than or equal to about 85% of proteins in the nanoparticle, optionally greater than or equal to about 90% of proteins in the nanoparticle, optionally greater than or equal to about 95% of proteins in the nanoparticle, and in certain aspects, optionally greater than or equal to about 97% of proteins in the nanoparticle maintain a native confirmation of the free state of the protein.

Figure 4:
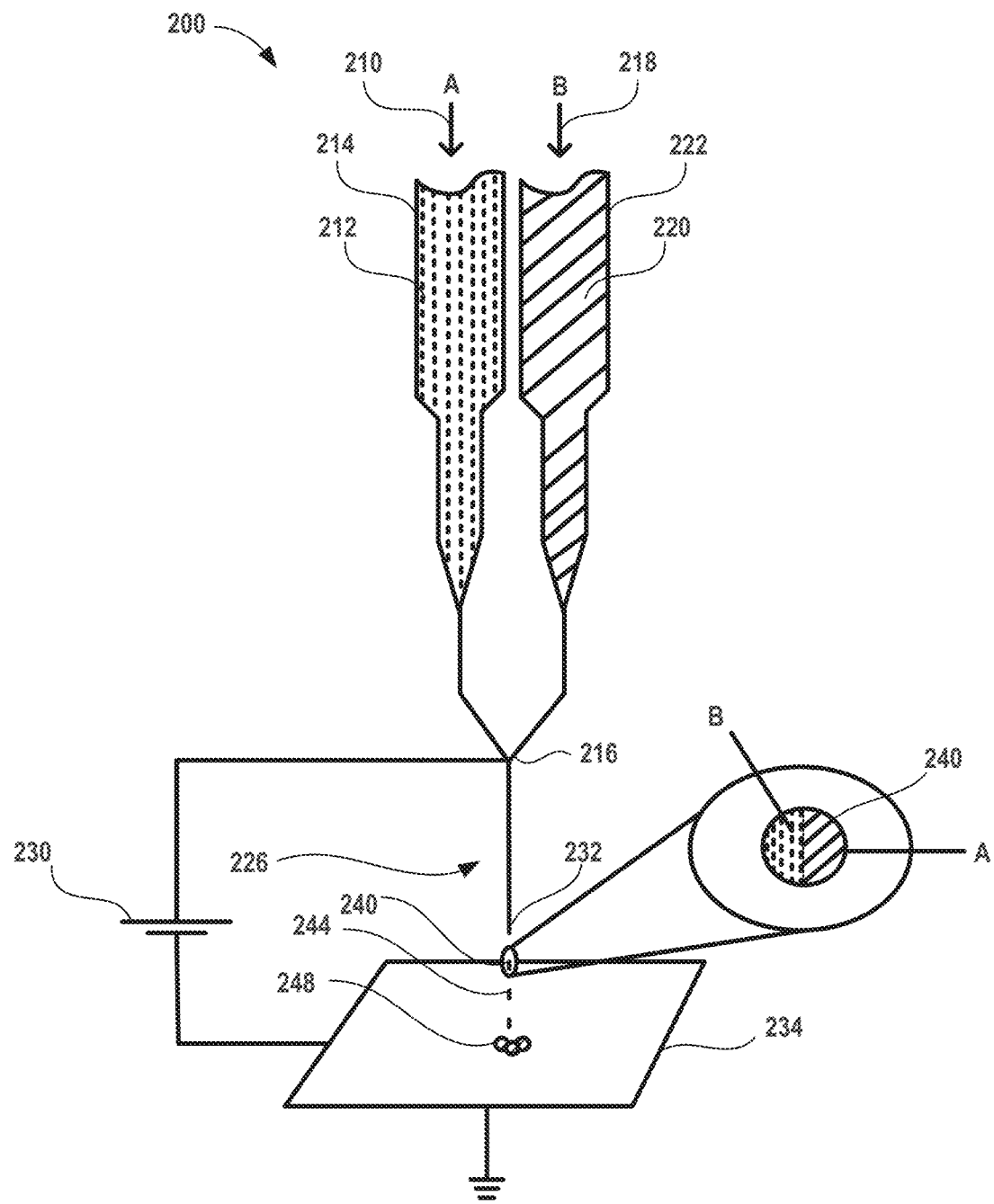
FIG. 4 shows another example of a schematic of an electrohydrodynamic jetting system for co-jetting and forming multicompartmental nanoparticles comprising water-soluble protein in at least one compartment in accordance with certain aspects of the present disclosure.

In certain other variations of the present disclosure, as shown in FIG. 4, an electrohydrodynamic jetting system 200 is used to form a multicompartmental protein-based nanoparticle. The design of the electrohydrodynamic jetting system 200 is modified from that shown in the electrohydrodynamic jetting system 100, because it involves a side-by-side electrojetting apparatus that provides at least two distinct liquid streams that are co-jetted together to form a multicompartmental nanoparticle. In order to incorporate two different liquid streams, a first source 210 of a first liquid 212 feeds a first channel 214 that is fed to a nozzle 216. A second source 218 of a second liquid 220 feeds second channels 222 that also feed into nozzle 216. The first and second channels 214, 222 are configured adjacent to each other (i.e., side by side) in nozzle 216. In some variations, first and second channels 214, 222 are capillaries. Thus, the first and second channels 214, 222 feed two different jetting liquid streams 212, 220 into a region 226 having an electric field generated by a power supply 230. First and second channels 214, 222 are of sufficient dimensions to allow contacting of liquids streams 212, 214 to form composite stream 232. In one variation, this electric field is generated by the potential difference between nozzle 216 and the electrically conductive and grounded plate 234. Like the electric field described above in the context of FIG. 3, the electric field is formed by applying a potential difference between the at least two electrodes from about 0.1 kV to about 25 kV. Various configurations of plates and geometries may be used to generate the electric field as known to those of skill in the art and are contemplated by the present disclosure.

A droplet 240 is exposed to an electric potential of a few kilovolts generated by the power supply 230 in the region 226, where the force balance between electric field and surface tension causes the meniscus of the pendent droplet 240 to develop a conical shape, the so-called Taylor cone (not shown). Like the process described above, at a critical point, a highly charged liquid jet or ejected composite stream 232 is ejected from an apex of the cone.

The ejected stream 232 is fragmented due to instabilities generated by the electric field, thereby forming a spray of droplets 244 that form the protein-based nanoparticles 246. The solvents in the first and second liquids 212 and 220 in the ejected stream 232 are rapidly removed (e.g., volatilized or evaporated) from the stream during the jetting process. In this manner, a plurality of multicompartmental protein-based nanoparticles 248 are formed. Each protein-based nanoparticle 248 includes a first compartment (see e.g., "A" in the precursor droplet 240) defining at least a portion of an exposed surface of the multicompartmental nanoparticle 248. The nanoparticle 248 also includes at least one additional compartment (see e.g., "B" in the precursor droplet 240) constituting (e.g., defining) at least a portion of an exposed surface and comprising at least one additional composition distinct from the first composition. By a distinct composition, it is meant at least one composition comprises a distinct chemical component or in certain alternative variations, the compositions may have the same constituents, but have differing amounts of the constituents. In certain variations, the first compartment may have the first composition comprising a water-soluble polymer having an average molecular weight of greater than or equal to about 8 kDa and less than or equal to about 700 kDa.

In certain variations, the first compartment may further comprise a crosslinking agent reacted with the water-soluble protein in the first compartment. The first composition may be any of those described above previously in the context of the single compartment nanoparticle having the cross-linked water-soluble protein. The one or more additional compartments may also have a protein and an optional crosslinking agent.

In one variation, the first composition in the first compartment comprises a water-soluble protein is selected from the group consisting of: ovalbumin, albumin, mucin, transferrin, insulin, lysozyme, hemoglobin, collagen, and combinations thereof. In certain variations, the at least one additional compartment also comprises a second water-soluble protein. The water-soluble protein may be provided in an aqueous liquid comprising water during the jetting process. The second water-soluble protein may be selected from the group consisting of: ovalbumin, albumin, mucin, transferrin, insulin, lysozyme, hemoglobin, collagen, and combinations thereof.

Each respective compartment can incorporate different: (i) active ingredients or drugs; (ii) different mesh sizes, so the release profile from each compartment can differ; and/or (iii) each crosslinking method can be different so the release of the active ingredient/cargo can be tuned. Further, one of the compartments can serve as an imaging modality (thus comprising an imaging agent), while the other serves as a drug carrier (thus comprising a therapeutic active ingredient). Further, in the case of antigen delivery, each compartment can be made from a different antigen, so multi-antigen delivery is possible. Furthermore, the surface of select compartments can be modified with different agents, stealth or cloaking moieties, or targeting moieties.

Various embodiments of the inventive technology can be further understood by the specific examples contained herein. Specific examples are provided for illustrative purposes of how to make and use the compositions, devices, and methods according to the present teachings and, unless explicitly stated otherwise, are not intended to necessarily be limiting or a representation that given embodiments have, or have not, been made or tested.

Example 1

Protein Nanoparticle Fabrication—Antigen-Based Nanoparticles

Ovalbumin (OVA) protein nanoparticles were prepared using electrohydrodynamic (EHD) jetting, as described above. Ovalbumin (Sigma Aldrich, USA) was dissolved in endotoxin-free water (G-Biosciences, USA) and run through endotoxin removal spin columns (ThermoFisher Scientific) according to manufacturer's instructions to provide endotoxin-free OVA. Then, OVA protein at 7.5 w/v % (g/ml) and poly(ethylene glycol)-based crosslinking agent (with molecular weight of 2 kDa NHS-PEG-NHS) with desired ratios (5, 10, 30 or 50 w/w protein %) are prepared in solvent mixture of water and ethylene glycol with ratios of 80:20 vol. % or 40:60 vol. % depending on the formulation. Then, the solution was mixed on the shaker until the crosslinker was fully dissolved. Afterwards, a syringe was filled with dissolved protein and crosslinking agent in water-ethylene glycol mixture. The syringe was capped with 26G needle, which was used as a capillary and placed into the pump. The solution was pumped at 0.1 mL/h. Upon formation of a droplet at the tip of the needle, the electric field was applied to the system. After applying approximately 10-12 kV of voltage, the droplet was distorted to a stable cone, Taylor cone, and formed a protein jet. The protein jet then split into individual droplets with higher surface area. This induced instantaneous evaporation of the solvent and resulted in solidification of the non-volatile components. Therefore, polymerized OVA nanoparticles were sprayed to the grounded collecting plate. The distance between the needle tip and the collector sheet was adjusted to 15 cm-20 cm.

By using homo-bifunctional polyethylene glycol crosslinker, O'-bis[2-(N-Succinimidyl-succinylamino)ethyl]polyethylene glycol (NHS-PEG-NHS) (Sigma Aldrich, USA) as a crosslinker, the PEG units formed amide bonds with amino groups in OVA such as lysine residues. To ensure completion of crosslinking reaction, OVA nanoparticles were kept at 37° C. for 7 days. This resulted in formation of stable, polymerized OVA nanoparticles. After stable nanoparticles were formed in solid phase, nanoparticles were collected in Endotoxin-Free Dulbecco's PBS (EMD Millipore, USA.) containing 0.01% Tween 20.

Parameters, such as protein concentration, solvent viscosity and solvent dielectric constant, can be adjusted to control the size and network structure in pNPs. To increase the size of hydrated OVA pNPs to 500 nm, the ratio of water-to-ethylene glycol was decreased to 40:60 (vol. %), which effectively decreased the overall dielectric constant of the solvent system and increased nanoparticle size. However, additional optimization was required to obtain 500 nm OVA pNPs. First, the PEG/OVA ratio was decreased to 5% (w/w). Second, the molecular weight of the PEG crosslinker was increased from 2 kDa to 20 kDa. Through these modifications, hydrated OVA pNPs with a size of 500 nm were reliably prepared, as confirmed by dynamic light scattering.

Using protein-based nanoparticles (pNPs) comprised of the actual antigen eliminates the need for a separate nanoparticle carrier. If the entire particle, or a majority of the particle, is comprised of antigen, pNPs have the potential for enhancing DC surface receptor engagement, prolonging tissue persistence, sustaining antigen activity and minimizing off-target material delivery. In the past, proteins have been assembled into particles through structurally ordered assembly, unstructured hydrophobic assembly and electrostatic assembly. However, the protein design must achieve self-assembly with desired materials physicochemical properties and desired immune interactions. Protein assembly through fusion and sequence modification are more affected by antigenic variability in their ability to self-assemble and preserve antigen recognition. Compared to fusion and sequence modification, chemical conjugation to other proteins, lipids or polymers, promises versatility and broader applicability to a wider spectrum of antigens, but requires multiple processing steps. For example, cross-linked peptide nanoclusters are fabricated for delivery of oncofetal antigen by desolvation and are stabilized through disulfide bonds. However, changes to the primary structure of the protein, such as addition of cysteine to the c-terminus of the peptide, is necessary to ensure successful crosslinking.

The pNPs comprised of polymerized ovalbumin (OVA) linked by poly(ethylene glycol) (PEG) units provide the ability to reduce off-target immune responses, because the target antigen becomes the main structural building block of the pNPs. This novel type of pNPs ensures presentation of dense arrays of antigen readily recognizable by antigen-presenting cells (APCs). In pNPs comprised of polymerized OVA, antigen presentation is influenced by the crosslinker: protein ratio. Specifically, the four types of polymerized OVA pNPs are evaluated with various PEG:OVA ratios in terms of their uptake by dendritic cells, T cell activation, lymphatic drainage, antibody production, and anti-tumor efficacy.

Characterization of PNPs

Scanning electron microscopy (SEM). SEM images were recorded using a FEI Nova 200 Nanolab SEM/FIB at the Michigan Center for Materials Engineering at acceleration voltages of 5 kV. Images were processed using ImageJ (Wayne Rasband, NIH) to obtain the respective nanoparticle size distribution. For particle size determination, >500 particles/sample were measured using ImageJ.

Dynamic/electrophoretic light scattering (DLS/ELS). DLS/ELS measurements were carried out using a Zetasizer Nano ZS (Malvern Panalytical). DLS was employed to measure the particle size distribution in PBS buffer after particle collection. ELS was employed to determine the zeta potential of OVA NPs. 3 individual measurements were carried out per sample and averaged to determine the particle size and zeta potential.

Atomic force microscopy (AFM). AFM measurements were carried out using an MFP-3D (Oxford Instruments, UK) using CSC-38noAl-A cantilevers (Micromash, USA) with a spring constant of 0.09 N/m. Samples were prepared by electrospraying OVA pNPs directly onto silicon substrates coated with poly(4-Penta fluorocphenyl-p-xylylene) via chemical vapor deposition (CVD) polymerization (see supporting information); the substrates were allowed to crosslink at 37° C. for several days prior to use. OVA NPs were localized by scanning the surface in tapping mode over a (5×5) μm$^2$ area and then decreasing the scan area for visualization of a single NP. The force curves were obtained by indenting the tip into the center of an individual nanoparticle and recording the deflection of the cantilever.

Small angle neutron scattering (SANS). SANS experiments were carried out at the NIST Center for Neutron Research using the NGB 30 instrument. Using neutron wavelength of λ=6 Å and Δλ/λ=0.11 at detector distances 1.3 m, 4.0 m, and 13.2 m, a q-range of 0.003 Å-1 to 0.5 Å-1 is provided. OVA pNPs with PEG/OVA ratio of 10% and 40% dispersed in D$_2$O (2 mg/mL) were loaded into 1 mm titanium scattering cells between mounted quartz windows, and a Julabo temperature-controlled bath was used to maintain the sample temperature at 37° C. SANS data were then collected and reduced using the NCNR IGOR software. Data analysis was performed subsequently using the Sasview software.

Preparation of bone marrow-derived dendritic cells (BMDCs). BMDCs were prepared according to literature protocols. C57BL/6 mice were kept in a pathogen-free environment and allowed to acclimate for at least one week before experiments. Briefly, femur and tibia were harvested from C57BL/6 mice. Bone marrow was flushed with a syringe and collected. The cell suspension was passed through a 40 µm cell strainer. After centrifugation, cells were plated into non-tissue culture treated Petri-dishes at a concentration of 2 million cells per dish in DC media (RPMI 1640 supplemented with 10% FBS, 1% penicillin-streptomycin, 50 µM β-mercaptoethanol and 20 ng/ml GM-CSF) at 37° C. with 5% $CO_2$. The media was refreshed on days 3, 6, and 8. BMDCs were used for experiments on days 10-12.

OVA pNP uptake by BMDCs. Internalization of fluorescent OVA pNPs by BMDCs was visualized using confocal microscopy and quantified using flow cytometry. Fluorescent OVA pNPs were obtained by addition of AlexaFluor 647-conjugated albumin from bovine serum (BSA) at 1 mg/ml to the solvent mixture for electrospraying of the nanoparticles. For confocal imaging, BMDCs were seeded on chamber slides (105 cells/well) and maintained in a humidified incubator at 37° C. and 5% CO2. Cells were incubated with 10 µg/ml of OVA NPs for 24 hours. The cells were then washed three times with PBS, fixed with 4% paraformaldehyde, washed, and permeabilized with 0.1% Triton-X solution that was followed by treatment with blocking solution of 1% BSA. The actin filaments were stained with AlexaFluor 488-Phalloidin and the nucleus was stained with DAPI. The samples were imaged using a 63× oil-immersion lens on a Nikon A-1 spectral confocal microscope located at the Microscopy and Image Analysis Laboratory (MIL) at the University of Michigan.

For quantitative uptake studies, flow cytometry was carried out. BMDCs were plated in a 12-well plate at a density of 1 million cells per well in DC media. After 24 hours, media was removed from the wells to remove non-adherent cells, and fresh media containing different nanoparticle groups at 10 µg/ml was added to the wells. After 24-hour incubation of cells with OVA nanoparticles, the cells were washed with PBS three times and then trypsinized. The cells were washed two more times and stained with DAPI before analyzing them via flow cytometry using a Cytoflex (Beckman Coulter) cell analyzer located at the Flow Cytometry Core of the University of Michigan. Data were analyzed using FlowJo software.

CFSE dilution assay. CFSE dilution assay was performed to evaluate the proliferation of OT-I CD8+ cells after co-culture with OVA pNP-treated BMDCs. BMDCs were seeded in 96-well plates at a density of 50,000 cells/well and then incubated with the respective OVA NPs groups, soluble OVA, SIINFEKL (positive control), and PBS (negative control) overnight. Naive CD8+ T cells were isolated from the spleen of OT-I transgenic mice using a magnetic CD8+ T-cell-negative selection kit. OT-I CD8+ cells were fluorescently labeled by incubation with CFSE (1 µM) for 10 min at 37° C. CFSE-labeled OT-I CD8+ T cells were then co-cultured with OVA pNP-treated BMDCs in 96 well plates at a density of 50,000 cells/well for 72 hours. BMDCs were washed with PBS three times before co-culture. Cells were then stained with CD8α-APC and DAPI, and flow cytometry (Cytoflex, Beckman Coulter) was used to determine the percentage of live, proliferated OT-I CD8+ cells. The data was processed using FlowJo software and reported as % CFSE dilution, which was proportional to OT-I CD8+ cell proliferation.

Immunization. Six-week-old, female C57BL/6 mice were purchased from Jackson Laboratory. Mice (n=5 per group) were immunized subcutaneously at the tail base at a dose of 10 µg OVA with 15 µg CpG in 100 µl sterile PBS buffer (primary immunization). Boost immunization was performed on day 21 after primary immunization. On days 20 and 42, blood was collected by submandibular bleed for serum antibody titers analysis. To separate serum, the collected blood was centrifuged at 10,000×g for 5 mins. Serum was then stored at −80° C. until analysis.

For ELISA analysis, 96 well flat bottom Immunoplates (Thermo Scientific) were coated with 1 µg/well OVA solution in 0.05 M carbonate-bicarbonate buffer (pH 9.6) and incubated overnight at 4° C. Plates were then washed with 50 mM Tris, 0.14 M NaCl, 10.05% Tween 20 (pH 8) followed by blocking with 50 mM Tris, 0.14 M NaCl, 1% BSA (pH 8) for 1 hour at room temperature. Samples were diluted in 50 mM Tris, 0.14 M NaCl, 0.05% Tween 20, 1% BSA and added to each well for an hour incubation at room temperature. After washing, the plates were incubated with diluted horseradish peroxidase enzyme (HRP) conjugated Rabbit anti-mouse IgG for an hour. The plates were then washed and incubated with TMB substrate solution for 10 minutes. The reaction was stopped by addition of 2 M $H_2SO_4$ solution. The plates were read at the wavelength of 450 nm using a plate reader.

Statistical analysis. All quantitative experiments were performed in triplicate and were presented as arithmetic mean±SEM. Statistical analysis were performed using SPSS Statistics 24 software. One-way ANOVA with Tukey's post-test was used to determine significance among groups. A P-value of <0.05 was considered statistically significant (*P<0.05, P<0.01, *P<0.001; ****P<0.0001); P-values of >0.05 were considered not significant (ns).

FIGS. 5A-5D show SEM images of the different OVA pNPs as collected on the counter electrode. FIG. 5A shows an ovalbumin nanoparticle with 10 w/w % NHS-PEG-NHS crosslinker (MW=2000 g/mol (2 k XL)), FIG. 5B shows 30 w/w % 2 k XL, FIG. 5C shows 50 w/w % 2 k XL fabricated with 80:20 vol. % ethylene glycol/water, and FIG. 5D shows 5 w/w % 20 k XL fabricated with 40:60 vol. % ethylene glycol/water.

The pNPs were dispersed in PBS buffer, and their size was measured using DLS. The size of hydrated nanoparticles characteristically increased with lower PEG/OVA ratio (FIG. 6A). The swelling of the particles with respect to their SEM dry size was estimated using $$\text{Swelling} = \frac{d_{DLS} - d_{SEM}}{d_{SEM}} \quad \text{(Equation 1)}$$

where dDLS and dSEM are the nanoparticle diameters obtained from DLS and SEM. As shown in the table in FIG. 6B, swelling ratios of 1.9, 2.1, 1.4 and 1.1 were calculated for the OVA pNPs with PEG/OVA ratios of 5, 10, 30 and 50%, respectively. Thus, OVA pNPs with PEG/OVA ratios of 5% and 10% increased their size by almost 200% after storage in PBS, whereas PEG/OVA ratios of 50% resulted in about 100% swelling. These differences in the swelling behavior suggest substantial differences in the mesh sizes of the protein gels of which the pNPs are comprised. The dependency of pNP swelling on crosslinker amount indicates that preparing protein-based nanoparticles in accordance with the electrohydrodynamic jetting methods, in fact, does yield particles with different mesh size. However, the mesh size is also quantified more accurately using small-angle neutron scattering to evaluate the network density of polymerized pNPs.

Mesh size of OVA pNPs. SANS measurements of two representative OVA pNPs, 10% and 50% PEG/OVA NPs dispersed in $D_2O$ (2 mg/mL) were taken. FIG. 6C shows SANS data and fits for the OVA pNPs with 10% and 50% XL. It was expected that the scattering from the hydrated protein network resembles the scattering from heterogeneous synthetic polymer hydrogels, which can be modeled as a disordered two-phase system with a protein-rich network phase and a protein-poor polymer phase. Accordingly, the scattering curves were fitted to a combined Porod model and the Debye-Anderson-Brumberger (DAB) model (solid black lines in FIG. 6C) according to $$I(q) = \frac{8\pi\Phi(1-\Phi)(\Delta\rho)^2\xi^2}{\left(1+(q\xi)^2\right)^2} + \frac{A}{q^4} \quad \text{(Equation 2)}$$

where A is a coefficient that determines the relative magnitude of Porod scattering. The DAB model (first term in equation (2)) describes scattering from the concentration correlations between the protein-rich phase with volume fraction 1 and scattering length density contrast $\Delta\rho$ with the surrounding fluid that is randomly distributed into domains of average spacing, i.e., mesh size ($\xi$). The Porod model (second term in equation (2)) represents scattering from smooth interfaces between the protein-rich and protein-poor domains.

Equation (2) provides fits of the observed SANS spectra from the two samples. At low q-values, a q-4 dependence of the scattering data is observed, consistent with scattering from a smooth interface. At moderate q-values, the length scale, or mesh size ($\xi$), is apparent as a shoulder in the scattering curve. It can be noted that the overall fit for 50% PEG/OVA pNPs is poor in the region where the Porod and the DAB model contributions are of similar magnitude (q~0.01-0.02 Å-1). The explanation for this lies in the interference between the Porod scattering from the interfaces of the protein-rich domains and the DAB scattering from polymer chains inside the domains. This is not accounted for in the model and would likely show up in the mid q-range, where the model gives a poor fit.

The DAB scale factor $(8\pi\Phi)(1-\Phi)(\Delta\rho)2$ increases fourfold as the PEG/OVA ratio increased from 10% to 50%, confirming the densification of the protein network as the degree of crosslinking increases. Furthermore, the average spacing $\xi$ decreases nearly two-fold as the PEG/OVA ratio increases from 10% to 50% (Table 1), thus revealing a more finely divided structure with increasing PEG/OVA ratio. Together, these results suggest that the protein network becomes denser and more finely heterogeneous with increasing PEG/OVA ratio, consistent with a more porous but smaller mesh structure at higher crosslink density.

TABLE 1

|  | 10% PEG/OVA | 50% PEG/OVA |
|---|---|---|
| Porod scale factor, A | $3.70 \times 10^{-9} \pm 2.99 \times 10^{-13}$ | $5.92 \times 10^{-9} \pm 1.02 \times 10^{-13}$ |
| DAB scale factor, $8\pi\Phi(1-\Phi)(\Delta\rho)2$ | $4.92 \times 10^{-6} \pm 1.32 \times 10^{-7}$ | $31.95 \times 10^{-5} \pm 1.60 \times 10^{-7}$ |
| Correlation length (mesh size ($\xi$), (nm) | $3.98 \pm 0.12$ | $2.15 \pm 0.01$ |

The uptake of polymerized OVA pNPs by BMDCs was evaluated quantitatively by flow cytometry (FIG. 7A) and further visualized by confocal microscopy (FIGS. 7B-7E). For this purpose, OVA pNPs were fluorescently labeled by adding AlexaFluor 647-conjugated albumin from bovine serum (BSA) to the OVA electrospraying solutions. The fluorescence intensity of OVA NPs (10 µg/ml) was quantified using a plate reader; no significant differences in fluorescence intensity between the different nanoparticle groups was found. Next, OVA pNPs were incubated with BMDCs for 24 h at a concentration of 10 µg/ml. Cellular uptake was quantified using flow cytometry by comparing the mean fluorescence intensity (MFI) values. The data show that there is a difference in the MFI values for OVA pNPs with different crosslinking density. MFI values are increased for pNPs with lower PEG/OVA ratio (10%), which correlate with higher cellular uptake, compared to the other groups. Cells incubated with pNPs with a 10% PEG/OVA ratio showed 6.9-fold greater MFI than those exposed to pNPs comprised of 50% PEG/OVA (P<0.0001). However, MFI values for cells incubated with pNPs with 5% and 10% PEG/OVA ratios were not statistically different (P>0.05). It has been shown previously that the elasticity of nanoparticles affects cellular uptake: Nanoparticles with Young's moduli between 30 and 140 kPa show the highest uptake by RAW 264.7 macrophages, while softer (<30 kPa) or harder (>140 kPa) NPs show reduced uptake. Here, pNPs with PEG/OVA ratios of 5% and 10%, which had intermediate elasticity as indicated by E moduli of E=43 kPa are associated with the highest levels of cellular uptake.

Antigen cross-presentation by OVA pNPs. Eliciting an effective immune response requires delivery of OVA to antigen-presenting cells (APCs), such as dendritic cells (DCs). DCs digest OVA through a process called cross-presentation, which results in the activation and proliferation of CD8+ T cells. Thus, the ability of OVA pNP-treated BMDCs to promote antigen cross-presentation and induce antigen-specific proliferation of OT-I CD8+ cells were evaluated using a CFSE dilution assay (FIGS. 3F and 3G). CFSE dilution was proportional to the proliferation of OT-I CD8+ cells. Therefore, BMDCs were first incubated with OVA pNPs or soluble OVA (control) at 10 µg/mL for 24 h. BMDCs were then co-cultured with CFSE-labeled naïve OT-I CD8+ T cells, which recognize the OVA-derived epitope SIINFEKL presented in the context of MHC-I H2Kb. After 72 h of co-culture, the population of proliferated CD8+ T cells was assessed using flow cytometry. Proliferation was affected by the PEG/OVA ratios of the pNPs. The OVA pNPs with PEG/OVA ratio of 5% showed 4.4-fold (P<0.0001) higher proliferation rates than pNPs with a 50% PEG/OVA ratio. Similarly, pNPs with PEG/OVA ratio of 10% showed 3.6-fold (P<0.001) higher proliferation rates than pNPs comprised of 50% PEG/OVA. Cross-priming and proliferation of the OT-I CD8+ cells were significantly enhanced for OVA pNPs with 5% (P<0.0001), 10% (P<0.0001) and 30% (P<0.01) PEG/OVA ratios as compared to solute OVA (FIG. 3A). While all pNP groups outperformed solute OVA, 5% and 10% PEG/OVA pNPs were most efficient in promoting antigen cross-presentation and proliferation of OT-I CD8+ cells. This result suggests (1) greater uptake of 5% and 10% PEG/OVA pNPs by BMDCs and (2) facilitating the processing of OVA pNPs by BMDCs due to lower crosslinking density and larger size of 5 and 10% PEG/OVA pNPs. There is some evidence that larger particles can direct antigen to the class I antigen presentation pathway more efficiently, which might explain the higher proliferation values for 5% PEG/OVA pNPs (500 nm vs. 200 nm). Once internalized by BMDCs, smaller particles are shuttled more rapidly to an acidic environment than larger ones, which can lead to fast and unregulated degradation and inefficient cross-presentation. Larger particles remain longer in a neutral environment, thus preserving the antigens for more efficient cross-presentation. The results here indicate that the PEG/OVA (protein to crosslinking agent) ratio is an important parameter for enhancing proliferation of CD8+ T cells, lower PEG/OVA ratios resulting in higher proliferation rates.

Humoral immune responses after subcutaneous delivery of OVA pNPs. In vivo performance of the pNPs was evaluated by evaluating their ability to induce humoral immune responses in mice. Following a prime-boost vaccine regimen shown in FIG. 8A, C57BL/6 mice were injected subcutaneously at the tail base with OVA pNPs of varying PEG/OVA ratio (10, 30, 50%) and size (200 nm, 500 nm) or solute OVA (10 µg OVA/100 µL dose), co-administered with CpG (15 µg/dose). Boost immunization was performed on day 21 after primary immunization. Anti-OVA serum IgG responses were measured on days 20 and 42 using an ELISA assay. Compared to soluble OVA, pNPs with a 10% PEG/OVA ratio elicit 49.4-fold in anti-OVA serum IgG titers (P<0.0001) and 9.1-fold increase in boost immunization (P<0.05), respectively. These pNPs also outperformed pNPs comprised of 50% PEG/OVA, as indicated by a 1.9-fold increase in anti-OVA serum IgG titers after prime immunization (P<0.01). The results show that 2 doses of OVA pNPs administered in a prime-boost regimen elicited stronger humoral immune responses than the equivalent doses and regimen of soluble OVA (FIGS. 8B-8C). While the larger, 5% PEG/OVA pNPs showed stronger CD8+ T cell responses in vitro, the same particles elicited a weaker humoral immune response in vivo (comparable to soluble OVA). Because the elasticity of 5 and 10% PEG/OVA pNPs is similar, the weaker humoral immune response of 5% PEG/OVA pNPs can be attributed to their larger size (500 nm). Larger pNPs may have limited lymphatic drainage due to extended tissue persistence at the injection site.

OVA pNPs delivery to lymph nodes. Next, the pNPs targeting of the draining lymph nodes using AlexaFluor 647-labeled pNPs was evaluated. OVA pNPs of varying PEG/OVA ratio (10, 30, 50%) and size (200 nm, 500 nm) were injected subcutaneously at the tail base of C57BL/6 mice (10 µg OVA/100 µL dose). The inguinal draining lymph nodes were harvested 48 hours after injection. Single-cell suspensions from the draining lymph nodes were prepared and pNPs uptake among the different populations of antigen-presenting cells were analyzed (dendritic cells, macrophages and B cells) using flow cytometry by comparing the MFI values of the cells. It was found that the MFI values of F4/80+ macrophages, B220+ B cells and CD11c+ DCs (FIGS. 8D-8F) increased with decreasing PEG/OVA ratio for the smaller (200 nm) pNPs with 10%, 30% and 50% PEG/OVA ratio. The MFI values of cells with larger (500 nm) 5% PEG/OVA pNPs were significantly lower, indicating that the pNPs were not delivered to draining lymph nodes efficiently due to their larger size. In the past, many different particle sizes have been studied with respect to their lymphatic drainage. It has been shown that particles exceeding 500 nm can be trapped at the injection site. Nanoparticles smaller than 10 nm, or soluble antigen, diffuse into the lymphatic system easily, but their retention time in the lymph nodes is too short to provide sustained antigen delivery. This may explain why OVA pNPs with 500 nm size and soluble OVA are not delivered to the lymph nodes efficiently, while improved NP uptake by lymph node cells is observed for the smaller OVA pNPs. For smaller pNPs sizes, improved uptake is observed for pNP with lower PEG/OVA ratio.

Therapeutic efficacy of pNPs in a model of melanoma. Encouraged by the fact that OVA pNPs with 10% PEG/OVA ratio result in increased OT-I CD8+ cell proliferation in vitro, improved uptake by APCs (both in vitro and in vivo), and enhanced humoral immune response in vivo, a murine model of B16F10-OVA melanoma was employed to evaluate the therapeutic efficacy of pNPs with a PEG/OVA ratio of 10% compared to solute OVA. Tumor-bearing mice were treated with 10% PEG/OVA pNPs or solute OVA (10 µg OVA/100 µL dose), co-administered with CpG (15 µg/dose). Following the regimen shown in FIG. 9A, C57BL/6 mice (10 mice/treatment group) were inoculated with 1×105 B16F10-OVA cells in the SC flank on day 0. Treatments with either 10% PEG/OVA pNPs or solute OVA were initiated on day 7 after tumor inoculation. A second treatment was given on day 14. Mice were euthanized after their tumors reached 15 mm in any dimension. FIG. 9B shows percentage of animal survival versus days after inoculation of tumor cells. Compared to the no treatment control group, mice treated with solute OVA showed slightly better survival. More than 50% of mice treated with solute OVA were euthanized due to large tumor burden on day 20, and 100% of the mice were euthanized on day 21. In contrast, 100% of mice treated with 10% PEG/OVA pNPs were alive on day 21 and showed improved survival until the endpoint of the study (day 24).

In this example, electrohydrodynamic electrospraying is a scalable and versatile nanoparticle manufacturing process, for development of protein-based nanoparticles (pNPs), such as ovalbumin (OVA) pNPs with defined physicochemical properties. The size or crosslinking agent to protein ratio is a parameter that can determine the immunological responses of pNPs. Specifically, lower PEG/OVA ratios result in softer pNPs with larger mesh sizes, which, in turn, can result in improved CD8+ T cell activation in vitro and improved lymph node drainage and humoral immune response in vivo. Identifying the significance of these parameters allows a pNP formulation to be designed with preclinical potential. In a preclinical murine model of melanoma, the smaller (200 nm) pNPs of 10% PEG/OVA ratio resulted in improved survival of mice bearing advanced melanoma tumors. It is envisioned that a combination strategy using different types of immunotherapies can be employed. In this case, a combination of OVA pNP administration with adjuvant therapy and immune checkpoint inhibitor therapy could result in further improved preclinical outcomes.

Example 2

Size Tunability—Crosslinking Agent Length

Nanoparticles are collected using endotoxin-Free Dulbecco's PBS (EMD Millipore, USA.) containing 0.01% tween 20.5 ml of Endotoxin-Free PBS with 0.01% tween 20 is poured into the particle collection plate. A plastic razor blade is used to scratch the surface of the plate and transfer the particles to the buffer. The collected OVA nanoparticles are fully dispersed using a micro-tip sonication, while the tube is submerged in mixture of ice and water in a small beaker to avoid temperature increase caused by tip sonication. The dispersed nanoparticles are passed through a 40 µm filter. Serial centrifugation steps are used to purify the nanoparticles at the target size. For size separation of 200 nm particles, the filtered solution of nanoparticles are then centrifuged at 4000 rpm for 5 minutes to remove the larger particles. The supernatant that containing the desired size of nanoparticles is centrifuged at 14000 rpm for 60 mins. The pellet is washed with endotoxin free PBS and re-dispersed in 1 ml endotoxin free PBS to be stored at fridge. Samples are made from the stock of nanoparticles for further characterization by dynamic light scattering and BCA assay.

For 500 nm size separation of OVA nanoparticles, the collected nanoparticles are centrifuged at 1,000 rpm for 1 min. the supernatant is centrifuged for 1 min at 10,000 rpm. The pellet is washed with endotoxin free PBS and re-dispersed in 1 ml endotoxin free PBS to be stored at fridge. Samples are made from the stock of nanoparticles for further characterization by dynamic light scattering and BCA assay.

Example 3

Stiffness Tunability—Crosslinking Agent to Protein Ratio

The chemical amide bond bridging between reactive NHS groups of the crosslinker and amine groups of OVA protein forms a mesh-like structure throughout the stable OVA nanoparticles. To tune the stiffness of nanoparticles, different ratios of crosslinker to protein can be used during the fabrication step. This approach results in producing OVA nanoparticles with different Young's modulus, for example, ranging from 42.7 kPa to 837.8 kPa for 5% crosslinking to 50% crosslinking.

Atomic force microscopy (AFM). AFM measurements are carried out using an MFP-3D (Oxford Instruments, UK) using CSC-38noAl-A cantilevers (Micromash, USA) with a spring constant of 0.09 N/m. Samples are prepared by electrospraying OVA nanoparticles directly onto silicon substrates coated with poly(4-Penta fluorophenyl-p-xylylene) via chemical vapor deposition (CVD) polymerization (see supporting information). The substrates are allowed to crosslink at 37° C. for several days prior to use. OVA nanoparticles are localized by scanning the surface in tapping mode over a (5×5) µm$^2$ area and then decreasing the scan area for visualization of a single NP. The force curves are obtained by indenting the tip into the center of an individual nanoparticle and recording the deflection of the cantilever. Through AFM indentation measurements the elastic moduli of OVA nanoparticles are obtained.

Example 4

Mesh Size—Crosslinking Density

As noted above, the mesh size of protein nanoparticles is an important factor affecting controlled release of the cargo from nanocarriers. Employing EHD jetting to fabricate polymerized protein nanoparticles, as is described herein, allows tuning the crosslinking density by simply changing the crosslinker to protein ratio in the particle formulation solution step without the need of any further post-fabrication modification. For OVA nanoparticles, PEG/OVA ratio of 10% and 50% are fabricated. The network density of these two nanoparticle groups are evaluated using small-angle neutron scattering. The results show that average spacing decreases nearly two-fold, forming a more finely divided structure as the PEG/OVA ratio increases from 10% to 50%. Therefore, the protein network becomes more porous and finely heterogeneous with smaller mesh structure with a higher PEG/OVA ratio. The dependency of OVA nanoparticle mesh size on crosslinking agent amount indicates that disclosed electrospraying procedure, in fact, allows for control of the mesh size in the nanoparticles formed.

Example 5

Mucin Particles

By using EHD jetting, with the same procedure disclosed in the present disclosure, mucin-based nanoparticles are fabricated with and without homo-bifunctional PEG-based crosslinker. Mucin protein is dissolved in ultra-pure water at 5 w/v %. In the case of cross-linked mucin particles, a NHS-PEG-NHS crosslinking agent at 10 w/w protein % relative to mucin protein is fully dissolved in water. Then, in both cases, ethylene glycol is added to achieve 80:20 vol. % water-ethylene glycol ratio. Then the final jetting solution is injected through syringes tipped with 26 gauge needles at 0.1 mL/h using a syringe pump. The distance between the tip of the needle and grounded collection plate is 15 cm. The morphology of nanoparticles is characterized using SEM. If NHS-PEG-NHS is used as crosslinker, mucin nanoparticles are kept at 37° C. for 7 days for the completion of crosslinking reaction. Both cross-linked and non-cross-linked mucin nanoparticles are separately collected in PBS. Hydrodynamic diameter and stability of nanoparticles both with and without crosslinker are measured using DLS. Both approaches resulted in stable mucin nanoparticles.

Example 6

Blood Brain Barrier (BBB) Transport—Receptor Targeted Material Choice Transferrin Particles)

Instead of modifying nanoparticles with transferrin antibody, by using EHD jetting, nanoparticles are created entirely from transferrin protein that ensures denser presentation of transferrin protein to enhance its recognition by brain endothelial cells. A similar EHD procedure for forming protein nanoparticles discussed in this disclosure is used to fabricate transferrin-based nanoparticles at 200 nm and 500 nm size. In the in vitro BBB model using monolayers of human brain endothelium (hCMEC/D3), the uptake and permeability of a library of nanoparticles are tested. The library of nanoparticles includes 50, 100, 200, 500 nm diameter sphere polystyrene nanoparticles, 2AR and 5AR rod-shape polystyrene nanoparticles, 200 and 500 nm transferrin nanoparticles, 200 and 500 nm human serum albumin nanoparticles, 200 and 500 nm liposomes. 500 nm transferrin particles show the highest uptake among all 500 nm nanoparticle analyzed and also experience one of the highest particle permeabilities across the BBB model. Interestingly, 200 nm transferrin (TF) nanoparticles show the highest permeabilities among the other 200 nm particles, besides the hydrogel-based particles. This could suggest that 500 nm TF, and 200 nm TF, access a specialized transcytotic pathway, as hCMEC/D3 cells are known to overexpress transferrin receptors.

Example 7

Insulin Nanoparticles

By using EHD jetting, insulin-based nanoparticles are fabricated. Insulin protein at 10 w/v %. and poly(ethylene glycol)-based crosslinker (NHS-PEG-NHS) at 10 w/w protein % are prepared in solvent mixture of water, acetic acid, and ethanol with ratios of 80:10:10 vol. %, respectively. Then the final jetting solution flows through syringes tipped with 26-gauge needles at 0.1 mL/h using a syringe pump. The distance between the tip of the needle and grounded collection plate is 15 cm. The morphology of nanoparticles is characterized using SEM. Hydrodynamic diameter and stability of nanoparticles are measured using DLS. This approach results in the formation of stable insulin nanoparticles.

Example 8

Lysozyme Nanoparticles

By using EHD jetting in accordance with certain aspects of the present disclosure, lysozyme-based nanoparticles are fabricated. Lysozyme protein at 10 w/v %. and poly(ethylene glycol)-based crosslinker (NHS-PEG-NHS) at 10 w/w protein % are prepared in solvent mixture of water, and ethanol with ratios of 90:10 vol. %, respectively. Then the final jetting solution is flown through syringes tipped with 26-gauge needles at 0.1 mL/h using a syringe pump. The distance between the tip of the needle and grounded collection plate is 15 cm. The morphology of nanoparticles is characterized using SEM. Hydrodynamic diameter and stability of nanoparticles are measured using DLS. This approach resulted in stable lysozyme nanoparticles.

Example 9

Hemoglobin Nanoparticles

By using EHD jetting in accordance with certain aspects of the present disclosure, hemoglobin-based nanoparticles are fabricated. hemoglobin protein at 10 w/v %. and poly(ethylene glycol)-based crosslinker (NHS-PEG-NHS) at 10 w/w protein % are prepared in solvent mixture of water, and ethanol with ratios of 90:10 vol. %, respectively. Then the final jetting solution in injected through syringes tipped with 26-gauge needles at 0.1 mL/h using a syringe pump. The distance between the tip of the needle and grounded collection plate is 15 cm. The morphology of nanoparticles is characterized using SEM. Hydrodynamic diameter and stability of nanoparticles are measured using DLS. This approach resulted in stable hemoglobin nanoparticles.

Example 10

Bicompartmental Protein Nanoparticles-Hemoglobin/Insulin Nanoparticles

By using EHD co-jetting in accordance with certain aspects of the present disclosure, bicompartmentalized hemoglobin/Insulin nanoparticles are fabricated. In electrohydrodynamic co-jetting, two 26G needles are used as capillaries in a side-by-side configuration. The two different protein solutions are pumped at a rate forming laminar flow to ensure a stable interface between the two jetting solutions without any convective mixing. When a droplet is formed at the outlet of the needles, the electric field is applied to the system. Due to rapid evaporation, the initial flow-determined configuration is maintained.

The two solutions are made as follows. In solution A, hemoglobin protein at 10 w/v %. and poly(ethylene glycol)-based crosslinker (NHS-PEG-NHS) at 10 w/w protein % are prepared in solvent mixture of water, and ethanol with ratios of 90:10 vol. %, respectively. In solution B, insulin protein at 10 w/v % and poly(ethylene glycol)-based crosslinker (NHS-PEG-NHS) at 10 w/w protein % is prepared in solvent mixture of water, acetic acid, and ethanol with ratios of 80:10:10 vol. %, respectively. Then one syringe is filled with solution A and the other is filled with solution B. The syringes are then tipped with 26-gauge needles and are placed in a side-by-side configuration in the syringe pump flowing at 0.1 mL/h. The distance between the tip of the needle and grounded collection plate is 15 cm. The applied voltage required to achieve and maintain a stable cone ranged from 10-12 kV. The morphology of nanoparticles is characterized using SEM and SIM. Hydrodynamic diameter and stability of nanoparticles are measured using DLS. This approach resulted in stable bicompartmental hemoglobin/insulin nanoparticles.

Example 11

Albumin-Based Protein Nanoparticles

Albumin protein nanoparticles are prepared using EHD jetting. Human serum albumin (HSA) is dissolved in co-solvent system consisting of ultra-pure water ($H_2O$) and ethylene glycol (EG). Separately, a 2 kDa homo-bifunctional polyethylene glycol crosslinker, O'-bis[2-(N-Succinimidyl-succinylamino)ethyl]polyethylene glycol (NHS-PEG-NHS), is quickly dissolved in ultra-pure water. Combining the two solutions, the final albumin concentration is brought to 7.5 w/v %, while the resulting NHS-PEG-NHS concentration is 10 (w/w protein) % relative to the total albumin. The final co-solvent system comprises an 80:20 vol. % mixture of $H_2O$:EG. The final protein jetting solution is loaded into a syringe, capped with a 26G stainless steel, blunt-tip needle, and placed into syringe pump to precisely control the flow rate.

The positive electrode of a 30 kV power supply is attached to the stainless steel needle, while the aluminum collection surface is grounded and maintained at a distance of 15 cm from the needle tip. The solution is pumped at 0.2 mL/h. Upon the formation of a droplet at the tip of the needle, an electric field is applied, distorting the droplet, forming a Taylor cone. The applied voltage required to achieve and maintain a stable cone ranged from 10-12 kV. Rapid acceleration of a viscoelastic jet in the electric field toward the grounded collection surface leads to size reduction of the resulting jet by several orders of magnitude, facilitating rapid solvent evaporation and solidification of the non-volatile components into spherical nanoparticles. Incorporating the bifunctional NHS ester crosslinker into the jetting solution, the PEG units form stable intermolecular amide bonds through polycondensation reactions with albumin lysine residues. Storage of the nanoparticles in their dry state for a period of seven days at 37° C., completes the crosslinking process, resulting in water-stable, albumin-based protein nanoparticles.

Example 12

Tumor-Targeting Protein Nanoparticles

Fabrication of tumor-targeting albumin nanoparticles follows a similar approach to that described in Example 7 using EHD jetting in accordance with certain aspects of the present disclosure. In this example, human serum albumin (HSA) and the tumor-targeting, tissue-penetrating peptide, iRGD, are dissolved together in the water and ethylene glycol co-solvent system. Utilizing the same NHS-PEG-NHS crosslinking agent a final solution of protein jetting solution is achieved with a final albumin concentration of 10 w/v %. Similarly, the final NHS-PEG-NHS concentration is 10 w/w % relative to the total albumin concentration. Identical jetting crosslinking conditions are used to generate water-stable, albumin nanoparticles loaded with iRGD.

Example 13 siRNA Loaded Protein Nanoparticles

Fabrication of short interfering RNA (siRNA) loaded protein nanoparticles followed a similar approach to that of the albumin nanoparticles formed in Example 7 using EHD jetting in accordance with certain aspects of the present disclosure. Here, short interfering sequence of double stranded RNA is first complexed in ultra-pure water with a 60 kDa, branched polyethyleneimine (PEI) for a period of thirty minutes. Following this brief incubation period, the PEI-siRNA solution is added to a previously prepared albumin solution in ultra-pure water and ethylene glycol before being mixed with a separately prepared aqueous NETS-PEG-NETS solution. The final albumin and NETS-PEG crosslinker concentrations are identical to that of the albumin nanoparticle jetting solution previously described. Similar jetting and crosslinking conditions are used to generate siRNA-loaded albumin nanoparticles. In this example, the NETS esters of the homo-bifunctional PEG crosslinker react through polycondensation reactions with both lysine residues of albumin and primary and secondary amines present in the PEI. The result of this process are water-stable, protein nanoparticles designed to release siRNA.

Example 14

Paclitaxel-Loaded Albumin Nanoparticles

The fabrication of paclitaxel-loaded albumin nanoparticles is performed in a two-step process. First, paclitaxel (PTX) is complexed with soluble albumin protein using high-pressure homogenization. Briefly, PTX is dissolved in DMSO and mixed with an aqueous solution of human serum albumin (HSA). The resulting solution is loaded into a 10 mL syringe. Using a benchtop high-pressure homogenizer, pressures ranging from 12,000-20,000 PSI are applied, forcing the solution through a small orifice creating a homogenized PTX/HSA solution. This process facilitates the loading of PTX into discrete hydrophobic pockets within the protein.

The homogenization process is repeated until a uniform and opaque solution is obtained. Following this process, the solution is frozen and then lyophilized to yield a dry protein-drug complex. In the second step, following the same process as described previously for the generation of albumin nanoparticles via EHD jetting, a solution is prepared in a water and ethylene glycol cosolvent system. In this example, the protein-drug complex is dissolved in place of the pure albumin with a final albumin-drug concentration of 2.5 wt. %. Identical jetting parameters and crosslinking conditions are used. The result of this combined process are water-stable, PTX-loaded albumin nanoparticles.

Example 15

Disulfide Cross-Linked Albumin Nanoparticles

Albumin protein nanoparticles are prepared using EHD jetting. Human serum albumin (HSA) is dissolved in a (90:10 vol. %) co-solvent system comprising 2,2,2-trifluoroethanol (TFE) and ultra-pure water ($H_2O$) at an albumin concertation of 2.5 w/v %. After mixing for a period of thirty minutes, a 10-fold molar excess of β-mercaptoethanol relative to albumin disulfide bonds is added before further mixing the solution for an additional 30 minutes. The incubation of albumin within this solvent system disrupts the normal disulfide bonds present in the protein, creating free cysteine residues, and allowing for a partial denaturing of the protein to take place. The final protein jetting solution is loaded into a syringe, capped with a 26G stainless steel, blunt-tip needle, and placed into syringe pump to precisely control the flow rate. The positive electrode of a 30 kV power supply is attached to the stainless steel needle while the aluminum collection surface is grounded and maintained at a distance of 15 cm from the needle tip. The solution is pumped at 0.2 mL/h. Upon the formation of a droplet at the tip of the needle, an electric field is applied, distorting the droplet, forming a Taylor cone. The applied voltage required to achieve and maintain a stable cone ranged from 5-7 kV. Rapid acceleration of a viscoelastic jet in the electric field toward the grounded collection surface led to size reduction of the resulting jet by several orders of magnitude facilitating rapid solvent evaporation and solidification of the non-volatile components into spherical nanoparticles. Rapid removal of the solvent allows for the reformation of disulfide bonds to occur, both intra- and intermolecularly. The formation of intermolecular disulfide bonds between adjacent albumin molecules within individual particles results in water-stable, disulfide cross-linked protein nanoparticles. In this example, no additional incubation is required to complete the crosslinking process.

Example 16

Environment-Reactive Protein Nanoparticles

To produce particles that are able to sense and react to particular environments, such as a reducing environment, particles are made to be incorporated with a reducible crosslinking, following a similar synthetic scheme as in Example 7 using EHD jetting in accordance with certain aspects of the present disclosure. Human Serum Transferrin is dissolved into a co-solvent system consisting of ultra-pure water ($H_2O$) and ethanol. 4,7,10,13,16,19,22,25,32,35,38,41,44,47,50,53-Hexadecaoxa-28,29-dithiahexapentacontanedioic acid di-N-succinimidyl ester (Disulfide Crosslinker) Sigma Aldrich, USA) is then separately dissolved into ultra-pure water, and the two solutions combined to bring the solution to a total protein concentration of 10 w/v % and a 10 w/w protein % concentration of Disulfide Crosslinker in relation to total protein content. Identical jetting and crosslinking conditions are then used to result in water-stable nanoparticles. The resulting particles are very similar to those as in Example 7 in regard to morphology and size, but contain a disulfide bond in their crosslinking polymers, which could then be used to release cargos in reducing environments.

Example 17

Fast Crosslinking Protein Nanoparticles

As a variant of the technology, particles can be made to reduce the crosslinking time. A 10% w/v solution of bovine serum albumin (BSA) is dissolved in co-solvent system comprising ultra-pure water ($H_2O$) and ethanol. The solution is then jetted as described above. Within a day of jetting (if not done immediately, the particles are stored at 4° C.), the particles are placed in a sealed container containing 2.5 mL of 20% glutaraldehyde (v/v in $H_2O$), and allowed to vapor phase crosslink for 30 minutes. The aldehyde groups in the vapor phase glutaraldehyde are able to react between neighboring amino groups in the proteins, and resulted in stable intermolecular bonds. To quench any unreacted aldehyde groups, which could produce toxicity in in vivo, the particles are then immediately collected in PBS containing 100 mM glycine and 0.01% tween20. This results in water stable albumin-based protein nanoparticles.

Example 18

Active Therapeutic Enzyme Loaded Protein Nanoparticles

To load particles with active therapeutic enzymes, a similar procedure as in Example 13 is used. A 10% w/v solution of a protein blend, which is made of either a 90:10 or 50:50 w/w ratio of HSA and Catalase, is dissolved in co-solvent system comprising ultra-pure water ($H_2O$) and ethanol. The solution is then jetted, cross-linked and collected as described in Example 13. This results in water stable albumin-based protein nanoparticles loaded with active therapeutic enzymes. The resulting particles are able to process hydrogen peroxide as high levels when compared to unloaded particles, as measured by measuring the reduction of absorbance of hydrogen peroxide at 240 nm using Ultraviolet-visible spectroscopy.

Example 19

Biotechnology-Relevant Enzyme Loaded Protein Nanoparticles

Enzyme loaded particles protein nanoparticles can be fabricated to contain a biotechnology relevant enzyme such as Horseradish Peroxidase, as well. Following a similar synthesis scheme as in Example 14, a 10% w/v solution of a protein blend, in this case a 90:10 w/w ratio of Bovine Serum Albumin and Horseradish Peroxidase, is dissolved in a co-solvent system of ultra-pure water ($H_2O$) and ethanol. Identical jetting and crosslinking conditions are then used to produce particles, and then collected in a PBS solution containing 100 mM glycine and 0.01% tween20, to quench any unreacted aldehyde groups. This results in water stable albumin-based protein nanoparticles loaded with active biotechnology-relevant enzymes. The activity of the enzymes is shown to be significant as compared to unloaded particles by testing them in a standard TMB assay (Thermo Fisher, USA).

Example 20

Protein Nanoparticles with Alkyne-Containing, Trifunctional, PEG-Based Crosslinking Molecule Albumin nanoparticles with an alkyne functional group for post surface modification are prepared via EHD jetting. The jetting solution is composed of human serum albumin (HSA) at 10 w/v % in a co-solvent system consisting of ultra-pure water and ethylene glycol at 80:20 vol. % ratio. The synthesized trifunctional PEG crosslinker is incorporated into the jetting solution at 10 w/w protein % with respect to the albumin protein. To activate the terminal carboxyl groups of the crosslinker, it is first incubated in water with 5 times molar excess of 1-ethyl-3-(3-dimethylaminopropyl)carbodiimide hydrochloride (EDC) followed by addition of sulfo-NHS prior being combined with the albumin protein. Then the final jetting solution of protein and crosslinking agent flows through syringes tipped with 26-gauge needles at 0.1 mL/h using a syringe pump. The distance between the tip of the needle and grounded collection plate is 15 cm. To ensure completion of crosslinking reaction, albumin nanoparticles are kept at 37° C. for 7 days. This results in stable, polymerized alkyne modified albumin.

Example 21

Systemic Brain Tumor Delivery of Synthetic Protein Nanoparticles for Glioblastoma Therapy Glioblastoma (GBM), the most aggressive form of brain cancer, has witnessed very little clinical progress over the last decades, in part, due to the absence of effective drug delivery strategies. Intravenous injection is the least invasive drug delivery route to the brain, but has been severely limited by the blood-brain barrier (BBB). This example describes engineering of a synthetic protein nanoparticle (SPNP) according to certain aspects of the present disclosure based on polymerized human serum albumin (HSA) equipped with the cell-penetrating peptide iRGD. SPNPs containing siRNA against Signal Transducer and Activation of Transcription 3 factor (STAT3i) resulted in in vitro and in vivo downregulation of STAT3, a central hub associated with GBM progression. When combined with the standard of care, concurrent radiotherapy treatment or ionized radiation, STAT3i SPNPs resulted in tumor regression and long-term survival in 87.5% of GBM-bearing mice and prime the immune system to develop anti-GBM immunological memory.

Multiple growth factors and cytokines frequently overexpressed in cancer, such as EGF, FGF, and IL-6, activate STAT3 via tyrosine phosphorylation 8-10. Activated STAT3 (pSTAT3) translocates to the nucleus and participates in the transcription of genes that inhibit apoptosis and promote tumor cell proliferation and metastasis. Histopathological analysis of brain tumors demonstrated STAT3 to be overexpressed in patients with grade III astrocytomas and grade IV GBMs; increased STAT3 levels are negatively associated with MS in these patients. In previous studies, the STAT3 inhibitor CPA-7 induced tumor cell death in GL26 mouse GBM and HF2303 human GBM stem cells. However, a positive therapeutic effect was only observed in peripheral tumors, but not in intracranial tumors, pointing towards the inability of CPA-7, like many small molecule therapeutics and biomolecules, to cross the protective BBB and enter the brain tumor compartment.

Despite efforts in nanoparticle-mediated treatment of GBM, research conducted over the past decades has made only marginal advances with no real promise of a clinical path towards a viable curative treatment. In general, these nanocarriers share a number of common characteristics, e.g., (i) they are made of synthetic materials, (ii) they tend to accumulate and persist in liver and spleen causing severe side effects, and (iii) they are incapable of passing the BBB. In contrast, described herein is an engineered GBM-targeting synthetic protein nanoparticle (SPNP) including of polymerized human serum albumin (HSA) and oligo(ethylene glycol) (OEG), loaded with the cell-penetrating peptide iRGD as well as STAT3i. HSA enjoys rapid and well-understood clearance mechanisms and exquisite biochemical compatibility with both therapeutic agents and homing peptides. In addition, albumin-based nanocarriers can engage cell-surface receptors, such as SPARC34 and gp6035, that are overexpressed on glioma cells and tumor vessel endothelium.

This experiment demonstrates the effective systemic delivery of albumin-based SPNPs to aggressive intracranial GBM tumors. The incorporation of the tumor-targeting, tissue-penetrating peptide, iRGD, resulted in an ability of the SPNPs to penetrate the highly selective BBB and distribute throughout the tumor volume, efficiently delivering siRNA against STAT3 without the use of invasive surgical procedures. When combined with current standard of care, focused radiotherapy, the combined therapy was most effective with 87.5% of mice reaching long-term survival timepoints. When rechallenged with a second tumor in the contralateral hemisphere, these same mice all reach a second long-term survival timepoint in the absence of additional therapeutic intervention. Together, these results suggest that SPNPs are an effective vehicle for the targeted delivery of encapsulated biological therapeutics. Moreover, their use in delivering STAT3i in combination with current standard of care methods provide an immunomodulatory response advantageous in the highly aggressive and recurring GBM disease model.

Synthesis of STAT3 siRNA-loaded, iRGD albumin nanoparticles (NP). Albumin NPs were fabricated via the EHD jetting process previously discussed above. In brief, for all particle types, HSA was dissolved in a cosolvent mixture (80:20 v/v) of ultrapure water and ethylene glycol at a concentration of 7.5 w/v %. A bifunctional OEG (NHS-OEG-NHS, 2 kDa) was added at 10 w/w % relative to HSA. When iRGD was incorporated in the NPs, 355 ng per mg of albumin was added directly to the jetting solution. In contrast, when incorporating siRNA into the particles, the siRNA was first complexed with a branched polyethyleneimine (bPEI, 60 kDa) for 30 min in ultrapure water and the mixture was then added to the jetting solution resulting in 0.04 mg and 355 ng (26 pmol) of bPEI and siRNA per mg of protein NP, respectively. In instances when siRNA was not included (control NPs) an addition of bPEI in ultrapure water was still included. Final jetting solutions were pumped through a syringe equipped with a 26-gauge blunt tip needle at a flowrate of 0.1 mL h$^{-1}$ while a constant voltage (ranging from 7.5 to 9.0 kV) was applied to form a stable Taylor cone at the needle tip. Particles were collected in aluminum pans at a needle to collector distance of 15 cm and then incubated for seven days at 37° C. to facilitate complete polymerization. Albumin NPs were then stored in dark RT conditions in their dry state for future experiments.

Collection and purification of albumin NPs. Albumin NPs were collected according to a standard protocol previously described. In brief, a small volume, 5-10 mL, of water:ethanol (80:20 v/v)+0.5% Tween 20, was added to the aluminum pans containing EHD jetted NPs. The resulting NP suspension was gently sonicated to disperse any aggregates and passed through a 40 µm cell straining filter. The resulting solution was centrifuged at 4000 rpm (3220×g) for 4 min to pellet and remove any albumin aggregates larger than 1 µm in diameter. The supernatant was then divided into 2 mL Eppendorf tubes and centrifuged at 15,000 rpm (21,500×g) to concentrate the samples to a single 1 mL sample for use in planned experiments. Collected NPs were used within 1 week of their collection and were stored at 4° C. during that time.

Characterization of albumin NPs size, shape, and concentration. Albumin NPs were characterized prior to their use in any experiments to ensure they met specifications. Physical characterization included the measurement of particle size in both their dry and hydrated state. To measure particle diameter and investigate their morphology, small silicon wafers were placed on the grounded collection surface and were subjected to the same incubation period to complete the step-growth polymerization. These samples were imaged via scanning electron microscopy (SEM) using a FEI NOVA 200 SEM/FIB instrument. Obtained SEM images were characterized using ImageJ software. NPs in their hydrated state were collected and purified as described above. The stock solution was diluted in PBS+0.5% Tween 20 for subsequent measurements using DLS and NTA (nanoparticle tracking analyzer) to investigate size and solution concentration. DLS and NTA analysis was performed using the Malvern Nano ZSP and NanoSight NS300 instruments and software respectively. Albumin NP solution concentration was further validated using the BCA (bicinchoninic acid) assay.

Albumin NP stability and swelling characterization. Albumin NPs collected and purified as described above were studied to determine their swelling behavior in response to changes in pH and stability in their hydrated state. NPs from the concentrated stock solution were diluted into either a solution of PBS+0.5% Tween 20 (pH 7.4) or sodium acetate—acetic acid buffer+0.5% Tween 20 (pH 5.0). The final NP solutions were stored at 37° C. for a period of 10 days. Particle diameter was measured throughout this period to compare the particle size distribution in response to acidic vs. neutral pH conditions and their overall stability at physiological temperatures.

Loading and release of siRNA from albumin NPs. To validate siRNA loading and characterize its release from the albumin NPs, a fluorescently labeled, Silencer™ Cy3-labeled negative control siRNA was incorporated into the NP formulation following the same process as described above. NPs were incubated and collected as described above. To validate siRNA incorporation into the particles, an Alexa Fluor™ 488 BSA conjugate was added at 0.5% of the total albumin mass. Colocalization of the fluorescent albumin NP and siRNA were confirmed using super-resolution STED (stimulated emission depletion) microscopy. Imaging was performed with a Leica 1×STED instrument and processed using the Leica LAS X software. The release of the same fluorescent siRNA was conducted over a period of four days in PBS+0.5% Tween 20 at 37° C. The supernatant was analyzed using a Horiba fluorimeter and compared against a previously generated calibration curve.

Cell line and cell culture conditions. GL26, GL26-Cit, and GL26-OVA GBM cells were cultured in Dulbecco's modified eagle (DMEM) media supplemented with 10% fetal bovine serum (FBS), 100 units mL-1 penicillin, and 0.3 mg mL-1 L-glutamine. For mCitrine and OVA selection, the culturing medium was additionally supplemented with 6 µgmL-1 G418. Cells were passaged every 2-3 days and were maintained in a humidified incubator at 95% air/5% CO2 at 37° C.

Immunofluorescence uptake/lysosome colocalization. To study the effect iRGD has on particle fate upon uptake by glioma cells, GL26 cells were cultured as described above in 4-well Nunc™ Lab-Tek™ Chamber Slides. Cells were seeded at 50,000 cells per well and allowed to adhere overnight. Twelve hours after initial seeding, media was exchanged. Fresh media contained either iRGD albumin NPs or albumin NPs (without iRGD), each labeled by incorporating an Alexa Fluor™ 647 BSA, at a concentration of 13.3 µg NPs per mL. Thirty minutes after particle administration, the media was removed, cells were washed three times with warm PBS, and fresh NP-free media was then added to each well. Cells were cultured normally for an additional three hours before the cells were washed, fixed, and stained. In brief, cells were washed with PBS and fixed in 2% paraformaldehyde in PBS for 15 min and then permeabilized with 0.1% Triton X-100 in PBS for an additional 15 min. Cells were then rinsed three times with PBS, and five times with PBS+0.5% BSA (PBB) and blocked with a one-hour incubation in 2% BSA in PBS. Following a rinse with fresh PBB, cells were incubated with primary antibody for LAMP-1, a lysosomal marker, at 5 µgmL-1 in a PBB solution at room temperature for one hour. After five rinses with fresh PBB, a mixture of Goat Anti-Rabbit IgG H&L Alexa Fluor™ 555 and Phalloidin Alexa Fluor™ 488, prepared in PBB was added and incubated for one hour at room temperature. Each well was rinsed five times with PBB, incubated for one minute with Hoescht at 0.01 mg mL-1 in DI water, and washed three times with fresh PBS. Finally, the chamber portion of the device was removed, the glass slide allowed to dry and samples were mounted using Prolong™ Diamond Antifade Mountant to preserve the samples and protect against fluorescent signal bleaching. Once stained and mounted, each sample was imaged using the University of Michigan MTh Nikon A1SI confocal microscope and processed using NIS-Elements AR software. Settings for all samples were optimized and kept consistent from sample to sample. Z-stack images were collected from multiple regions within each well and the resulting three-dimensional images were analyzed using an established protocol and the CellProfiler software. Analyzed data were used to calculate the relative number of NPs internalized by the cells and the percent of these cells colocalized within the lysosomes.

In vitro albumin SPNP delivered siRNA GFP silencing. As a preliminary experiment, to validate the ability of siRNA delivered via the albumin NPs, particles loaded with siRNA against GFP were synthesized as described above. GL26-cit cells were cultured consistent with previously conducted experiments. Twelve hours after initial seeding at 50,000 cells/well in 4-well Nunc™ Lab-Tek™ Chamber Slides, NPs were administered at a concentration of $1.0 \times 10^{11}$ NP per mL. Cells were incubated with particles for a period of two hours before they were washed three times with PBS and fresh media was added to each well. Cells were then cultured for an additional five days. On each day, one sample from each experimental group was washed, fixed, and stained according to an established protocol. In brief, cells were washed three times with warm PBS and fixed in 3.7% paraformaldehyde solution in PBS for 15 min. Finally, cells were washed three times with fresh PBS, dried, and samples were mounted using Prolong™ Diamond with DAPI Antifade Mountant to both stain the nucleus and preserve the samples. Samples from each experimental group and time point were imaged using the University of Michigan MIL Nikon A1SI confocal microscope and processed with the NIS-Elements AR software. Multiple Z-stacks from each sample were taken, maintaining constant laser settings across all samples. GFP signal, normalized to that of the nucleus, was quantified using ImageJ software.

In vitro STAT3 silencing via albumin SPNP delivered siRNA. To validate the ability of STAT3 siRNA delivered via SPNPs, particles loaded with siRNA against STAT3 were synthesized as described above. Twelve hours after initial seeding of GL26 glioma cells at 300,000 cells/well in 6-well cell culture plates, NPs were administered at a concentration of $1.0 \times 10^{11}$ NP per mL. Cells were incubated with particles for a period of two hours before they were washed three times with PBS and fresh media was added to each well. Cells were then cultured for an additional three days with a daily exchange of fresh media. Whole-cell extracts were prepared by lysing the cells with RIPA buffer for 5 min on ice, then centrifuged at 10,000×g for 5 minutes at 4° C. to remove cellular debris. Protein concentration was quantified using the Pierce BCA Protein Assay Kit. STAT3 expression was quantified using the ProteinSimple capillary electrophoresis-based western blot assay and normalized to the expression of GAPDH. Relative protein expression was measured and analyzed using the Compass for SW software.

Intracranial GBM models. Six to eight-week-old female C57BL/6 were purchased from Jackson Laboratory (Bar Harbor, ME) and were housed in pathogen-free conditions. Immune-competent mice were housed in a pathogen-free, humidity (40%-60%) and temperature (65-75° F.) controlled vivarium on a 12:12 h light:dark cycle (lights on 0700) with free access to food and water. Intracranial surgeries were performed in 6-8 week old C57BL/6 mice weighing 17-24 g. Orthotopic tumors were established in C57BL/6 mice by stereo-tactically injecting 20,000 GL26, GL26-Cit or 60,000 GL26-OVA cells into the right striatum of the brain using a 22-gauge Hamilton syringe (1 µL over 1 min) with the following coordinates: +1.00 mm anterior, 2.5 mm lateral, and 3.00 mm deep.

Intratumoral diffusion of iRGD-functionalized albumin SPNPs. To assess Albumin NP accumulation within the GBM TME, Alexa Fluor™ 647 dye was loaded into albumin NP, which were administered intratumorally into GBM bearing mice. Fourteen days post GL26-mtomato tumor implantation, mice (n=2/group) were intratumorally injected with $3.6 \times 10^8$ or $3.6 \times 10^9$ Alexa Fluor™ 647 loaded Albumin NP in 3 µL volume. From each group, mice were transcardially perfused 4 or 24 h after NP administration, and brains were processed for imaging. Alexa Fluor™ 647 dye loaded Albumin NP accumulation within the TME was imaged with confocal microscopy (Carl Zeiss: MIC System) at ×5 and ×20 magnification.

Intravenous iRGD NP delivery. To assess the accumulation of systemically administered iRGD-Albumin NPs within the GBM TME, Alexa Fluor™ 647 dye was loaded into the NPs, which were injected i.v. into GBM bearing mice. Seven days post GL26-cit tumor implantation, mice were i.v. injected with $2.0 \times 10^{11}$ NPs in mice) and 24 h (n=3 mice), and brains were processed for imaging. Accumulation of NPs within the TME was imaged with confocal microscopy (Carl Zeiss: MIC System) at ×63 with an oil-immersion lens.

Biodistribution of iRGD NPs post systemic delivery. To evaluate the biodistribution of iRGD-albumin NP in vivo, NPs were loaded with Alexa Fluor™ 647 dye. C57BL/6 mice bearing GL26 tumors (n=4) were injected intravenously (i.v) with $2.0 \times 10^{11}$ Alexa Fluor™ 647 iRGD-albumin or albumin alone NPs in 100-µL volume 7, 10, and 13 days post tumor implantation. For the control group, tumor naïve mice were injected i.v. with $2.0 \times 10^{11}$ Alexa Fluor™ 647 iRGD-albumin or albumin alone NPs in 100-µL volume. From each group, mice were transcardially perfused 24 h post the last injection of NPs, and vital organs (i.e., lungs, spleen, liver, brain, and kidneys) were harvested. The fluorescent signal within each organ was measured with IVIS spectrum analysis.

To assess the iRGD-Albumin NPs' accumulation within the GBM TME, NPs loaded with Alexa Fluor™ 647 dye were administered i.v into GBM bearing mice. Seven days post GL26-cit tumor implantation, $2.0 \times 10^{11}$ NPs in 100-µL volume were administered i.v. to mice (n=4). Then, mice were transcardially perfused at either at 4 h (n=2) or 24 h (n=2) post the NP injection. Brains were collected and processed for imaging. Accumulation of NPs within the TME was imaged with confocal microscopy (Carl Zeiss: MIC System) at 63× with an oil-immersion lens.

STAT3 expression following systemic administration of STAT3. To validate the ability of STAT3 siRNA loaded SPNPs to reach the tumor in vivo, particles loaded with siRNA against STAT3 were synthesized as described above. C57BL/6 mice bearing GL26 tumors (n=5) were injected intravenously (i.v) with 2.0×1011 Alexa Fluor™ SPNPs, STAT3i SPNPs, or free STAT3i in 100 μL volume on 5, 7, 11, 15, 18, and 22 days post tumor implantation. For the control group, tumor-bearing mice were injected i.v with an equal volume of saline. Mice from each group were transcardially perfused with Tyrode's solution 24 h post the last injection of NPs or saline and brains were extracted. Tumors were dissected from the brain, and single-cell suspension was obtained. Whole-cell lysates were prepared by incubating the dissociated cells pellet with protease inhibitors and 1.4 mL RIPA lysis buffer on ice for 5 min. Resulting cell lysates were centrifuged at 13,000 rpm (25,000×g) at 4° C. for 10 min and supernatants were collected to determine protein concertation in comparison to standard bovine serum albumin (BSA) protein concentrations through bicinchonicinc acid (BCA) assay. STAT3 and downstream target's protein expression was quantified using the Protein-Simple capillary electrophoresis-based western blot assay and normalized to total protein expression.

Therapeutic study in tumor-bearing animals. To evaluate the therapeutic efficacy of iRGD-Albumin NPs loaded with STAT3i, saline, 2.0×1011 of empty SPNPs, STAT3i SPNPs or 330 μg of free STAT3i were administered intravenously in 100 μL volume into GL26 tumor-bearing mice on 5, 8, 11, 15, 18, 22, and 25 days post tumor implantation. Also, a dose of 2 Gy Irradiation (IR) was administered to tumor-bearing mice 5 days a week for two weeks at 7 days post tumor implantation. Each treatment group consisted of at least n=5 mice. When mice displayed signs of neurological deficits, they were transcardially perfused with tyrodes solution and 4% paraformaldehyde (PFA).

Blood cell counts and serum biochemistry. Blood from GL26 GBM bearing mice was taken from the submandibular vein and transferred to EDTA coated microtainer tubes (BD Biosciences) or serum separation tubes (Biotang). Samples in the serum separation tubes were left at room temperature for 20 min to allow for blood coagulation before centrifugation at 2000 rpm (400×g). Complete blood cell counts and serum chemistry for each sample were determined.

Liver histopathology. Liver tissues from treated animals were collected following the completion of the full STAT3i SPNP+IR therapeutic regimen described in FIG. 27A. PFA-fixed tissues were embedded, sectioned at 4 μm, and stained with H&E.

Immunohistochemistry. Using the vibratome system, PFA-fixed brains were serially sectioned 50-μm thick and placed in PBS with 0.01% sodium azide. IHC for macrophages was performed by permeabilizing the brain sections with TBS-0.5% Triton-X (TBS-Tx) for 5 min, followed by antigen retrieval at 96° C. with 10 mM sodium citrate (pH 6) for 20 min. Then, the sections were allowed to cool to room temperature (RT) and washed five times with TBS-Tx (5 min per wash). Next, the brain sections were blocked with 10% goat serum in TBS-Tx for 1 h at RT followed by overnight primary antibody F4/80 (BioRad, MCA497GA, 1:250) incubation at RT. The primary antibody was diluted in 1% goat serum in TB S-Tx. The next day, brain sections were washed with TB S-Tx 5 times and incubated in fluorescent-dye conjugated secondary antibody (Thermofisher, A21209, 1:1000) diluted in 1% goat serum TBS-Tx in the dark for 6 h. Finally, brain sections were washed in PBS 3 times and mounted onto microspore slides and coverslipped with ProLong Gold. High magnification images at ×63 were obtained using confocal microscopy (Carl Zeiss: MIC-System). H&E staining on whole-brain sections was performed according to standard H&E staining protocols.

Similarly, H&E staining was performed on livers that were embedded in paraffin and sectioned 5 μm thick using the microtome system. Brightfield images of the stains were obtained using Olympus BX53 microscope.

ELISA. To evaluate whether human albumin within the NPs is immunogenic, expression of antibodies against human albumin or mouse albumin in the serum of mice treated with saline, free NPs, free STAT3i,STAT3i SPNPs, IR, or STAT3i SPNPs+IR was determined using ELISA. In brief, 96-wells' plates were coated with NPs loaded with either mouse albumin or human albumin overnight at 4° C. The coated plates were washed the next day with 1×PBS+ 0.05% Tween 20 (PBS-Tween) five times, and then blocked with PBS-Tween containing 5% goat serum at RT for 2 h. This was followed by five more washes with PBS-Tween. Next, mouse serum diluted 1:100 from each treatment group was added to the NP coated wells in a 100 μL volume and incubated at 4° C. for 24 h. For a positive control, primary antibody against HSA (abcam, ab10241, 1:1000) or mouse serum albumin (abcam, ab34807, 1:1000) was added to the appropriate wells. The next day, the plates were washed five times with PBS-Tween and 100 μL of anti-mouse (Thermofisher, 62-6520, 1:3000) or anti-rabbit (abcam, ab6721, 1:3000) secondary antibody was added to the appropriate plate, followed by 1 h incubation at 37° C. For a negative control, secondary anti-body against HSA or mouse serum albumin was added to the appropriate wells. Plates were then washed five times with PBS-Tween. Substrate solution (TMB) was added and the plate was incubated in the dark at RT for 30 min and the reaction was quenched by the addition of 2 M Sulfuric Acid. Plates were read on a 96-well plate reader (Spec-tramax Plus, Molecular Devices) at O.D. 450 nm.

To assess the immune cell population within the GL26-OVA TME, two days post STAT3i alone, empty SPNP, STAT3i SPNP or STAT3i SPNP+IR treatment detailed above, mice were euthanized and the tumor mass with the brain was dissected and homogenized using Tenbroeck (Corning) homogenizer in DMEM media containing 10% FBS. Tumor-infiltrating immune cells were enriched with 30-70% Percoll (GE Lifesciences) density gradient and the cells were resuspended in PBS containing 2% FBS (flow buffer). Live/dead staining was carried out using fixable viability dye (eBioscience). Non-specific antibody binding was blocked with CD16/CD32. Dendritic cells were labeled with CD45, CD11c, and B220 antibodies. Plasmacytoid dendritic cells (pDCs) were identified as CD45+/CD11c+/B220+ and conventional dendritic (cDCs) cells were identified as CD45+/CD11c+/B220−. Macrophages were labeled with CD45, F4/80, and CD206 antibodies. M1 macrophages were identified as CD45+/F4/80+/CD206low and M2 macrophages were identified as CD45+/F4/80+/CD206high. Tumor-specific T cells were labeled with CD45, CD3, CD8, and SIINFEKL-H2Kb-tetramer. Granzyme B and IFNγ were stained using BD intracellular staining kit following the manufacturer's instructions. For T cell functional analysis, purified immune cells from the TME were stimulated with 100 μg mL-1 of GL26-OVA lysate for 16 h in DMEM media containing 10% FBS followed by 6-h incubation with Brefeldin and monensin. For integrin αvβ3 and αvβ5 analysis, untreated GL26-tumor-bearing mice were euthanized 23 DPI and both the tumor-bearing hemisphere and the contralateral hemisphere were dissected. Cells were dissociated from both the hemispheres into single-cell suspension and CD45 cells were labeled with magnetic beads (Miltenyi) using the manufactures' instructions at 4° C. Purified cells were washed and passed through a preconditioned MS column placed in the magnetic field of a MACS separator. Cells that were negative for CD45 were collected, resuspended in flow buffer and labeled with $\alpha v\beta 3$ (Novus, NBP2-67557) and $\alpha v\beta 5$ (BD Bioscience, 565836) for flow cytometry analysis. All stains were carried out for 30 min at 4° C. with 3× flow buffer washes between live/dead staining, blocking, surface staining, cell fixation, intracellular staining and data measurement. All flow measurements have been made utilizing with FACSAria flow cytometer (BD Bioscience) and analyzed using Flow Jo version 10 (Treestar).

Particle design, synthesis, and characterization. SPNPs were prepared via electrohydrodynamic (EHD) jetting, a process that utilizes atomization of dilute solutions of polymers to produce well-defined NPs (FIG. 10A and FIG. 11). Rapid acceleration of a viscoelastic jet in an electric field leads to a size reduction by several orders of magnitude facilitating rapid solvent evaporation and solidification of the non-volatile components into NPs. Here, the jetting solution included HSA and a bifunctional OEG macromer (NHS-OEG-NHS, 2 kDa), which were mixed with therapeutic siRNA, polyethyleneimine (PEI, a siRNA complexing agent), and the tumor penetrating peptide, iRGD, prior to NP preparation. Similar to a step-growth polymerization, the OEG macromer was combined with albumin molecules through reaction with its lysine residues resulting in water-stable SPNPs. After EHD jetting and collection, the resulting SPNPs had an average diameter of 115±23 nm in their dry state (FIG. 10B). Once fully hydrated, it was observed that the average diameter of SPNPs increased to 220±26 nm based on dynamic light scattering (DLS) measurements (FIG. 12). The degree of NP swelling was controlled by varying the HSA-to-OEG ratios between 4:1 and 20:1 and the molecular weight of the OEG macromer between 1 and 20 kDa. An increase of the OEG content from 5 to 20% resulted in a reduction of SPNP swelling by 20%. The resulting SPNPs were stable for at least 10 days at 37° C. under physiological conditions; with no significant change in particle size or morphology (FIG. 13). When exposed to mildly acidic conditions (pH 5.0), similar to those observed in endosomes of cancer cells, the diameters of SPNPs increased to 396±31 nm (FIG. 10C). It is noted that defining particle properties, such as particle size, shape, and swelling behavior, was, within the margins of error, identical for fully loaded SPNPs, empty NPs and NPs loaded with siRNA and/or iRGD.

In vitro cell uptake and siRNA activity. Previously, co-delivery of the cell-penetrating peptide iRGD has increased tumor targeting for both, small drugs and iron oxide NPs42. The iRGD peptide has been shown to act in a three-stage process, first binding to $\alpha v\beta 3$ and $\alpha v\beta 5$ integrins, followed by a proteolytic cleavage step and a secondary binding event to neurophilin-1 (NRP-1), which activates an endocytotic/exocytotic transport pathway. In the past, iRGD mediated tumor homing has been approached either in form of systemic co-delivery of iRGD with NPs or by decorating the NPs with surface-bound iRGD. In this case, the iRGD peptide is preloaded into SPNPs during EHD jetting to promote local release at the vicinity of the BBB. To investigate the intracellular fate of NPs and the effect of iRGD as a targeting ligand, in vitro uptake experiments were performed. When iRGD-loaded SPNPs were incubated with GL26 glioma cells for a period of 30 min, particle uptake increased by ~5-fold compared to NPs without iRGD (FIG. 10E). Image analysis of 3D confocal images (FIG. 10D) using CellProfiler revealed that significantly less particles colocalized with lysosomes of GL26 glioma cells compared to NPs without iRGD (FIG. 10F). These data suggest that loading iRGD into SPNPs results in higher uptake and higher cytosolic SPNP concentrations in glioma cells. The pH-dependent swelling of SPNPs, along with the "proton sponge" effect previously postulated for PEI48, may contribute to more effective particle escape from endocytotic vesicles, enhancing overall siRNA delivery to the cytosol and RNA-induced silencing.

Whether siRNA loaded into SPNPs during EHD jetting remains biologically active was evaluated. First, siRNA loading and release from SPNPs was evaluated using a Cy3-labeled STAT3i surrogate. Utilizing stimulated emission depletion (STED) microscopy, uniform distribution of siRNA was confirmed throughout the entire NP volume (FIG. 14). In vitro release of fluorescently tagged siRNA confirmed that 96% of the initial amount of siRNA was encapsulated into SPNPs; corresponding to a siRNA loading of 340 ng, or 25 pmol of siRNA per mg of SPNPs. Furthermore, ~60% of the encapsulated siRNA was released over the first 96 hours, followed by a sustained release period progressing for 21 days (FIG. 15). When albumin NPs were loaded with siRNA against GFP, SPNPs significantly suppressed GFP expression in mouse glioma cells transfected to express mCitrine (GL26-Cit, FIG. 16) relative to control albumin NPs loaded with scrambled siRNA or free GFP siRNA that was delivered using lipofectamine as the transfection agent. Moreover, protein knockdown persisted significantly longer in the SPNP group than in lipofectamine-transfected cells (FIG. 16). While the latter entered a recovery phase after two days and nearly returned to normal GFP levels by day five, cells treated with GFPi SPNPs showed sustained protein knockdown throughout the experiment. There were no significant differences in particle size, surface charge, or morphology between siRNA-loaded SPNPs and the control particles (FIG. 17).

For SPNPs co-loaded with iRGD and STAT3i at concentrations of 2.5 and 25 µg/mL, a significant reduction in total STAT3 protein expression was observed relative to the untreated control group or empty SPNPs (FIG. 10G). Moreover, a dose-dependent response was observed, i.e., a higher SPNP concentration resulted in ~2-fold further decrease in total STAT3 expression. No detectable signs of cytotoxicity were observed for any of the tested NP groups, which is attributed to the fact that the delivered siRNA concentrations were below the cytotoxicity limit observed for free STAT3 siRNA in GL26 cells (FIG. 18). Based on these in vitro experiments, an effective dose of 5 µg/kg was selected for subsequent animal studies.

In order to simultaneously evaluate particle stability and diffusion within the tumor microenvironment (TME), Alexa Fluor 647 SPNPs were administered intratumorally (FIG. 19). iRGD enhances the penetration of co-delivered therapeutics throughout the tumor volume. This becomes increasingly relevant in GBM where recurrence occurs locally in regions adjacent to the tumor resection cavity. Following intratumoral injection of SPNPs, NPs were widely distributed throughout the tumor volume extending from the injection site. Furthermore, persistent fluorescent signal associated with SPNPs was observed within the tumor hours after intratumoral administration.

Systemic delivery of SPNPs in an intracranial GBM model. In the past, the BBB has been an unsurmountable delivery challenge for nanocarriers that are systemically administered via IV injection. To evaluate whether systemically delivered SPNPs can home to brain tumors, SPNPs loaded with Alexa Fluor 647-labeled albumin were prepared as described above. In the absence of large animal GBM models, the very aggressive GL26 syngeneic mouse glioma model, which is known to exhibit histopathological characteristics encountered in human GBM54, was selected to evaluate GBM-targeting of SPNPs. In addition, this model features an uncompromised immune system, which was deemed to be important, because of the prominent role that STAT3 plays in downregulation of the immune system. A dose of $2.0 \times 10^{13}$ SPNPs was delivered to GBM-bearing mice via a single tail vein injection seven days after glioma cell implantation (GL26-Citrine, approximate tumor size: 10 mm$^3$, FIG. 20) in the right striatum of the mice (FIG. 21A). After 4 or 24 hours, animals were perfused, and brains were collected, sectioned, and stained with F4/80 (a marker for macrophages), prior to confocal imaging. SPNPs were taken up by other organs, such as liver, kidney, spleen, and the lungs (FIG. 21D). A significant number of SPNPs appeared to have crossed the BBB and were identified within the brain TME at both time points (FIG. 21B). Tumor targeting was markedly increased after 24 hours.

Using the same intracranial tumor model, GBM specific biodistribution of SPNPs was assessed. Tumor-bearing mice were injected three times (7, 10, and 13 days post implantation, DPI) with Alexa Fluor 647-labeled SPNPs or NPs without iRGD (FIG. 21C). In addition, normal mice (non-tumor bearing) were subjected to the same regimen to delineate tumor-specific characteristics. After 14 days, normal, non-tumor bearing mice and tumor-bearing mice were euthanized, their main organs were collected, and the NP distribution was analyzed via fluorescence imaging (FIG. 21D). In both GBM-bearing and non-tumor bearing mice, significantly more SPNPs were observed in the brain compared to iRGD-free NPs. As expected, SPNPs also accumulated in the lungs and liver—independent of the particular experimental group. The former can be attributed to being the first capillary bed the NPs would encounter following intravenous injection, while the latter represents the primary route of clearance for NPs measuring 10-250 nm in diameter. Brain accumulation of SPNPs loaded with iRGD was higher for both naïve and GBM-bearing mice compared to iRGD-free NP groups. When directly comparing SPNP localization within the brain compartment, the accumulation of iRGD-loaded SPNPs was 40% higher in tumor-bearing brains (FIG. 21E) than in non-tumor bearing mice.

Next, whether the increased accumulation of SPNPs in the brain of tumor-bearing mice is mediated by integrin expression on tumor cells was assessed. Specifically, the relative expression of αvβ3 and αvβ5 integrins was observed, because these ligands can play pivotal roles in the iRGD-induced accumulation of NPs and small drugs in tumors, and are overexpressed in gliomas. Using the GBM model and dosing schedule from the biodistribution studies, brains from GBM tumor-bearing mice were collected at 23 DPI. Normal brain and tumor tissue were dissected from the brain, processed, and stained with αvβ3 and αvβ5 antibodies for flow cytometry analysis. More than 60% of the GBM tumor population expressed αvβ3 and αvβ5 integrins at high levels, while normal brain cells showed minimal expression of these proteins. These results, along with the observed differences in brain accumulation in the biodistribution study, appear to be consistent with the previously postulated hypothesis that iRGD promotes the accumulation of SPNPs in the brain.

In vivo survival studies. The Signal and Transducer of Activation 3 (STAT3) transcription factor is a hub for multiple signaling pathways, which mediate tumor progression and immune functions. There are no effective delivery strategies of anti-STAT3 therapeutics to the brain. Systemic delivery of a single dose of STAT3i SPNPs to GMB bearing mice significantly increased their MS (FIG. 22). To further test the efficacy of SPNPs in vivo, GBM-bearing mice were treated intravenously with multiple doses of STAT3i SPNPs over the course of a three-week treatment regimen (FIG. 23). After tumor implantation, the MS of untreated mice was about 28 days. In mice that received multiple doses of empty SPNPs, the MS remained unaltered (28 days). In contrast, when SPNPs loaded with STAT3i were administered, the MS increased to 41 days, a statistically significant increase of 45%. Delivery of the same doses of free STAT3i resulted in a modest extension of MS by 5 days, which is likely too low to elicit a significant therapeutic effect. The low efficacy of free STAT3i can be explained by the rapid degradation of genetic material following systemic administration—in addition to siRNA's inability to cross the BBB.

Encouraged by the prospect of a NP formulation for STAT3i delivery with significant in vivo efficacy, STAT3i SPNPs is combined with concurrent treatment with the current standard of care, i.e., focused radio-therapy (IR). A treatment protocol was established that combined the previously evaluated multi-dose regimen with a repetitive, two-week focused radiotherapy regimen (FIG. 24A). Once GBM tumors had formed, mice received seven doses of STAT3i SPNPs over the course of a three-week period. During each of the first two weeks of therapy, mice also received five daily 2 Gy doses of IR for a total of ten treatments (FIG. 24A). Experimental groups included mice that received either STAT3i SPNPs, empty SPNPs, free STAT3i, or saline with or without combined radiotherapy. In all cases, the addition of radiotherapy increased the MS, with IR alone resulting in a MS extension from 28 to 44 DPI (FIG. 24B). Combining IR with empty SPNPs did not further alter the MS. Consistent with the previous experiment, free siRNA provided a slight, statistically significant benefit, where the MS was increased to 58 DPI, when combined with IR (FIG. 24B, brown line). However, the most significant effect was observed for the combination of STAT3i SPNPs with IR. Of the eight mice in this group, seven reached the standard long-term survivor time point of 90 DPI and appeared to be completely tumor-free thereafter (FIG. 24B, blue line). The single mouse receiving this treatment that did not reach long-term survival was moribund at 67 DPI, living longer than any other non-surviving subject from all other groups.

In order to characterize the effects of the combined treatments, additional studies were performed. Following the same treatment outlined in FIG. 24A, the expression of STAT3 and its active phosphorylated form, pSTAT3, is elucidated in the brain tissues (FIG. 24C). The greatest reduction in both the total and phosphorylated form of the protein was found in the STAT3i SPNP group. Greater than 50% reduction in total STAT3 protein was present in GBM bearing mice treated with STAT3i SPNP, compared to the saline-treated control. Greater than 10-fold reduction in pSTAT3 levels were observed in GBM bearing mice treated with STAT3i SPNP, compared to the saline-treated control. In contrast, the total STAT3 levels were relatively unchanged in both, the free STAT3i and empty SPNP groups, compared to saline control. Here, pSTAT3 was increased by 110% in the cohort receiving empty SPNPs, suggesting a shift in the balance of the two protein forms.

Immunohistochemistry (IHC) analysis was used to compare the brains of long-term survivors to other treatment groups. FIG. 24D shows a direct comparison of the brain of a long-term survivor and that of a control animal that did not receive treatment. Hematoxylin and Eosin (H&E) staining clearly shows the presence of a fully developed tumor localized within a single hemisphere of the saline-treated mice. Conversely, mice treated with STAT3i SPNP+IR showed no evidence of intracranial tumor (FIG. 24D, top). Moreover, no apparent regions of necrosis, palisades or hemorrhages were present in these animals 90 DPI after receiving a full course of therapy. Myelin basic protein (MBP) staining was performed to assess the integrity of myelin sheaths, an indicator for the disruption of surrounding brain architecture. No apparent changes in myelin sheath morphology were observed in mice that received the combined STAT3i SPNP+IR treatment when compared to the cancer-free right faces of mice in the saline-treated control group (FIG. 24D, middle). In addition, CD8 T cells were sparse in the TME (FIG. 24D, bottom) and their total number was significantly reduced in STAT3i SPNP+IR treated mice compared to the saline-treated control group (FIG. 25)—indicating a lack of inflammation response due to the treatment.

To further investigate the potential role of the adaptive immune system, the population of CD8 T cells within the TME is more closely examined via flow cytometry. Tumors were established in mice using GBM cells that harbored a surrogate tumor antigen ovalbumin (OVA) and compared the responses elicited by the various treatment formulations (FIG. 24E). The OVA-based GBM model was utilized to assess the frequency of tumor antigen-specific T cells within the GBM microenvironment, due to the αvailability of OVA-specific MHC tetramers. Tumor-specific T cells were characterized by staining for the SIINFEKL-H2Kb-OVA tetramer, an OVA cognate antigen within the CD8 T cell population. Tumor-specific CD8 T cells (CD3+/CD8+/SIINFEKL-H2Kb tetramer) within the STAT3i SPNP+IR group were increased by two-fold compared to all other groups (FIG. 24F, top). Staining the same population of cells with interferon-γ (IFN-γ) and granzyme B (GZB) revealed a two-fold increase in cytotoxic T cells in the TME (FIG. 24F, middle and bottom) in the STAT3i SPNP+IR group relative to all other groups. Flow cytometry gating strategies used within this study are presented in FIG. 26. Taken together with the increased MS of GL26 GBM mice in the survival study, these results suggest a robust anti-GBM response elicited by the combined STAT3i SPNP+IR therapy can contribute to therapeutic success.

Recognizing that significant SPNPs accumulated in the liver (FIG. 21D), complete blood cell counts, serum biochemistry, and liver histopathological analysis were performed to examine potential off-target side effects of the combined therapeutic strategy. Systemic toxicity of STAT3i SPNPs+IR treatment was evaluated following the treatment schedule indicated in FIG. 27A. No significant differences in the cellular components of the blood were noted in complete blood cell counts analysis for animals receiving SPNP, STAT3i, STAT3i SPNP, or STAT3i SPNP+IR treatment compared with animals in the saline treatment group (FIG. 27B-I). Moreover, there was no significant difference in important biomarkers involved in the kidney (creatinine, blood urea nitrogen) and liver (aminotransferase, aspartate amino-transferase) physiology for animals receiving SPNP, STAT3i, STAT3i SPNP, or STAT3i SPNP+IR treatment compared with animals in the saline treatment group (FIG. 28), indicating that no overt adverse side-effects occurred in these tissues.

In addition, independently conducted pathological analysis of potential side effects affecting the livers of mice treated with STAT3i SPNP+IR therapy revealed minimal to mild monoculear pericholangitis across all groups and it was characterized as spontaneous background rather than a direct result of the applied therapy. (FIG. 27J). In all treatment groups, with the exception of the saline-treated control, minimal to mild coagulative necrosis was present. In the treatment group that received free STAT3i, one animal displayed multiple foci of coagulative necrosis, which distinguished it from all other animals in the entire study cohort, including those from the combined STAT3i SPNP+IR group, where the regions of necrosis were generally small and were deemed not to induce biologically significant adverse effects on liver function.

Next, SPNP-induced immune responses were assessed using a modified enzyme-linked immunosorbent assay (ELISA, FIG. 29). To αvoid a species-to-species mismatch due to the use of HSA in mice, otherwise identical NPs were synthesized, in which HSA was replaced with mouse serum albumin (MSA). No circulating antibodies specific to MSA SPNPs were observed in any of the treatment groups indicating neglectable immunogenicity against any of the individual components of SPNPs, such as OEG, STAT3i, iRGD, or PEI (FIG. 27K). As expected, replacing MSA with HSA resulted in elevated levels of HSA antibodies for both, STAT3i SPNP and empty SPNP treatment groups (FIG. 27L). Free STAT3i therapy did not induce this same response suggesting that antibodies were formed in response to the exposure of the NPs rather than the active therapeutic ingredient.

Taken together, these results indicate that sequential intravenous administration of STAT3i SPNP in combination with radiation does not cause systemic toxicity. In this study, there were no inflammatory reactions caused by STAT3i SPNP+IR therapy (FIGS. 27 and 28), indicating that the present treatment strategy does not cause short-term toxicity. Flow cytometry analysis of tumor-infiltrating macrophages and conventional dendritic cells (cDCs:CD45+/CD11c+/B220−) was used to compare treatment groups containing free STAT3i, empty SPNP, and STAT3i SPNPs in combination with IR (FIGS. 30A and 30B). Co-staining of CD45+ cells with F4/80 and CD206 antibodies was used to establish a subpopulation of tumor-associated macrophages (TAMs). Within the TAM population, both, M1 (CD45+/F4/80+/CD206−) and M2 (CD45+/F4/80+/CD206+) macrophage phenotypes, were identified for all cohorts, but their relative abundance was significantly different in the STAT3i SPNP+IR group compared to all other groups. In the STAT3i SPNP+IR group, M1 macrophages were increased by 2.5-fold (FIG. 30C, left), whereas the number of M2 macrophages was decreased by three- to four-fold (FIG. 30C, middle). These findings are consistent with the notion that the STAT3i SPNP+IR treatment selectively decreases the immune suppressive M2 macrophage subpopulation. In addition, antigen presentation by cDCs was significantly higher in animals receiving STAT3i SPNPs compared to free siRNA and empty SPNPs (FIG. 30C, right). IR treatment further elevated this effect resulting in the largest cDC population for the STAT3i SPNP+IR group. Co-staining of CD45 and F4/80high cells with CD206 and Arg1 antibodies in the STAT3i SPNP+IR group confirmed that the vast majority of TAMs were of the M2 phenotype (FIG. 31).

Among all TME CD45+ immune cells, only M2 macrophages displayed the far-red Alexa Fluor 647 signal indicative of SPNPs suggesting that immune suppressive M2 macrophages are the primary TME-based immune cells that internalize SPNPs (FIG. 32).

Finally, maturation status of DCs in the draining lymph nodes (dLNs) of free STAT3i, SPNPs, STAT3i SPNPs and STAT3i SPNPs+IR treated GL26-OVA tumor-bearing mice was measured using flow cytometry. To examine the effect of SPNPs on DC activation in the dLNs, the expression of MHC II was assessed. An increase in the frequency of DCs: CD45+/CD11c+/MHC II+(~1.5-fold, p<0.0001) was observed in the dLN of STAT3i SPNPs treated mice compared to free-STAT3i and SPNP treated mice. This was further enhanced in the presence of IR by ~1.3-fold (p<0.0001) (FIG. 33). These data suggest that STAT3i SPNPs in combination with radiation induces the activation of DCs by enhancing the expression of MHC II, which is involved in antigen presentation.

Tumor rechallenge study. The current standard of care approaches, including surgical resection combined with focused radiation and the chemotherapeutic temozolomide, have been used to treat primary GBM tumors. However, owing to the aggressive and infiltrative nature of GBM, these patients, as a rule, experience recurrence contributing to the high mortality and dismal survival rates. Based on the encouraging immune response observed in the survival study, survivors from the STAT3i SPNP+IR treatment group were rechallenged. Tumors were implanted in the contralateral hemisphere of mice that were previously cured by the STAT3i SPNP+IR therapy. These mice did not receive any additional intervening therapy (FIG. 30D). As a control, normal mice were also implanted with tumors at the same timepoint and likewise received no treatment. As expected, the control group saw rapid tumor growth, increased signs of disease and had a MS of 27 DPI. Despite not receiving any additional treatment, all rechallenged mice survived to a second long-term survival point of 90 DPI (relative to the second tumor implantation, 180 days post initial tumor implantation) (FIG. 30E). IHC analysis of the brains yielded comparable results (FIG. 30F). H&E staining clearly showed the formation of a fully developed tumor mass in the control group, while members of the rechallenged cohort displayed no regions of necrosis, palisades or hemorrhages in either hemisphere (FIG. 30F, top). MBP staining confirmed that there was no overt disruption of the surrounding brain architecture (FIG. 30F, middle). Lastly, the presence of CD8 T cells was observed to be fivefold lower (FIG. 34) in the STAT3i SPNP rechallenge group compared to the control (FIG. 30F, bottom). Importantly, no adverse effects in the brains of rechallenged survivors were observed. Glioma cell death may associated with the concomitant release of antigens and damage-associated molecular patterns (DAMPs) leading to tumor antigen-specific T cell expansion and adaptive anti-glioma immunity. Without wishing to be bound by theory, the present results suggest a similar involvement of an adaptive immune response that appears to guard against secondary tumors; an essential condition of any successful GBM therapy that will require long-term eradication of migrating and resistant CSCs, typically missed by traditional therapies.

HSA, when polymerized, forms water-stable NP. These particles undergo pH responsive swelling, suggesting a flexible and dynamic architecture, contrary to more rigid synthetic polymer-based NP. In addition, the amphiphilic protein structure makes it biochemically compatible with biological therapeutics (siRNA), small molecule drugs, and targeting peptides.

Encouraged by results showing the accumulation of SPNPs in GBM tumors therapeutic efficacy of STAT3i SPNPs was evaluated in combination with focused radiotherapy. In the highly aggressive GBM GL26 model, a significant increase in MS is observed in mice treated with the combined therapy with 87.5% of mice reaching the long-term survival timepoint. In these mice, significantly reduced levels of STAT3 were observed, no apparent residual tumors, normal brain architecture, and a lack of inflammation was observed in response to the treatment. Increases in both tumor-antigen specific CD8 T cells in the brain TME along with a decrease in immune suppressive M2 macro-phages were observed, suggesting the activation of an anti-GBM immune response (FIG. 27). Finally, minimal signs of toxicity in the liver and no significant differences in the cellular components of blood relating to kidney and liver function were observed, suggesting no overt off-target side effects occurred as a result of the treatment.

Patients treated with conventional therapies including chemotherapeutics, radiation, and surgical resection, commonly experience recurrence in surrounding tissues contributing to GBM's high mortality rate. To further explore the observed immune response, mice reaching the long-term survival time-point were rechallenged with a second tumor in the contralateral hemisphere. Incredibly, in the absence of therapeutic intervention, all rechallenged mice survived to a second long-term survival timepoint. Rechallenged mice showed no overt signs of residual tumor, regions of necrosis, or disruption of the surrounding brain architecture (FIG. 30). Together, these studies further suggest the activation of an adaptive immune response, potentially capable of eradicating secondary tumors resulting from the aggressive and infiltrative nature of GBM.

Example 22

Synthetic protein nanoparticles (SPNP) with siRNA targeting ATG7 (autophagy related 7) with iRGD are formed with the following materials: human serum albumin (A1653, Sigma Aldrich), UltraPure DNase/RNase-free distilled water (10977023), ethylene glycol, O,O'-Bis[2-N-Succinimidyl-succinylamino)ethyl]polyethylene glycol ethylene glycol (713783), iRGD, Alexa Fluor Albumin from Bovine Serum (BSA)(A34785), Alexa Fluor 647 conjugate, Polyethyleneimine (181978), ATG7 siRNA (SR427399), DPBS (14190144), no calcium, no magnesium, Tween20.

The SPNP formulations are formed as follows. In the basic formulation, two solutions are prepared separately then combined. In the first solution, human serum albumin (7.5% w/v) is solubilized in a solvent system comprising ultrapure deionized water and ethylene glycol (80:20 v/v). In the second solution, a bi-functional macromer, O,O'-Bis[2-N-Succinimidyl-succinylamino)ethyl]polyethylene glycol ethylene glycol, is added at 10% w/w of the human serum albumin added to the first solution. To produce ATG7 siRNA loaded SPNPs with iRGD, the following is conducted. In the first solution, the peptide, iRGD, is added along with BSA Alexa Fluor 647 conjugate (0.25% w/w relative to the albumin) to produce fluorescently labeled SPNPs. Then, the siRNA, which is resuspended according to the manufacturer's protocol, was complexed for 30 minutes at room temperature under rotation with a 60 kDa branched polyethyleneimine (5 w/v %). The complexed solution was added to the first solution containing human serum albumin. Once mixed, the second solution or the bi-functional crosslinker solution was added to form the final formulation. For empty SPNP groups, all the components that were added in the iRGD ATG7 siRNA SPNPs were included except for the ATG7 siRNA.

SPNPs were fabricated via electrohydrodynamic jetting. The parameters used were the same as previously described. Briefly, the final formulation was loaded into 1 mL syringes equipped with a 1.5-inch 25-gauge stainless steel blunt needle. The formulation is pumped at a rate of 0.2 mL/hour to form droplets at the base of the needle. A voltage source is connected to the needle and grounded at the collection plate, located 6 inches from the base of the pump. The voltage is adjusted, typically to a range between 8 kV and 15 kV, to achieve a stable Taylor cone whereby rapid evaporation of the solvent occurs, creating solid nanoparticles on the collection plate. The collection plate is replaced with a clean plate every 30 minutes until the solution within the syringe emptied. The collection plates are enclosed and incubated for 7 days at 37° C. to form stable crosslinks.

SPNP collection and processing. After the one-week period of incubation, the SPNPs on collection plates are removed. About 3-4 mL of 0.01% Tween 20 in DPBS is added to each pan and physically agitated with plastic razor blades to release the SPNPs off the plate. The SPNP suspension is collected into a falcon tube. Each pan is agitated with fresh 0.01% Tween 20 in DPBS three times. The collected SPNPs are tip sonicated at an amplitude of 7 for 30 seconds (1 second on and 3 seconds off) in an ice bath to break up aggregates, strained through a 40 µm filter into a new falcon tube then centrifuged at 3220 rcf for 5 minutes. The supernatant is removed and distributed into 2 mL Eppendorf tubes and centrifuged for 1 hour at 4° C. at 21,500 rcf. The supernatant is discarded, and the resulting pellets are combined into a single 2 mL tube. The particles are washed two times with fresh DBPS without Tween 20.

Scanning electron Microscopy (SEM) samples are prepared by placing a silicon wafer on top of the collection plate during the jetting process. The samples are then placed on a copper tape covered SEM stub then gold coated for 40 seconds and visualized through the FEI NOVA 200 SEM/FIB instrument. The dry state SPNP quantification of morphology parameters is conducted through ImageJ analysis as described previously.

The hydrodynamic diameter and zeta potential is determined through Dynamic Light Scattering (DLS) on the Malvern Zetasizer. Samples are prepared by diluting the stock sample in DBPS and measured in folded capillary zeta cells. An average of at least three measurements is used to characterize each sample. Bicinchoninic acid assay (BCA assay) is used to quantify SPNP concentration. A standard curve is prepared for every SPNP concentration quantification measurement.

All possible combinations discussed and enumerated above and herein as optional features of the inventive materials and inventive methods of the present disclosure are specifically disclosed as embodiments.

In certain aspects, the present disclosure contemplates a nanoparticle. The nanoparticle comprises a cross-linked water-soluble protein. The water-soluble protein has an average molecular weight of greater than or equal to about 8 kDa and less than or equal to about 700 kDa. The cross-linked water-soluble protein defines a mesh structure having an average linear mesh size of greater than or equal to about 1 nm to less than or equal to about 4 nm Also specifically disclosed are combinations including this nanoparticle optionally with any one or any combination of more than one of the enumerated features (1)-(5). The nanoparticle of the first embodiment optionally has any one or any combination of more than one of the following features: (1) the nanoparticle further comprises a crosslinking agent reacted with the water-soluble protein; (2) the cross-linked water soluble protein is present at greater than or equal to about 50% by weight to less than or equal to about 95% by weight and the crosslinking agent is present at greater than or equal to about 5% by weight to less than or equal to about 50% by weight; (3) the cross-linking agent, prior to reacting with the water-soluble protein, comprises a reactive group selected from the group consisting of: an alkenyl group, an alkynyl group, a maleimide group, an active ester group, an anhydride group, an N-succinimidyl group, a triflate group, and combinations thereof; (4) the nanoparticle further comprises one or more of a therapeutic active ingredient, an imaging agent, and a targeting moiety; and/or (5) the water-soluble protein is selected from the group consisting of: ovalbumin, albumin, mucin, transferrin, insulin, lysozyme, hemoglobin, collagen, catalase, horseradish peroxidase, glucose oxidase, and combinations thereof.

In other aspects, the present disclosure contemplates a method of making a nanoparticle. The method comprise jetting a liquid comprising a water-soluble protein having an average molecular weight of greater than or equal to about 8 kDa and less than or equal to about 700 kDa and water through a nozzle. The liquid is exposed to an electric field sufficient to solidify the liquid and form the nanoparticle defining a mesh structure having an average linear mesh size of greater than or equal to about 1 nm to less than or equal to about 4 nm.

Also specifically disclosed are combinations including this method optionally with any one or any combination of more than one of the enumerated steps or features (6)-(9). The method of making the nanoparticle may include: (6) the liquid further comprising a crosslinking agent and during the exposing, the water-soluble protein is at least partially cross-linked; (7) the at least partially cross-linked water-soluble protein defines a mesh structure having an average linear mesh size of greater than or equal to about 1 nm to less than or equal to about 4 nm; (8) the electric field is formed by applying a potential difference between at least two electrodes from about 0.1 kV to about 25 kV; and/or (9) the liquid further comprises an additive selected from the group consisting of: a therapeutic active ingredient, an imaging agent, a biomolecule, a targeting moiety, and combinations thereof, wherein the additive is incorporated into the nanoparticle.

In further aspects, the present disclosure contemplates a nanoparticle that comprises a nanoparticle comprising a cross-linked water-soluble protein having an average molecular weight of greater than or equal to about 8 kDa to less than or equal to about 700 kDa and comprising disulfide bonds. The nanoparticle is substantially free of a distinct crosslinking agent.

Also specifically disclosed are combinations including this nanoparticle optionally with any one or any combination of more than one of the enumerated features (10)-(12). The nanoparticle of this embodiment optionally has any one or any combination of more than one of the following features: (10) the cross-linked water-soluble protein defines a mesh structure; (11) the cross-linked water-soluble protein is selected from the group consisting of: ovalbumin, albumin, human serum albumin, bovine serum albumin, transferrin. hemoglobin, IgG, enzymes, transport proteins, storage proteins, antibodies, aptamers, chemokines, hormonal proteins, polypeptides, and combinations thereof; and/or (12) the nanoparticle further comprises one or more of a therapeutic active ingredient, an imaging agent, a biomolecule, and a targeting moiety.

In yet further aspects, the present disclosure contemplates a method of making a nanoparticle comprising jetting a liquid comprising a water-soluble protein having an average molecular weight of greater than or equal to about 8 kDa to less than or equal to about 700 kDa and comprising disulfide bonds through a nozzle. The method also comprises exposing the liquid to an electric field sufficient to cross-link and solidify the liquid and form the nanoparticle that is substantially free of a distinct crosslinking agent.

Also specifically disclosed are combinations including this method optionally with any one or any combination of more than one of the enumerated steps or features (13)-(15). The method of making the nanoparticle may include (13) the water-soluble protein defines a mesh structure having an average linear mesh size of greater than or equal to about 1 nm to less than or equal to about 4 nm; (14) the electric field is formed by applying a potential difference between at least two electrodes from about 0.1 kV to about 25 kV; (14) the liquid further comprises an additive selected from the group consisting of: a therapeutic active ingredient, an imaging agent, a biomolecule, a targeting moiety, and combinations thereof, wherein the additive is incorporated into the nanoparticle; and/or (15) the water-soluble protein is selected from the group consisting of: ovalbumin, albumin, human serum albumin, bovine serum albumin, transferrin. hemoglobin, IgG, enzymes, transport proteins, storage proteins, antibodies, aptamers, chemokines, hormonal proteins, polypeptides, and combinations thereof.

In yet further aspects, the present disclosure contemplates a multicompartmental nanoparticle. The nanoparticle may comprise a first compartment defining at least a portion of an exposed surface of the multicompartmental nanoparticle and comprising a first composition having a water-soluble polymer having an average molecular weight of greater than or equal to about 8 kDa and less than or equal to about 700 kDa. The multicompartmental nanoparticle also comprises at least one additional compartment defining at least a portion of an exposed surface and comprising at least one additional composition distinct from the first composition.

Also specifically contemplated are combinations including this multicompartmental nanoparticle optionally with any one or any combination of more than one of the enumerated features (16)-(22). The multicompartmental nanoparticle of this embodiment optionally has any one or any combination of more than one of the following features: (16) the multicompartmental nanoparticle further comprises a crosslinking agent reacted with the water-soluble protein in the first compartment; (17) the water-soluble protein is present at greater than or equal to about 50% by weight to less than or equal to about 95% by weight and the cross-linking agent is present at greater than or equal to about 5% by weight to less than or equal to about 50% by weight; (18) the crosslinking agent, prior to reacting with the water-soluble protein, comprises a reactive group selected from the group consisting of: an alkenyl group, an alkynyl group, a maleimide group, an active ester group, an anhydride group, an N-succinimidyl group, a triflate group, and combinations thereof; (19) further comprising one or more of a therapeutic active ingredient, an imaging agent, a biomolecule, and a targeting moiety; (20) the water-soluble protein is selected from the group consisting of: ovalbumin, albumin, mucin, transferrin, insulin, lysozyme, hemoglobin, collagen, and combinations thereof (21) the water-soluble protein is a first water soluble protein and the at least one additional compartment comprises a second water-soluble protein; and/or (22) the second water-soluble protein is selected from the group consisting of: ovalbumin, albumin, mucin, transferrin, insulin, lysozyme, hemoglobin, collagen, and combinations thereof.

In further aspects, the present disclosure contemplates a nanoparticle comprising a cross-linked water-soluble protein having an average molecular weight of greater than or equal to about 8 KDa and less than or equal to about 700 kDa and comprising a therapeutic active ingredient.

Also specifically disclosed are combinations including this nanoparticle optionally with any one or any combination of more than one of the enumerated features (23)-(31). The nanoparticle of this embodiment optionally has any one or any combination of more than one of the following features: (23) the therapeutic active ingredient is selected from the group consisting of: DNA, RNA, plasmids, short interfering sequence of double stranded RNA (siRNA), messenger RNA (mRNA), transfer RNA, ribosomal RNA, small nuclear RNA, single stranded DNA, CRISPR CAS-9, aptamers, antibodies, peptides, targeting molecules, vitamins, and combinations thereof; (24) the nanoparticle further comprises a crosslinking agent reacted with the water-soluble protein; (25) the cross-linked water soluble protein is present at greater than or equal to about 50% by weight to less than or equal to about 95% by weight and the cross-linking agent is present at greater than or equal to about 5% by weight to less than or equal to about 50% by weight; (26) prior to reacting with the water-soluble protein, the cross-linking agent comprises a reactive group selected from the group consisting of: an alkenyl group, an alkynyl group, a maleimide group, an active ester group, an anhydride group, an N-succinimidyl group, a triflate group, and combinations thereof; (27) the nanoparticle further comprises one or more of an imaging agent, an additional biomolecule, and a targeting moiety; (28) the therapeutic active ingredient is selected from the group consisting of: a drug, a steroid, and combinations thereof; (29) the drug is selected from the group consisting of: paclitaxel, cis-platin, doxorubicin, and combinations thereof; (30) the therapeutic active ingredient is selected from the group consisting of: an antibody, an aptamer, a chemokine, a peptide drug, and combinations thereof; (31) the water-soluble protein is selected from the group consisting of: ovalbumin, albumin, mucin, transferrin, insulin, lysozyme, hemoglobin, collagen, catalase, horseradish peroxidase, glucose oxidase, and combinations thereof.

The present disclosure also contemplates a nanoparticle comprising a cross-linked water-soluble protein having an average molecular weight of greater than or equal to about 8 kDa and less than or equal to about 700 kDa (e.g., from about 8 kDa to about 15 kDa, from about 10 kDa to about 20 kDa, from about 15 kDa to about 25 kDa, from about 25 kDa to about 50 kDa, from about 50 kDa to about 100 kDa, from about 100 kDa to about 200 kDa, from about 200 kDa to about 300 kDa, from about 300 kDa to about 400 kDa, from about 400 kDa to about 500 kDa, from about 500 kDa to about 600 kDa, or from about 600 kDa to about 700 kDa). In some embodiments, the nanoparticle has a mesh structure with an average linear mesh size of greater than or equal to about 1 nm to less than or equal to about 4 nm (e.g., from about 1 nm to about 3 nm, or from about 2 nm to about 4 nm, e.g., from about 1 nm to about 2 nm, from about 2 nm to about 3 nm, or from about 3 nm to about 4 nm, e.g., about 1 nm, about 2 nm, about 3 nm, or about 4 nm).

Also specifically disclosed are combinations including this nanoparticle optionally with any one or any combination of more than one of the enumerated features (32)-(36). The nanoparticle optionally has any one or any combination of more than one of the following features: (32) the nanoparticle further comprises a crosslinking agent reacted with (e.g., conjugated to) the water-soluble protein; (33) the cross-linked water soluble protein is present at greater than or equal to about 50% by weight to less than or equal to about 95% by weight (e.g., about 50% by weight, about 55% by weight, about 60% by weight, about 65% by weight, about 70% by weight, about 75% by weight, about 80% by weight, about 85% by weight, about 90% by weight, or about 95% by weight) (e.g., dry weight) of the nanoparticle and the crosslinking agent is present at greater than or equal to about 5% by weight to less than or equal to about 50% by weight (e.g., about 5% by weight, about 10% by weight, about 15% by weight, about 20% by weight, about 25% by weight, about 30% by weight, about 35% by weight, about 40% by weight, about 45% by weight, or about 50% by weight) (e.g., dry weight) of the nanoparticle; (34) prior to reacting with the water-soluble protein, the crosslinking agent comprises a reactive group selected from the group consisting of an alkenyl group, an alkynyl group, a maleimide group, an active ester group, an anhydride group, an N-succinimidyl group, a triflate group, and combinations thereof; (35) the nanoparticle further comprises one or more of a therapeutic active ingredient (e.g., a biomolecule, e.g., a nucleic acid, e.g., DNA), an imaging agent, and a targeting moiety; and/or (36) the water-soluble protein is selected from the group consisting of albumin, ovalbumin, mucin, transferrin, insulin, lysozyme, hemoglobin, collagen, catalase, horseradish peroxidase, glucose oxidase, and combinations thereof.

In another aspect, the present disclosure contemplates a method of treating a subject having a cancer, such as a cancer characterized by one or more intracranial tumors (e.g., glioblastoma, diffuse astrocytoma). The method includes administering to the subject the nanoparticle of any one of the preceding embodiments or the optional enumerated features in an effective amount to treat the cancer (e.g., glioblastoma, astrocytoma).

In another aspect, the present disclosure provides a pharmaceutical composition including the nanoparticle of any one of the preceding embodiments or the optional enumerated features.

In yet further aspects, the present disclosure also contemplates a method of making a nanoparticle that comprises jetting a liquid comprising a water-soluble protein having an average molecular weight of greater than or equal to about 8 kDa and less than or equal to about 700 kDa (e.g., from about 8 kDa to about 15 kDa, from about 10 kDa to about 20 kDa, from about 15 kDa to about 25 kDa, from about 25 kDa to about 50 kDa, from about 50 kDa to about 100 kDa, from about 100 kDa to about 200 kDa, from about 200 kDa to about 300 kDa, from about 300 kDa to about 400 kDa, from about 400 kDa to about 500 kDa, from about 500 kDa to about 600 kDa, or from about 600 kDa to about 700 kDa) and water (e.g., water containing one or more solutes, e.g., buffers) through a nozzle. The method also comprises exposing the liquid to an electric field sufficient to solidify the liquid and form the nanoparticle. The nanoparticle has a mesh structure having an average linear mesh size of greater than or equal to about 1 nm to less than or equal to about 4 nm (e.g., from about 1 nm to about 3 nm, or from about 2 nm to about 4 nm, e.g., from about 1 nm to about 2 nm, from about 2 nm to about 3 nm, or from about 3 nm to about 4 nm, e.g., about 1 nm, about 2 nm, about 3 nm, or about 4 nm).

Also specifically disclosed are combinations including this method optionally with any one or any combination of more than one of the enumerated steps or features (37)-(40). The method of making the nanoparticle may include: (37) the liquid further comprising a crosslinking agent and during the exposing, the water-soluble protein is at least partially cross-linked; (38) the at least partially cross-linked water-soluble protein defines a mesh structure having an average linear mesh size of greater than or equal to about 1 nm to less than or equal to about 4 nm (e.g., from about 1 nm to about 3 nm, or from about 2 nm to about 4 nm, e.g., from about 1 nm to about 2 nm, from about 2 nm to about 3 nm, or from about 3 nm to about 4 nm, e.g., about 1 nm, about 2 nm, about 3 nm, or about 4 nm); (39) the electric field is formed by applying a potential difference between at least two electrodes from about 0.1 kV to about 25 kV (e.g., from about 0.1 kV to about 0.5 kV, from about 0.5 kV to about 1.0 kV, from about 1.0 kV to about 5 kV, from about 5 kV to about 10 kV, from about 10 kV to about 15 kV, from about 15 kV to about 20 kV, or from about 20 kV to about 25 kV, e.g., about 0.1 kV, about 0.5 kV, about 1.0 kV, about 2.0 kV, about 5.0 kV, about 10 kV, about 15 kV, about 20 kV, or about 25 kV); and/or (40) the liquid further comprises an additive selected from the group consisting of a therapeutic active ingredient, an imaging agent, a biomolecule, a targeting moiety, and a combination thereof, wherein the additive is incorporated into the nanoparticle.

In certain other aspects, the present disclosure contemplates a nanoparticle comprising a cross-linked water-soluble protein having an average molecular weight of greater than or equal to about 8 kDa to less than or equal to about 700 kDa (e.g., from about 8 kDa to about 15 kDa, from about 10 kDa to about 20 kDa, from about 15 kDa to about 25 kDa, from about 25 kDa to about 50 kDa, from about 50 kDa to about 100 kDa, from about 100 kDa to about 200 kDa, from about 200 kDa to about 300 kDa, from about 300 kDa to about 400 kDa, from about 400 kDa to about 500 kDa, from about 500 kDa to about 600 kDa, or from about 600 kDa to about 700 kDa). The cross-linked water-soluble protein comprises disulfide bonds. The nanoparticle is also substantially free of a distinct crosslinking agent.

Also specifically disclosed are combinations including this nanoparticle optionally with any one or any combination of more than one of the enumerated features (41)-(43). The nanoparticle optionally has any one or any combination of more than one of the following features: (41) the cross-linked water-soluble protein defines a mesh structure; (42) the cross-linked water-soluble protein is selected from the group consisting of albumin, human serum albumin, ovalbumin, bovine serum albumin, transferrin. hemoglobin, IgG, enzymes, transport proteins, storage proteins, antibodies, aptamers, chemokines, hormonal proteins, polypeptides, and combinations thereof; and/or (43) the nanoparticle further comprises one or more of a therapeutic active ingredient (e.g., a biomolecule, e.g., a nucleic acid, e.g., DNA, e.g., RNA), an imaging agent, and a targeting moiety.

In another aspect, the present disclosure contemplates a method of making a nanoparticle comprising: jetting a liquid comprising a water-soluble protein having an average molecular weight of greater than or equal to about 8 kDa to less than or equal to about 700 kDa (e.g., from about 8 kDa to about 15 kDa, from about 10 kDa to about 20 kDa, from about 15 kDa to about 25 kDa, from about 25 kDa to about 50 kDa, from about 50 kDa to about 100 kDa, from about 100 kDa to about 200 kDa, from about 200 kDa to about 300 kDa, from about 300 kDa to about 400 kDa, from about 400 kDa to about 500 kDa, from about 500 kDa to about 600 kDa, or from about 600 kDa to about 700 kDa) through a nozzle. The water-soluble protein comprises disulfide bonds.

The method also comprises exposing the liquid to an electric field sufficient to cross-link and solidify the liquid and form the nanoparticle substantially free of a distinct crosslinking agent.

Also specifically disclosed are combinations including this method optionally with any one or any combination of more than one of the enumerated steps or features (44)-(47). The method of making the nanoparticle may include: (44) the water-soluble protein has a mesh structure having an average linear mesh size of greater than or equal to about 1 nm to less than or equal to about 4 nm (e.g., from about 1 nm to about 3 nm, or from about 2 nm to about 4 nm, e.g., from about 1 nm to about 2 nm, from about 2 nm to about 3 nm, or from about 3 nm to about 4 nm, e.g., about 1 nm, about 2 nm, about 3 nm, or about 4 nm); (45) the electric field is formed by applying a potential difference between at least two electrodes from about 0.1 kV to about 25 kV (e.g., from about 0.1 kV to about 0.5 kV, from about 0.5 kV to about 1.0 kV, from about 1.0 kV to about 5 kV, from about 5 kV to about 10 kV, from about 10 kV to about 15 kV, from about 15 kV to about 20 kV, or from about 20 kV to about 25 kV, e.g., about 0.1 kV, about 0.5 kV, about 1.0 kV, about 2.0 kV, about 5.0 kV, about 10 kV, about 15 kV, about 20 kV, or about 25 kV); (46) the liquid further comprises an additive selected from the group consisting of a therapeutic active ingredient, an imaging agent, a biomolecule, a targeting moiety, and combinations thereof, wherein the additive is incorporated into the nanoparticle; and/or (47) the water-soluble protein is selected from the group consisting of ovalbumin, albumin, human serum albumin, bovine serum albumin, transferrin, catalase, horseradish peroxidase, glucose oxidase, hemoglobin, IgG, enzymes, transport proteins, storage proteins, antibodies, aptamers, chemokines, hormonal proteins, polypeptides, and combinations thereof.

The present disclosure also contemplates a multicompartmental nanoparticle comprising a first compartment defining at least a portion of an exposed surface of the multicompartmental nanoparticle and comprising a first composition having a water-soluble polymer with an average molecular weight of greater than or equal to about 8 kDa and less than or equal to about 700 kDa (e.g., from about 8 kDa to about 15 kDa, from about 10 kDa to about 20 kDa, from about 15 kDa to about 25 kDa, from about 25 kDa to about 50 kDa, from about 50 kDa to about 100 kDa, from about 100 kDa to about 200 kDa, from about 200 kDa to about 300 kDa, from about 300 kDa to about 400 kDa, from about 400 kDa to about 500 kDa, from about 500 kDa to about 600 kDa, or from about 600 kDa to about 700 kDa). The multicompartmental nanoparticle also comprises at least one additional compartment constituting (e.g., defining) at least a portion of an exposed surface and comprising at least one additional composition distinct from the first composition.

Also specifically disclosed are combinations including this multicompartmental nanoparticle optionally with any one or any combination of more than one of the enumerated features (48)-(54). The nanoparticle of this embodiment optionally has any one or any combination of more than one of the following features: (48) the multicompartmental nanoparticle further comprises a crosslinking agent reacted with the water-soluble protein in the first compartment; (49) the water soluble protein is present at greater than or equal to about 50% by weight to less than or equal to about 95% by weight (e.g., about 50% by weight, about 55% by weight, about 60% by weight, about 65% by weight, about 70% by weight, about 75% by weight, about 80% by weight, about 85% by weight, about 90% by weight, or about 95% by weight) (e.g., dry weight) of the nanoparticle and the cross-linking agent is present at greater than or equal to about 5% by weight to less than or equal to about 50% by weight (e.g., about 5% by weight, about 10% by weight, about 15% by weight, about 20% by weight, about 25% by weight, about 30% by weight, about 35% by weight, about 40% by weight, about 45% by weight, or about 50% by weight) (e.g., dry weight) of the nanoparticle; (50) prior to reacting with the water-soluble protein, the crosslinking agent comprises a reactive group selected from the group consisting of: an alkenyl group, an alkynyl group, a maleimide group, an active ester group, an anhydride group, an N-succinimidyl group, a triflate group, and combinations thereof; (51) the multicompartmental nanoparticle further comprises one or more of a therapeutic active ingredient, an imaging agent, a biomolecule, and a targeting moiety; (52) the water-soluble protein is selected from the group consisting of albumin, ovalbumin, mucin, transferrin, insulin, lysozyme, hemoglobin, collagen, catalase, horseradish peroxidase, glucose oxidase, and combinations thereof; (53) the water-soluble protein is a first water soluble protein and the at least one additional compartment comprises a second water-soluble protein; and/or (54) the second water-soluble protein is selected from the group consisting of albumin, ovalbumin, mucin, transferrin, insulin, lysozyme, hemoglobin, collagen, catalase, horseradish peroxidase, glucose oxidase, and combinations thereof.

In yet other aspects, the present disclosure contemplates a method of treating a subject having a cancer (e.g., glioblastoma), the method including administering to the subject the multicompartmental nanoparticle of any one of the preceding embodiments including any of the optional features (48)-(54) in an effective amount to treat the cancer (e.g., glioblastoma).

In yet other aspects, the present disclosure contemplates a method of treating a subject having a cancer (e.g., diffuse astrocytoma), the method including administering to the subject the multicompartmental nanoparticle of any one of the preceding embodiments including any of the optional features (48)-(54) in an effective amount to treat the cancer (e.g., diffuse astrocytoma).

The present disclosure also contemplates a pharmaceutical composition including the multicompartmental nanoparticle of any one of the preceding embodiments, including any of the optional features (48)-(54).

In other aspects, the present disclosure also relates to a nanoparticle comprising a cross-linked water-soluble protein having an average molecular weight of greater than or equal to about 8 KDa and less than or equal to about 700 kDa (e.g., from about 8 kDa to about 15 kDa, from about 10 kDa to about 20 kDa, from about 15 kDa to about 25 kDa, from about 25 kDa to about 50 kDa, from about 50 kDa to about 100 kDa, from about 100 kDa to about 200 kDa, from about 200 kDa to about 300 kDa, from about 300 kDa to about 400 kDa, from about 400 kDa to about 500 kDa, from about 500 kDa to about 600 kDa, or from about 600 kDa to about 700 kDa). In some embodiments, the nanoparticle also comprises a therapeutic active ingredient (e.g., a biomolecule, e.g., a nucleic acid, e.g., DNA).

Also specifically disclosed are combinations including this nanoparticle optionally with any one or any combination of more than one of the enumerated features (55)-(63). The nanoparticle of this embodiment optionally has any one or any combination of more than one of the following features: (55) the therapeutic active ingredient is selected from the group consisting of a nucleic acid (e.g., DNA, RNA, plasmid, short interfering sequence of double stranded RNA (siRNA, e.g., siRNA against STAT3, siRNA against ATG7), messenger RNA (mRNA), transfer RNA, ribosomal RNA, small nuclear RNA, single stranded DNA, CRISPR CAS-9, or aptamer), a protein or peptide (e.g., an antibody or other targeting molecule), a vitamin, and a combination thereof; (56) the nanoparticle further comprises a crosslinking agent reacted with the water-soluble protein; (57) the water soluble protein is present at (e.g., accounts for) greater than or equal to about 50% by weight to less than or equal to about 95% by weight (e.g., about 50% by weight, about 55% by weight, about 60% by weight, about 65% by weight, about 70% by weight, about 75% by weight, about 80% by weight, about 85% by weight, about 90% by weight, or about 95% by weight) (e.g., dry weight) of the nanoparticle and the crosslinking agent is present at (e.g., accounts for) greater than or equal to about 5% by weight to less than or equal to about 50% by weight (e.g., about 5% by weight, about 10% by weight, about 15% by weight, about 20% by weight, about 25% by weight, about 30% by weight, about 35% by weight, about 40% by weight, about 45% by weight, or about 50% by weight) (e.g., dry weight) of the nanoparticle; (58) prior to reacting with the water-soluble protein, the crosslinking agent comprises a reactive group selected from the group consisting of an alkenyl group, an alkynyl group, a maleimide group, an active ester group, an anhydride group, an N-succinimidyl group, a triflate group, and a combinations thereof; (59) the nanoparticle further comprises one or more of an imaging agent, an additional biomolecule, and a targeting moiety; (60) the therapeutic active ingredient is selected from the group consisting of a drug, a steroid, and combinations thereof; (61) the drug is selected from the group consisting of: paclitaxel, cis-platin, doxorubicin, and combinations thereof; (62) the therapeutic active ingredient is selected from the group consisting of an antibody, an aptamer, a chemokine, a peptide drug, and combinations thereof; and/or (63) the water-soluble protein is selected from the group consisting of albumin, ovalbumin, mucin, transferrin, insulin, lysozyme, hemoglobin, collagen, catalase, horseradish peroxidase, glucose oxidase, and a combinations thereof.

In yet another aspect, the present disclosure contemplates a method of treating a subject having a cancer (e.g., glioblastoma, diffuse astrocytoma), the method including administering to the subject the nanoparticle of any one of the preceding embodiments, including any of the optional features (55)-(63), in an effective amount to treat the cancer (e.g., glioblastoma, diffuse astrocytoma).

In a further aspect, the present disclosure provides a pharmaceutical composition including the nanoparticle of any one of the preceding embodiments, including any of the optional features (55)-(63).

The foregoing description of the embodiments has been provided for purposes of illustration and description. It is not intended to be exhaustive or to limit the disclosure. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the disclosure, and all such modifications are intended to be included within the scope of the disclosure.

What is claimed is:

1. A nanoparticle comprising an inhibitor of a transcription factor and a cross-linked water-soluble protein having a mesh structure encapsulating the inhibitor of the transcription factor, wherein the water-soluble protein has an average molecular weight of greater than or equal to about 8 kDa and less than or equal to about 700 kDa and the water-soluble protein has a predominantly native conformation due to the absence of alcohols or acetone during formation of the mesh structure.

2. The nanoparticle of claim 1, wherein the mesh structure has an average linear mesh size of greater than or equal to about 1 nm to less than or equal to about 4 nm.

3. The nanoparticle of claim 1, wherein the nanoparticle comprises a crosslinking agent conjugated to the water-soluble protein and the cross-linked water soluble protein is present at greater than or equal to about 50% by weight to less than or equal to about 95% by weight, and wherein the crosslinking agent is present at greater than or equal to about 5% by weight to less than or equal to about 50% by weight.

4. The nanoparticle of claim 3, wherein the crosslinking agent, prior to reacting with the water-soluble protein, comprises a reactive group selected from the group consisting of an alkenyl group, an alkynyl group, a maleimide group, an active ester group, an anhydride group, an N-succinimidyl group, a triflate group, and a combination thereof.

5. The nanoparticle of claim 3, wherein the crosslinking agent is a homo-bifunctional polymer.

6. The nanoparticle of claim 1, further comprising one or more of a therapeutic active ingredient, an imaging agent, and a targeting moiety.

7. The nanoparticle of claim 1, wherein the inhibitor of the transcription factor is a therapeutic nucleic acid.

8. The nanoparticle of claim 7, wherein the therapeutic nucleic acid is an RNA molecule.

9. The nanoparticle of claim 7, wherein the RNA molecule is an siRNA molecule against STAT3 or siRNA against ATG7.

10. The nanoparticle of claim 7, wherein the nanoparticle comprises a targeting moiety that is a cell penetrating peptide.

11. The nanoparticle of claim 10, wherein the cell penetrating peptide is iRGD.

12. The nanoparticle of claim 1, wherein the water-soluble protein is selected from the group consisting of albumin, ovalbumin, mucin, transferrin, insulin, lysozyme, hemoglobin, collagen, catalase, horseradish peroxidase, glucose oxidase, and combinations thereof.

13. The nanoparticle of claim 1, wherein the water-soluble protein is albumin, the nanoparticle further comprises a targeting moiety that is iRGD, and the inhibitor of the transcription factor is a therapeutic nucleic acid.

14. The nanoparticle of claim 13, wherein the therapeutic nucleic acid is siRNA against STAT3 or siRNA against ATG7.

15. A method of treating a subject having cancer characterized by one or more intracranial tumors, the method comprising:
    administering to the subject a nanoparticle comprising an inhibitor of a transcription factor and a cross-linked water-soluble protein having a mesh structure encapsulating the inhibitor of the transcription factor, wherein the water-soluble protein has an average molecular weight of greater than or equal to about 8 kDa and less than or equal to about 700 kDa and the water-soluble protein has a predominantly native conformation due to the absence of alcohols or acetone during formation of the mesh structure.

16. The method of claim 15, wherein the cancer is at least one of a glioblastoma or a diffuse astrocytoma.

17. The method of claim 15, wherein the method further comprises administering a concurrent radiotherapy to the subject.

18. The method of claim 15, further comprising one or more of a therapeutic active ingredient, an imaging agent, and a targeting moiety.

19. The method of claim 15, wherein the inhibitor of the transcription factor is a therapeutic nucleic acid that is an RNA molecule.

20. The method of claim 19, wherein the RNA molecule is an siRNA molecule against STAT3 or siRNA against ATG7.

21. The method of claim 15, wherein the nanoparticle comprises a targeting moiety that is a cell penetrating peptide comprising iRGD and the water-soluble protein is albumin.

22. The method of claim 15, wherein the administering generates an anti-tumor cytotoxic T cell-mediated immune response in the subject.

23. The method of claim 15, wherein the administering generates an anti-tumor humoral immune response in the subject.

24. The nanoparticle of claim 1, wherein the mesh structure defines a network of the cross-linked water soluble protein defining a plurality of openings therebetween.

25. The nanoparticle of claim 24, wherein the mesh structure has an overall open volume of greater than or equal to about 50 volume % of the nanoparticle volume.

* * * * *